(12) United States Patent
Nara et al.

(10) Patent No.: US 6,861,530 B2
(45) Date of Patent: Mar. 1, 2005

(54) PIPERIDINE DERIVATIVES

(75) Inventors: Shinji Nara, Shizuoka (JP); Rieko Nakatsu, Shizuoka (JP); Yutaka Kanda, Shizuoka (JP); Shiro Akinaga, Tokyo (JP); Mitsunobu Hara, Tokyo (JP); Jun Eishima, Gunma (JP); Timothy A. Grese, Indianapolis, IN (US); Douglas L. Gernert, Indianapolis, IN (US)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/899,186

(22) Filed: Jul. 6, 2001

(65) Prior Publication Data
US 2002/0137770 A1 Sep. 26, 2002

Related U.S. Application Data
(60) Provisional application No. 60/216,666, filed on Jul. 7, 2000.

(51) Int. Cl.[7] .................... C07D 211/68; C07D 211/80; C07D 213/02; C07D 401/00; C07D 409/00

(52) U.S. Cl. ................. 546/192; 546/193; 546/194; 546/197; 546/199; 546/201; 546/202; 546/205; 546/207; 546/208; 546/209; 546/210; 546/211; 546/212; 546/213; 546/214

(58) Field of Search ................. 546/193, 194, 546/192, 197, 199, 201, 202, 205, 207, 208, 209, 210, 211, 212, 213, 214

(56) References Cited

FOREIGN PATENT DOCUMENTS

WO    WO 01/85716    * 11/2001    ................. 546/193

* cited by examiner

*Primary Examiner*—Rita Desai
*Assistant Examiner*—Raymond Covington
(74) *Attorney, Agent, or Firm*—Fitzpatrick, Cella, Harper & Scinto

(57) ABSTRACT

This invention relates to substituted piperidine derivatives having at least one six-membered ring substituent. The piperidine derivatives exhibit antitumor activity and are useful as pharmaceuticals such as an antitumor agent.

26 Claims, No Drawings

PIPERIDINE DERIVATIVES

This application claims the benefit of U.S. Provisional Patent Application No. 60/216,666, filed Jul. 7, 2000.

FIELD OF THE INVENTION

This invention relates to piperidine derivatives having antitumor activity and useful as pharmaceuticals such as an antitumor agent.

BACKGROUND ART

4-Acetonyl-3-nitro-1-phenylmethylpiperidine (*Tetrahedron Lett.*, 31, 3039 (1990)) and 3-nitro-2-phenylpiperidine (*Bioorg. Med. Chem. Lett.*, 5, 1271 (1995) are known, but their pharmacological activities are unknown.

An object of the present invention is to provide piperidine derivatives or pharmaceutically acceptable salts thereof which are useful as pharmaceuticals such as an antitumor agent.

SUMMARY OF THE INVENTION

As a result of searching for an antitumor agent effective on solid tumors, the present inventors have found that piperidine derivatives are of low toxicity and effective on solid tumors and completed the present invention.

This invention relates to the following (1) to (5).

(1) Piperidine derivatives represented by formula (I):

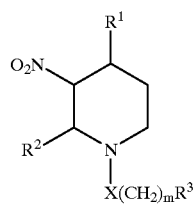

wherein m represents an integer of 0 to 5;

$R^1$ and $R^2$ each independently represent a substituted or unsubstituted lower alkyl group, a substituted or unsubstituted lower alkenyl group, a substituted or unsubstituted lower alkynyl group, a substituted or unsubstituted aryl group, a substituted or unsubstituted aralkyl group, or a substituted or unsubstituted heterocyclic group;

$R^3$ represents a hydrogen atom, a substituted or unsubstituted alkyl group, a substituted or unsubstituted aryl group, or a substituted or unsubstituted heterocyclic group; and X represents a bond or CO;

or pharmaceutically acceptable salts thereof.

(2) The piperidine derivatives or the pharmaceutically acceptable salts thereof according to (1) above, wherein $R^1$ is a substituted or unsubstituted aryl group, a substituted or unsubstituted aralkyl group, or a substituted or unsubstituted heterocyclic group, and $R^2$ is a substituted or unsubstituted aryl group, or a substituted or unsubstituted heterocyclic group.

(3) The piperidine derivatives or the pharmaceutically acceptable salts thereof according to (1) above, wherein m is 1 and X is a bond.

(4) The piperidine derivatives or the pharmaceutically acceptable salts thereof according to (2) above, wherein m is 1 and X is a bond.

(5) A pharmaceutical composition which comprises as an active ingredient the piperidine derivative or the pharmaceutically acceptable salt thereof according to any one of (1) to (4) above, and a pharmaceutically acceptable diluent or carrier.

(6) A method of treating a patient with tumor, which comprises administrating to said patient a pharmacologically effective amount of the piperidine derivative or the pharmaceutically acceptable salt thereof according to any one of (1) to (4) above.

The compound represented by formula (I) will hereinafter be referred to as a compound (I); the same designation will apply to compounds of other formula numbers.

DETAILED DESCRIPTION OF THE INVENTION

In the definitions of the groups in formula (I), the lower alkyl group includes straight-chain or branched alkyl groups having 1 to 10 carbon atoms, such as methyl, ethyl, propyl, isopropyl, butyl, isobutyl, sec-butyl, tert-butyl, pentyl, isopentyl, neopentyl, hexyl, heptyl, octyl, nonyl, decyl, cyclopropyl, cyclobutyl, cyclopentyl, cyclohexyl, cycloheptyl, cyclooctyl, and adamantyl.

The lower alkenyl group includes straight-chain or branched alkenyl groups having 2 to 10 carbon atoms, such as vinyl, allyl, methacryl, crotyl, 1-propenyl, prenyl, isopropenyl, butenyl, 2-methyl-2-butenyl, pentenyl, hexenyl, heptenyl, 2,6-dimethyl-5-heptenyl, cyclopropenyl, cyclobutenyl, cyclopentenyl, and cyclohexenyl.

The lower alkynyl group includes straight-chain or branched alkynyl groups having 2 to 10 carbon atoms, such as ethynyl, propynyl, butynyl, pentynyl, hexynyl, heptynyl, and octynyl.

The aryl group includes monocyclic, bicyclic or tricyclic carbon rings having 6 to 14 carbon atoms, wherein each ring is 3-membered to 7-membered and at least one ring is aromatic ring, such as phenyl, naphthyl, anthryl, phenanthryl, tetrahydronaphthyl, indanyl, indenyl, and the like.

The aralkyl group includes those having 7 to 20 carbon atoms, such as benzyl, phenethyl, benzhydryl, naphthylmethyl, and trityl.

The heterocyclic group includes aromatic heterocyclic groups and alicyclic heterocyclic groups. The aromatic heterocyclic groups include 5- or 6-membered monocyclic, aromatic and heterocyclic groups containing at least one atom selected from a nitrogen atom, an oxygen atom and a sulfur atom, and fused aromatic heterocyclic groups containing at least one atom selected from a nitrogen atom, an oxygen atom and a sulfur atom wherein two or three 3- to 8-membered rings are fused. The alicyclic heterocyclic groups include 5- or 6-membered monocyclic, alicyclic and heterocyclic groups containing at least one atom selected from a nitrogen atom, an oxygen atom and a sulfur atom, and fused alicyclic heterocyclic groups containing at least one atom selected from a nitrogen atom, an oxygen atom and a sulfur atom wherein two or three 3- to 8-membered rings are fused. Specific examples of the heterocyclic groups are azepinyl, benzimidazolyl, benzofurazanyl, benzopyranyl, benzothiopyranyl, benzofuryl, benzothiazolyl, benzothiadiazolyl, benzothienyl, benzoxazolyl, 1,4-benzodioxanyl, 1,3-benzodioxolyl, chromanyl, cinnolinyl, dihydrobenzofuranyl, dihydrobenzofuryl, dihydrobenzothienyl, dihydrobenzopyranyl, dihydrobenzothiopyranyl, furyl, imidazolidinyl, imidazolyl, imidazothiazolyl, indolinyl, indolyl, isochromanyl, isoindolyl, 1,3-dioxolanyl, 1,3-dioxolyl, 1,4-dioxolanyl, 1,3-dithiolanyl, isoxazolyl, isoquinolyl, isothiazolyl, isothiazolidinyl, morpholinyl, naphthylidinyl, oxadiazolyl, oxazolyl, 2-oxoazepinyl, 2-oxopiperazinyl, 2-oxopyrrolidinyl, piperidyl, piperazinyl, pyridyl, pyridyl N-oxide, pyrazinyl, pyrazolinyl, pyrazolyl, pyrimidinyl, pyridonyl, pyrrolidinyl, pyrrolyl, quinazolinyl, quinolinyl, quinoxalinyl, tetrahydrofuryl, tetrahydroisoquinolyl, tetrahydroquinolyl, tetrahydropyranyl, tetrazolyl, thiadiazolyl, thiazolyl, thiazolinyl, thienofuryl, thienothienyl, thienyl, thiomorpholino, and triazolyl.

The substituent(s) in the substituted lower alkyl group, the substituted lower alkenyl group, the substituted lower alkynyl group, the substituted aryl group, the substituted aralkyl group, and the substituted heterocyclic group may be 1 to 3 groups for each, which may be the same or different, selected from a hydroxyl group, a halogen atom, a nitro group, a cyano group, an amino group, a carboxyl group, $B(OH)_2$, $SO_3H$, $PO(OH)_2$, $PO(OR^4)_2$ (wherein $R^4$ represents a lower alkyl group), a substituted or unsubstituted lower alkyl group, a substituted or unsubstituted lower alkenyl group, a substituted or unsubstituted lower alkynyl group, a substituted or unsubstituted aryl group, a substituted or unsubstituted heterocyclic group, a substituted or unsubstituted aralkyl group, a lower alkylthio group, a sulfamyloxy group, a carbamoyloxy group, a substituted or unsubstituted lower alkoxy group, a lower alkenyloxy group, an alkanoyloxy group, an aryloxy group, an aroyloxy group, an aralkyloxy group, a mono- or di(lower alkyl) aminocarbonyloxy group, a lower alkoxycarbonyloxy group, a substituted or unsubstituted lower alkylsulfonyloxy group, a lower alkanoyl group, a lower alkoxycarbonyl group, a substituted or unsubstituted mono- or di(lower alkyl)amino group, a hydroxyamino group, a lower alkoxycarbonylamino group, a lower alkanoylamino group, a lower alkylsulfonylamino group, a substituted or unsubstituted arylsulfonylamino group, a substituted or unsubstituted aralkylamino group, a sulfamylamino group, a carbamoylamino group, a lower alkylsulfonyl group, a lower alkylsulfinyl group, an arylsulfonyl group, a heterocycle-carbonyloxy group, a camphanoyloxy group, a methylenedioxy group, an ethylenedioxy group, and the like. The position of the substitution is not particularly limited. The aryl moiety in the aryl, aryloxy, aroyloxy, arylsulfonyl and arylsulfonylamino groups has the same definition as the above-described aryl group. The aralkyl moiety in the aralkyl, aralkyloxy and aralkylamino groups has the same definition as the above-described aralkyl group. The heterocyclic moiety in the heterocyclic and heterocycle-carbonyloxy groups has the same definition as the above-described heterocyclic group. The lower alkyl moiety in the lower alkyl, lower alkylthio, lower alkoxy, mono- or di(lower alkyl)aminocarbonyloxy, lower alkoxycarbonyloxy, lower alkylsulfonyloxy, lower alkoxycarbonyl, mono- or di(lower alkyl)amino, lower alkoxycarbonylamino, lower alkylsulfonylamino, lower alkylsulfonyl, and lower alkylsulfinyl groups has the same definition as the above-described lower alkyl group. The lower alkenyl moiety in the lower alkenyl and lower alkenyloxy groups has the same definition as the above-described lower alkenyl group. The lower alkynyl group has the same meaning as the above-described lower alkynyl group. The lower alkanoyl moiety in the lower alkanoyl and lower alkanoylamino groups includes straight-chain or branched alkanoyl groups having 1 to 7 carbon atoms, such as formyl, acetyl, propionyl, butyryl, isobutyryl, valeryl, isovaleryl, pivaloyl, hexanoyl, and heptanoyl. The alkanoyl moiety in the alkanoyloxy group includes straight-chain or branched alkanoyl groups having 1 to 20 carbon atoms, such as formyl, acetyl, propionyl, butyryl, isobutyryl, valeryl, isovaleryl, pivaloyl, hexanoyl, heptanoyl, octanoyl, nonanoyl, decanoyl, undecanoyl, dodecanoyl, tridecanoyl, and eicosanoyl. The halogen atom means a fluorine atom, a chlorine atom, a bromine atom or an iodine atom. The substituent(s) in the substituted lower alkyl group, the substituted lower alkenyl group, the substituted lower alkynyl group, the substituted aryl group, the substituted heterocyclic group, the substituted lower alkoxy group, the substituted mono- or di(lower alkyl)amino group, the substituted lower alkylsulfonyloxy group, the substituted arylsulfonylamino group, the substituted aralkyl group, and the substituted aralkylamino group may be 1 to 3 groups for each selected from a nitro group, an amino group, a cyano group, a halogen atom, a hydroxyl group, a lower alkyl group which may be substituted with a halogen atom, a lower alkenyl group, a lower alkoxy group which may be substituted with 1 to 3 hydroxyl groups, a lower alkylthio group, an aryl group, a di(lower alkyl)amino group, a heterocyclic group, a lower alkylsulfonyl group, and the like. The halogen atom, the lower alkyl group, the lower alkenyl group, the lower alkoxy group, the lower alkylthio group, the aryl group, the di(lower alkyl)amino group, the heterocyclic group, and the lower alkylsulfonyl group are as defined above, respectively.

The pharmaceutically acceptable salt of the compound (I) includes pharmaceutically acceptable acid addition salts, metal salts, ammonium salts, organic amine addition salts and amino acid addition salts.

The pharmaceutically acceptable acid addition salts of the compound (I) include inorganic acid salts, such as a hydrochloride, a sulfate, a nitrate, and a phosphate; and organic acid salts, such as an acetate, a maleate, a fumarate, and a citrate. The pharmaceutically acceptable metal salts include alkali metal salts, such as a sodium salt and a potassium salt; alkaline earth metal salts, such as a magnesium salt and a calcium salt; an aluminum salt; and a zinc salt. The pharmaceutically acceptable ammonium salts include ammonium and tetramethylammonium. The pharmaceutically acceptable organic amine addition salts include addition salts with morpholine, piperidine, etc. The pharmaceutically acceptable amino acid addition salts include addition salts with glycine, phenylalanine, lysine, aspartic acid, glutamic acid, etc.

Production Process 1

Compound (Ia), which is the compound (I) wherein X is a bond, can be produced according to the following step:

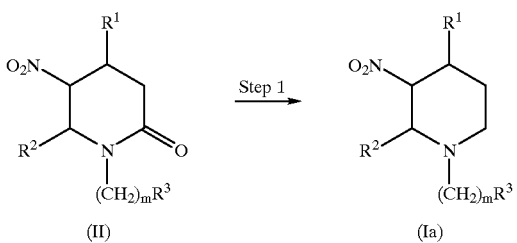

(wherein m, $R^1$, $R^2$, and $R^3$ are as defined above, respectively)

Step 1

The compound (Ia) can be prepared by treating a compound (II) with 1 to 20 equivalents of a reducing agent in an inert solvent. Any reducing agent that reduces an amide into an amine can be used. Examples of the reducing agent include sodium borohydride, lithium aluminum hydride, diisobutyl aluminum hydride, and a borane dimethyl sulfide complex. The inert solvent includes water, methanol, ethanol, chloroform, tetrahydrofuran, dimethylformamide (DMF), and the like. The reaction is carried out at a temperature between −80° C. and the boiling point of the solvent used, and terminates in 5 minutes to 24 hours.

Production Process 2

The starting compound (II) for the Step 1 can be produced from a compound (III), which is known or easily synthesized by a known process, through a compound (IV), for example, according to the following steps with reference to known processes (*Synthesis*, 615 (1976)).

(wherein m, $R^1$, $R^2$, and $R^3$ are as defined above, respectively)

Step 2

The compound (IV) can be prepared by allowing the compound (III) to react with 1 to 100 equivalents of nitromethane in a solvent inert to the reaction, such as acetonitrile or DMF, in the presence of 0.01 to 10 equivalents of a base, such as 1,8-diazabicyclo[5.4.0]undec-7-ene (DBU) in a manner similar to a known process (*Synthesis*, 226 (1984)). The reaction is usually carried out at a temperature between −30 to 100° C., and terminates in 1 to 72 hours. In this step, nitromethane can also serve as a solvent.

Step 3

The compound (II) can be prepared by allowing the compound (IV) to react with $$R^2—CHO \quad (V)$$

(wherein $R^2$ is as defined above) and $$R^3—(CH_2)_m—NH_2 \quad (VI)$$

(wherein m and $R^3$ are as defined above, respectively) in a solvent, such as ethanol or methanol. The compound (V) and the compound (VI) are each usually used in an amount of 1 to 5 equivalents to the compound (IV). An acid addition salt, such as an acetate, of the compound (VI) can also be used in place of the compound (VI). The reaction is usually carried out at a temperature between 0° C. and 100° C., and terminates in 1 to 72 hours.

Production Process 3

Compound (Ic), which is the compound (I) wherein m is an integer of 1 to 5, and X is a bond, can also be produced from compound (Ib), which is the compound (I) wherein m is 0, $R^3$ is a hydrogen atom, and X is a bond, according to the following step:

(wherein n represents an integer of 0 to 4; and $R^1$, $R^2$, and $R^3$ are as defined above, respectively)

Step 4

The compound (Ic) can be prepared by allowing the compound (Ib) and $$R^3—(CH_2)_nCHO \quad (VII)$$

(wherein n and $R^3$ are as defined above, respectively) to react in the presence of 1 to 20 equivalents of a reducing agent in an inert solvent. Any reducing agent that reduces an imine into an amine can be used. Examples of the reducing agent include sodium triacetoxyborohydride, sodium borohydride, lithium aluminum hydride, diisobutylaluminum hydride, and a borane dimethyl sulfide complex. The inert solvent includes methanol, ethanol, chloroform, tetrahydrofuran, DMF, acetic acid, and the like. The reaction is carried out at a temperature between −80° C. and the boiling point of the solvent used and terminates in 5 minutes to 24 hours.

Production Process 4

Compound (Id), which is the compound (I) wherein $R^3$ is a substituted or unsubstituted lower alkyl group, a substituted or unsubstituted aryl group or a substituted or unsubstituted heterocyclic group or wherein $R^3$ is a hydrogen atom, and X is CO, can be produced from the compound (Ib) according to the following step:

(wherein $R^{3a}$ represents a hydrogen atom, a substituted or unsubstituted lower alkyl group, a substituted or unsubstituted aryl group, or a substituted or unsubstituted heterocyclic group; and m, $R^1$, $R^2$ and X are as defined above, respectively, with the proviso that $R^{3a}$ is not a hydrogen atom when X is a bond).

Step 5

The compound (Id) can be prepared by allowing the compound (Ib) and $$R^{3a}—(CH_2)_m—X—Y \quad (VIII)$$

(wherein m, $R^{3a}$, and X are as defined above, respectively; and Y represents a halogen atom, a lower alkylsulfonyloxy group, or an arylsulfonyloxy group which may be substituted with a lower alkyl group; the halogen atom, the lower alkylsulfonyloxy group and the lower alkyl group have the same meanings as described above, respectively, and the aryl moiety of the arylsulfonyloxy group has the same meaning as the above-described aryl group) to react in the presence of 1 to 20 equivalents of an appropriate base in an inert solvent. The base includes triethylamine, pyridine, diisopropylamine, DBU, potassium tert-butoxide, sodium hydride, and the like. The inert solvent includes methylene chloride, tetrahydrofuran, DMF, and the like. The reaction is carried out at a temperature between −80° C. and the boiling point of the solvent used and terminates in 5 minutes to 24 hours.

The compound (Id) can also be prepared by allowing the compound (Ib) and $$R^{3a}-(CH_2)_m-X-OH \qquad (IX)$$

(wherein m, $R^{3a}$, and X are as defined above, respectively) to react in the presence of 1 to 20 equivalents of an appropriate condensing agent in an inert solvent. The inert solvent includes methylene chloride, tetrahydrofuran, DMF, and the like. Where X in compounds (Id) and (IX) is a bond, any condensing agent that serves for the condensation of an alcohol and an amine can be used. Such condensing agents include a combination of diethyl azodicarboxylate, di-tert-butyl azodicarboxylate, or the like; and triphenylphosphine, tributylphosphine, or the like. Where X in compounds (Id) and (IX) is CO, any condensing agent that serves for the condensation of a carboxylic acid and an amine can be used. Such condensing agents include 1-(3-dimethylaminopropyl)-3-ethylcarbodiimide hydrochloride, N,N-dicyclohexylcarbodiimide, 2-chloro-1-methylpyridinium iodide, carbonyldiimidazole, ethyl chloroformate, and the like. If necessary, the reaction can also be accelerated by addition of 1 to 20 equivalents of a base, such as 4-dimethylaminopyridine, diisopropylethylamine, triethylamine or pyridine. The reaction is carried out at a temperature between −80° C. and the boiling point of the solvent used and terminates in 5 minutes to 24 hours.

In the preparation of the compound (I), the conversion of the functional groups in $R^1$, $R^2$ and $R^3$ can be carried out by using methods for converting functional groups commonly employed in synthetic organic chemistry described, e.g., in R. C. Larock, *Comprehensive Organic Transformations* (1989).

Isolation and purification of the products obtained in the above-described production processes can be performed by an appropriate combination of means generally used in organic syntheses, such as filtration, extraction, washing, drying, concentration, crystallization, and various chromatography techniques.

Some of the compound (I) embrace various stereoisomers such as enantiomers and diastereomers. These and all the other possible isomers and mixtures thereof are included within the scope of the present invention.

Some of the compound (I) and the pharmaceutically acceptable salts thereof may exist in the form of an adduct with water or various solvents, which are also included within the scope of the present invention.

Structures and physical properties of the typical examples of the compounds (I) obtained in the present invention are shown in Tables 1 to 6.

TABLE 1

(I)-1

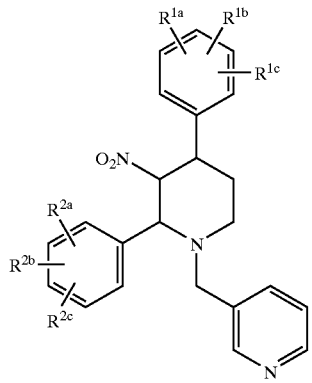

| Compound No. | $R^{1a}$, $R^{1b}$, $R^{1c}$ | $R^{2a}$, $R^{2b}$, $R^{2c}$ | MS m/z (M + H)$^+$ |
|---|---|---|---|
| 1[a] | 2-Br | 4-OH | 470, 468 |
| 2[b] | 2-Br | 4-OH | 470, 468 |
| 3[c] | 2-Br | 4-OH | 470, 468 |
| 4[d] | 2-Br | 4-OH | 470, 468 |
| 5[e] | 2-Br | 4-OH | 470, 468 |
| 6 | 2-CH=CHCH$_3$ | 4-OH | 430 |
| 7 | 2-SCH$_3$ | 4-OH | 436 |
| 8 | 2-Br, 4-CH$_3$ | 4-OH | 485, 483 |
| 9 | 2,4-(CH$_3$)$_2$ | 4-OH | 418 |
| 10 | 2-Cl | 4-OH | 424 |
| 11[a] | 2-Br | 3,4-(OH)$_2$ | 486, 484 |
| 12[b] | 2-Br | 3,4-(OH)$_2$ | 486, 484 |
| 13[c] | 2-Br | 3,4-(OH)$_2$ | 486, 484 |
| 14[d] | 2-Br | 3,4-(OH)$_2$ | 486, 484 |
| 15 | 2-I | 3,4-(OH)$_2$ | 532 |
| 16 | 2-CH$_2$CH$_3$ | 3,4-(OH)$_2$ | 434 |

TABLE 1-continued (I)-1

| Compound No. | $R^{1a}, R^{1b}, R^{1c}$ | $R^{2a}, R^{2b}, R^{2c}$ | MS m/z $(M + H)^+$ |
|---|---|---|---|
| 17 | 2-CH$_2$OCH$_2$CH$_2$OH | 3,4-(OH)$_2$ | 480 |
| 18 | 2-CH(—OCH$_2$CH$_2$O—) | 3,4-(OH)$_2$ | 478 |
| 19 | 2-CH$_2$OH | 3,4-(OH)$_2$ | 436 |
| 20 | 2-CHO | 3,4-(OH)$_2$ | 434 |
| 21 | 2-CH(—SCH$_2$CH$_2$S—) | 3,4-(OH)$_2$ | 510 |
| 22 | 2-CH(—OCH$_3$)$_2$ | 3,4-(OH)$_2$ | 480 |
| 23 | 2-CH=CH$_2$ | 3,4-(OH)$_2$ | 431 |
| 24 | 2-CH(OH)CH$_2$CH$_3$ | 3,4-(OH)$_2$ | 464 |
| 25 | 2,6-Cl$_2$ | 3,4-(OH)$_2$ | 474 |
| 26 | 2,5-Cl$_2$ | 3,4-(OH)$_2$ | 474 |
| 27 | 2,3,5-Cl$_3$ | 3,4-(OH)$_2$ | 510, 508 |
| 28 | 3,5-Br$_2$ | 3,4-(OH)$_2$ | 566, 564, 562 |
| 29 | 2-Br | H | 454, 452 |
| 30[a)] | 2-Br | 3,4-[OCOCH(CH$_3$)$_2$]$_2$ | 626, 624 |
| 31[b)] | 2-Br | 3,4-[OCOCH(CH$_3$)$_2$]$_2$ | 626, 624 |
| 32[c)] | 2-Br | 3,4-[OCOCH(CH$_3$)$_2$]$_2$ | 626, 624 |
| 33[a)] | 2-Br | 3-OCH$_3$, 4-OCOCH(CH$_3$)$_2$ | 570, 568 |
| 34[f)] | 2-Br | 3-OCH$_3$, 4-OCOCH(CH$_3$)$_2$ | 570, 568 |
| 35[f)] | 2-Br | 3-OCH$_3$, 4-OCOCH(CH$_3$)$_2$ | 570, 568 |
| 36 | 2-Br | 3,4-(OCH$_3$)$_2$ | 514, 512 |
| 37 | 2-Br | 4-OCON(CH$_3$)$_2$ | 541, 439 |
| 38 | 2-Br | 4-OCOC$_{11}$H$_{23}$ | 652, 650 |
| 39 | 2-Br | 4-OSO$_2$CF$_3$ | 602, 600 |
| 40 | 2-Br | 4-OCH$_3$ | 484, 482 |
| 41 | 2-Br | 4-OCH$_2$C(CH$_3$)=CH$_2$ | 523, 521 |
| 42 | 2-Br | 3,4-[NHCOOC(CH$_3$)$_3$]$_2$ | 684, 682 |
| 43 | 2-Br | 3,4-[NHCOOCH$_3$]$_2$ | 600, 598 |
| 44 | 2-Br | 3,4-[—NHCONH—] | 510, 508 |
| 45 | 2-Br | 3-NO$_2$, 4-OH | 515, 513 |
| 46 | 2-Br | 3-NH$_2$, 4-OH | 485, 483 |
| 47 | 2-Br | 3-NHSO$_2$CH$_3$, 4-OSO$_2$CH$_3$ | 641, 639 |
| 48 | 2-Br | 3-NHSO$_2$CH$_3$, 4-OH | 563, 561 |
| 49 | 2-Br | 4-NHSO$_2$C$_2$H$_5$, 3-OSO$_2$C$_2$H$_5$ | 668, 666 |
| 50 | 2-Br | 3-NHSO$_2$C$_2$H$_5$, 4-OH | 577, 575 |
| 51 | 2-Br | 3-NHSO$_2$C$_6$H$_5$, 4-OH | 624, 622 |
| 52 | 2-Br | 3-NHSO$_2$ (p-CH$_3$C$_6$H$_4$), 4-OH | 638, 636 |
| 53 | 2-Br | 3-NHCO$_2$CH$_3$, 4-OCO$_2$CH$_3$ | 601, 599 |
| 54 | 2-Br | 3-NHCO$_2$CH$_3$, 4-OH | 543, 541 |
| 55 | 2-Br | 3-NHCO$_2$CH$_2$CH(CH$_3$)$_2$, 4-OH | 585, 583 |
| 56 | 2-Br | 3-NHCOCH$_3$, 4-OCOCH$_3$ | 569, 567 |
| 57 | 2-Br | 3-NHCOCH$_3$, 4-OH | 527, 525 |
| 58 | 2-Br | 3-NHCOC$_4$H$_9$, 4-OH | 568, 566 |
| 59 | 2-Br | 3-NHCOCH(CH$_3$)$_2$ | 555, 553 |
| 60 | 2-Br | 3-NHCH(CH$_3$)$_2$, 4-OH | 527, 525 |
| 61 | 2-Br | 3-C≡CCH$_2$N(CH$_3$)$_2$, 4-OH | 551, 549 |
| 62 | 2-Br | 3,5-(CH$_3$)$_2$, 4-OH | 498, 496 |
| 63 | 2-Br | 3-I, 4-OCH$_2$OCH$_3$ | 639, 637 |
| 64 | 2-Br | 3-I, 4-OH | 595, 593 |
| 65[a)] | 2-Br | 3-OCH$_3$, 4-OH | 500, 498 |
| 66[b)] | 2-Br | 3-OCH$_3$, 4-OH | 500, 498 |
| 67[c)] | 2-Br | 3-OCH$_3$, 4-OH | 500, 498 |
| 68 | 2-Br | 3-NHCH$_2$CH$_3$, 4-OH | 513, 511 |
| 69 | 2-Br | 4-OSO$_2$NH$_2$ | 549, 547 |

TABLE 1-continued

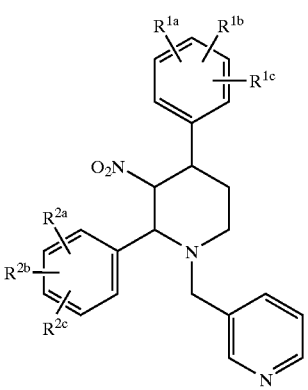

(I)-1

| Compound No. | $R^{1a}, R^{1b}, R^{1c}$ | $R^{2a}, R^{2b}, R^{2c}$ | MS m/z $(M + H)^+$ |
|---|---|---|---|
| 70 | 2-Br | 3-NHCONH$_2$, 4-OCONH$_2$ | 571, 569 |
| 71 | 2-Br | 3-NHCONH$_2$, 4-OH | 528, 526 |
| 72 | 2-Br | 3-NHSO$_2$NH$_2$, 4-OSO$_2$NH$_2$ | 643, 641 |
| 73 | 2-Br | 3-NHSO$_2$NH$_2$, 4-OH | 564, 562 |
| 74 | 2-Br | 2-NH$_2$ | 469, 467 |
| 75 | 2-Br | 3-NO$_2$ | 499, 497 |
| 76 | 2-Br | 3-NH$_2$ | 469, 467 |
| 77 | 2-Br | 3-NHSO$_2$NH$_2$ | 548, 546 |
| 78 | 2-CH$_2$CH$_3$ | 4-OH | 418 |
| 79 | 2-CH$_2$CH$_3$ | 3-NO$_2$, 4-OH | 463 |
| 80 | 2-CH$_2$CH$_3$ | 3-NH$_2$, 4-OH | 433 |
| 81 | 2-CH$_2$CH$_3$ | 3-NHCOCH$_3$, 4-OH | 475 |
| 82 | 2-CH$_2$CH$_3$ | 3-NHCONH$_2$, 4-OH | 476 |
| 83 | 2-CH$_2$CH$_3$ | 3,5-(OCH$_3$)$_2$, 4-OH | 478 |
| 84 | 2-CH$_2$CH$_3$ | 3-NHSO$_2$NH$_2$, 4-OH | 512 |
| 85 | 2-CH$_2$CH$_3$ | 3-NHSO$_2$CH$_3$, 4-OH | 511 |
| 86 | 2-CH$_2$CH$_3$ | 3-I, 4-OCH$_2$OCH$_3$ | 588 |
| 87 | 2-CH$_2$CH$_3$ | 3-CH=CH$_2$, 4-OH | 444 |
| 88 | 2-CH$_2$CH$_3$ | 3-CH=CHSO$_2$CH$_3$, 4-OH | 522 |
| 89 | 2-CH$_2$CH$_3$ | 3-CH$_2$CH$_3$, 4-OH | 466 |
| 90 | 2-Cl | 3-NH$_2$, 4-OH | 439 |
| 91 | 2-Cl | 3-NHCONH$_2$, 4-OH | 482 |
| 92 | 2-CH$_2$CH$_3$ | 3-NHCOOCH$_3$, 4-OH | 491 |
| 93 | 2-Br | 3-N(CH$_3$)$_2$, 4-OH | 513, 511 |
| 94 | 3-Br | 4-OH | 470, 468 |
| 95 | 2-Br | 4-PO(OCH$_2$CH$_3$)$_2$ | 590, 588 |
| 96 | 2-Br | 4-PO(OH)$_2$ | 534, 532 |

[a] (±)-form;
[b] (+)-form;
[c] (−)-form;
[d] (±)-2 hydrochloride;
[e] (±)-2 methane sulfonate;
[f] Optically resolved compound TABLE 2
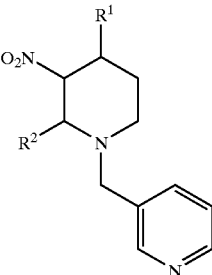
(I)-2
| Compound No. | R¹ | R² | MS m/z (M + H)⁺ |
|---|---|---|---|
| 97 | 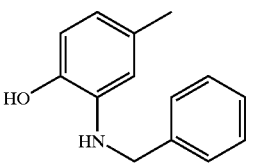 | 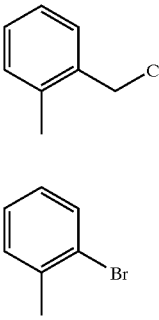 | 523 |
| 98[a)] | 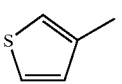 | 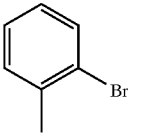 | 460, 458 |
| 99[b)] | 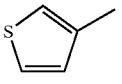 | 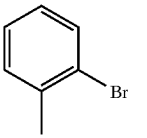 | 460, 458 |
| 100[c)] | 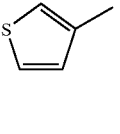 | 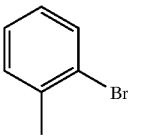 | 460, 458 |
| 101 | 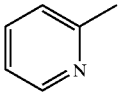 | 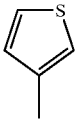 | 455, 453 |
| 102 | 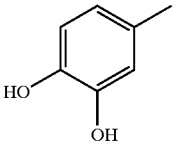 | 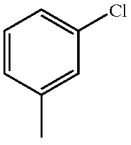 | 412 |
| 103 | 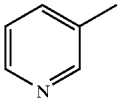 | 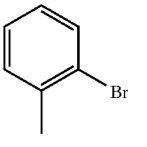 | 409 |
| 104 | 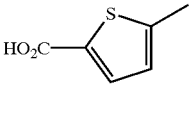 | | 502 |

TABLE 2-continued
(I)-2
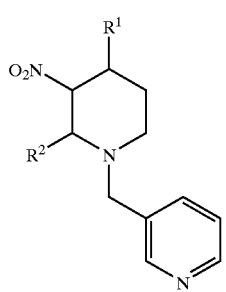
| Compound No. | R¹ | R² | MS m/z (M + H)⁺ |
|---|---|---|---|
| 105 | 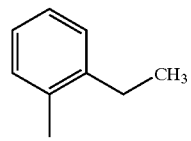 | 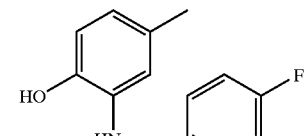 | 541 |
| 106 | 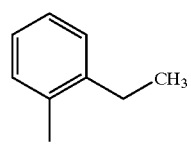 | 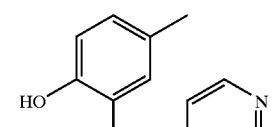 | 524 |
| 107 | 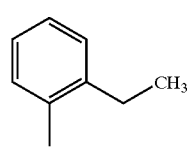 | 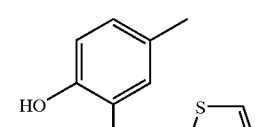 | 541 |
| 108 | 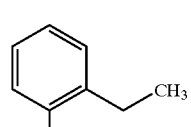 | 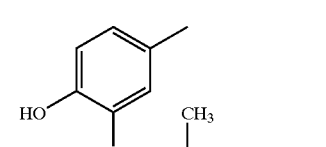 | 517 |
| 109 | 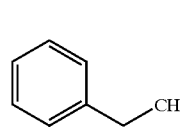 | 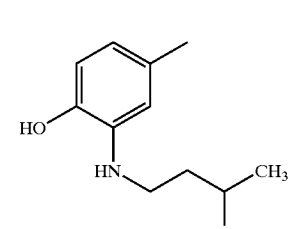 | 503 |
| 110 | 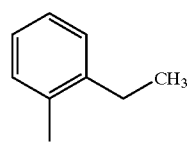 | 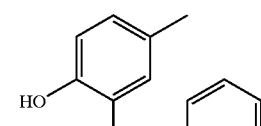 | 524 |

TABLE 2-continued
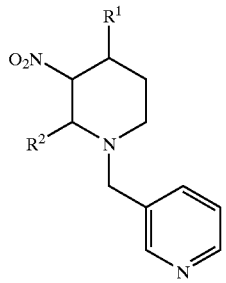
(I)-2
| Compound No. | R¹ | R² | MS m/z (M + H)⁺ |
|---|---|---|---|
| 111 | 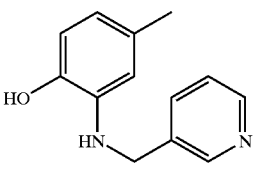 | 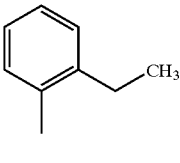 | 524 |
| 112 | 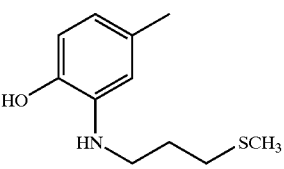 | 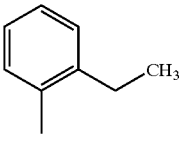 | 507 |
| 113 | 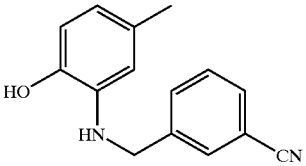 | 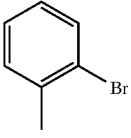 | 548 |
| 114 | 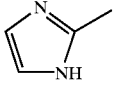 | 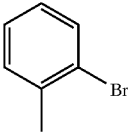 | 444, 442 |
| 115 | 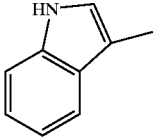 | 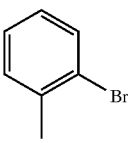 | 493, 491 |
| 116 | 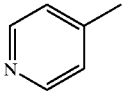 | 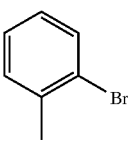 | 455, 453 |
| 117 | 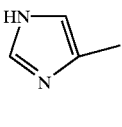 | | 444, 442 |

TABLE 2-continued
(I)-2
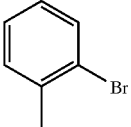
| Compound No. | R¹ | R² | MS m/z (M + H)⁺ |
|---|---|---|---|
| 118 | 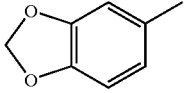 | 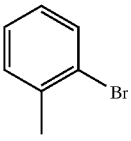 | 498, 496 |
| 119 | 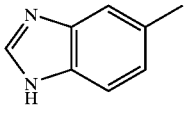 | 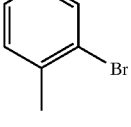 | 494, 492 |
| 120 | 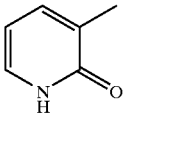 | 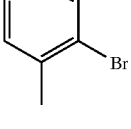 | 471, 469 |
| 121 | 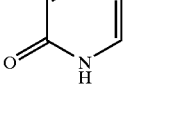 | 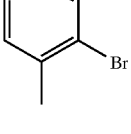 | 471, 469 |
| 122 | 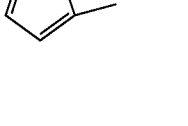 | 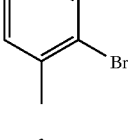 | 460, 458 |
| 123 | 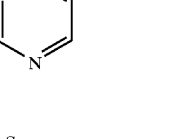 | 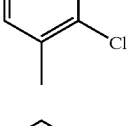 | 455, 453 |
| 124 | 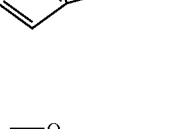 | 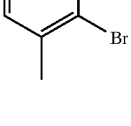 | 414 |
| 125 | 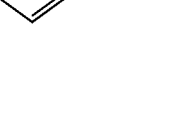 | | 444, 442 |

TABLE 2-continued (I)-2

| Compound No. | R¹ | R² | MS m/z (M + H)⁺ |
|---|---|---|---|
| 126 | 2-bromo-5-methylthiophene | 4-hydroxyphenyl | 476, 474 |
| 127 | 2-bromo-5-methylthiophene | 4-methylthiophen-3-yl | 466, 464 |
| 128[a)] | 2-ethylphenyl (CH₃) | 4-methylthiophen-3-yl | 408 |
| 129[b)] | 2-ethylphenyl (CH₃) | 4-methylthiophen-3-yl | 408 |
| 130[c)] | 2-ethylphenyl (CH₃) | 4-methylthiophen-3-yl | 408 |
| 131 | 2,3-dimethylthiophene | 4-methylthiophen-3-yl | 414 |
| 132 | 2,3-dimethylthiophene | 4-hydroxyphenyl | 410 |
| 133 | 3-bromo-2-methylthiophene | 4-methylthiophen-3-yl | 466, 464 |

TABLE 2-continued
(I)-2
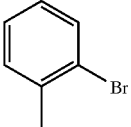
| Compound No. | R¹ | R² | MS m/z (M + H)⁺ |
|---|---|---|---|
| 134 | 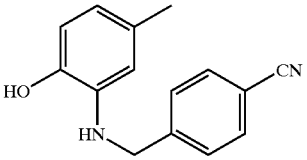 | 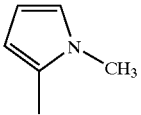 | 600, 598 |
| 135 | 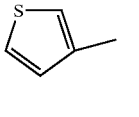 | 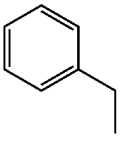 | 383 |
| 136 | 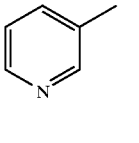 | 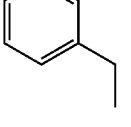 | 389 |
| 137 | 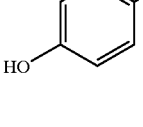 | 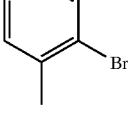 | 404 |
| 138 |  | 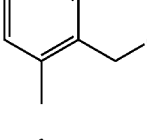 | 444, 442 |
| 139 | 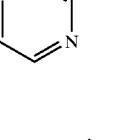 | 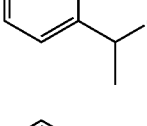 | 403 |
| 140 | 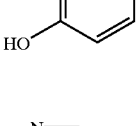 | 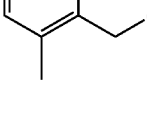 | 418 |
| 141 | 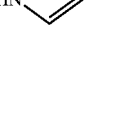 | | 392 |

TABLE 2-continued
(I)-2
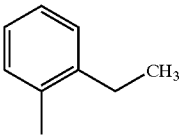
| Compound No. | R¹ | R² | MS m/z (M + H)⁺ |
|---|---|---|---|
| 142 | 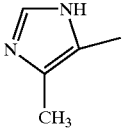 | 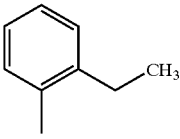 | 406 |
| 143 | 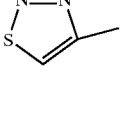 | 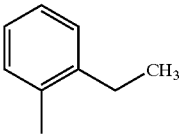 | 410 |
| 144 | 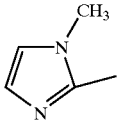 | 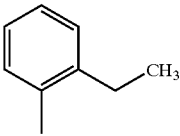 | 406 |
| 145 | 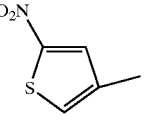 | 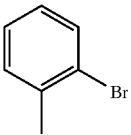 | 453 |
| 146 | 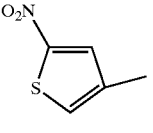 | 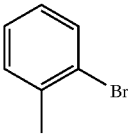 | 505, 503 |
| 147 | 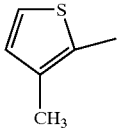 | | 474, 472 |

TABLE 2-continued
(I)-2
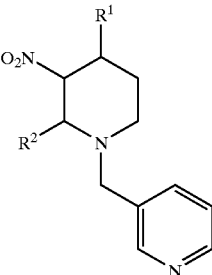
| Compound No. | R¹ | R² | MS m/z (M + H)⁺ |
|---|---|---|---|
| 148 | | | 474 |
| 149 | 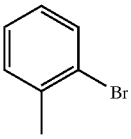 | 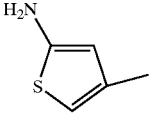 | 515 |
| 150 | 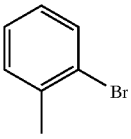 | 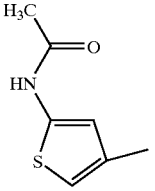 | 516 |
| 151 | 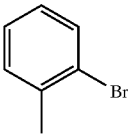 | 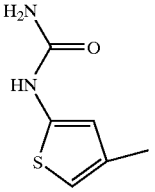 | 420 |
| | 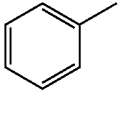 | 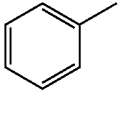 | |
a): (±)-form;
b): (+)-form;
c): (−)-form

TABLE 3

(I)-3

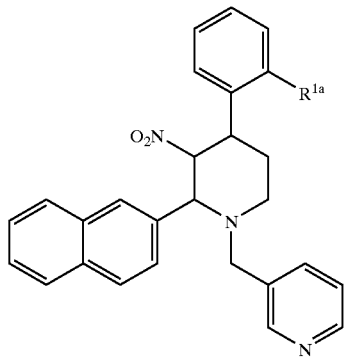

| Compound No. | $R^{1a}$ | MS m/z $(M + H)^+$ |
|---|---|---|
| 152 | Br | 504, 502 |
| 153 | $CH_2CH_3$ | 452 |
| 154 | $CH_3$ | 438 |

TABLE 4

(I)-4

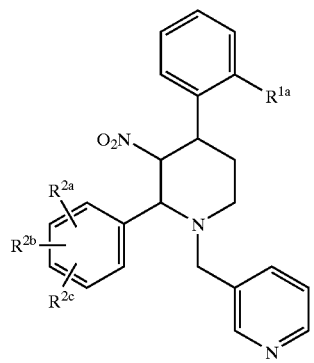

| Compound No. | $R^{1a}$ | $R^{2a}, R^{2b}, R^{2c}$ | MS m/z $(M + H)^+$ |
|---|---|---|---|
| 155 | $CH_3$ | H | 388 |
| 156[a)] | $CH_2CH_3$ | H | 402 |

TABLE 4-continued (I)-4

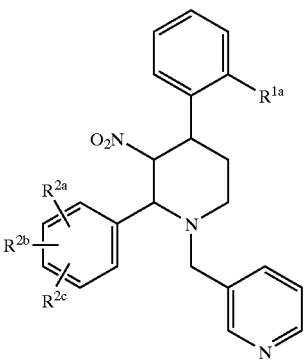

| Compound No. | $R^{1a}$ | $R^{2a}, R^{2b}, R^{2c}$ | MS m/z $(M + H)^+$ |
|---|---|---|---|
| 157[b)] | $CH_2CH_3$ | H | 402 |
| 158[c)] | $CH_2CH_3$ | H | 402 |
| 159 | Br | 3-$OCH_2CH_3$, 4-OH | 514, 512 |
| 160 | $CH_2CH_3$ | 3-$OCH_2CH_3$, 4-OH | 462 |
| 161 | Br | 3-$CH_3$, 4-OH | 484, 482 |
| 162 | $CH_2CH_3$ | 3-$CH_3$, 4-OH | 432 |
| 163 | Br | 2-OH, 3-$OCH_3$ | 500, 498 |
| 164 | $CH_2CH_3$ | 4-OH, 3,5-$(CH_3)_2$ | 446 |
| 165 | Br | 4-OH, 3,5-$(OCH_3)_2$ | 530, 528 |
| 166 | $CH_2CH_3$ | 3-$OCH_3$, 4-OH | 448 |
| 167 | Br | 2-OH, 3-$OCH_3$, 5-Br | 580, 578, 576 |
| 168 | $CH_2CH_3$ | 4-$C_4H_9$ | 458 |
| 169 | Br | 4-$SCH_3$ | 500, 498 |
| 170 | $CH_2CH_3$ | 4-$SCH_3$ | 448 |
| 171 | $CH_2CH_3$ | 3-Cl, 4-F | 454 |
| 172 | $CH_2CH_3$ | 4-$CF_3$ | 470 |
| 173 | $CH_2CH_3$ | 4-$CH(CH_3)_2$ | 496, 494 |
| 174 | Br | 4-$CH(CH_3)_2$ | 444 |
| 175 | Br | 2-$OCH_2CH_3$ | 498, 496 |
| 176 | $CH_2CH_3$ | 2-$OCH_2CH_3$ | 446 |
| 177 | Br | 2,4,5-$(OCH_3)_3$ | 544, 542 |
| 178 | Br | 2,3-$(OCH_3)_2$ | 514, 512 |
| 179 | $CH_2CH_3$ | 2,3-$(OCH_3)_2$ | 462 |
| 180 | Br | 4-$C_6H_5$ | 530, 528 |
| 181 | Br | 4-$OC_6H_5$ | 546, 544 |
| 182 | Br | 2-$OCH_3$ | 484, 482 |
| 183 | Br | 4-$B(OH)_2$ | 498, 486 |

[a)]: (±)-form;
[b)]: (+)-form;
[c)]: (−)-form

TABLE 5
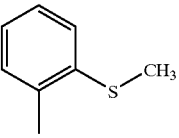
(I)-5
| Compound No. | R¹ | R² | MS m/z (M + H)⁺ |
|---|---|---|---|
| 184 | 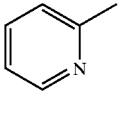 | 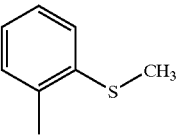 | 421 (ESI) |
| 185 | 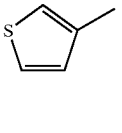 | 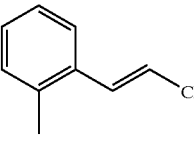 | 426 (ESI) |
| 186 | 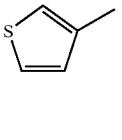 | 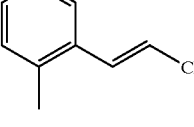 | 410 (ESI) |
| 187 | 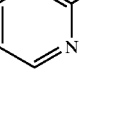 | 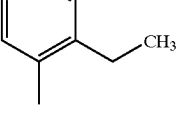 | 415 (ESI) |
| 188 | 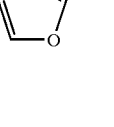 | 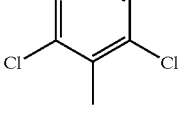 | 392 (ESI) |
| 189 | 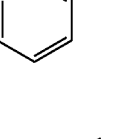 | 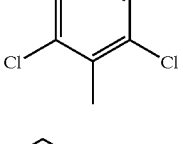 | 442 (ESI) |
| 190 | 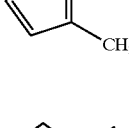 | 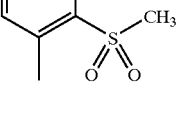 | 462 (FAB) |
| 191 |  | | 458 (ESI) |

TABLE 5-continued
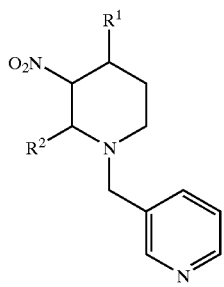
(I)-5
| Compound No. | R¹ | R² | MS m/z (M + H)⁺ |
|---|---|---|---|
| 192 | 2-(methylsulfinyl)methylphenyl | 3-thienyl | 442 (ESI) |
| 193[a] | 2-bromophenyl | 3-thienyl | 460, 458 (ESI) |
| 194[a] | 2-bromophenyl | 2-pyridyl | 455, 453 (ESI) |
| 195[a] | 2-bromophenyl | phenyl | 454, 452 (ESI) |
| 196[b] | 2-ethylphenyl | phenyl | 402 (ESI) |
| 197[b] | 2-methylphenyl | phenyl | 388 (FAB) |
| 198[b] | 2-bromophenyl | 2-hydroxy-5-methyl-3-(isobutyrylamino)phenyl | 555, 553 (FAB) |

TABLE 5-continued (I)-5

[Structure: piperidine ring with R¹ at 4-position, O₂N at 3-position, R² at 2-position, and N-CH₂-(3-pyridyl) at 1-position]

| Compound No. | R¹ | R² | MS m/z (M + H)⁺ |
|---|---|---|---|
| 199[b)] | 2-ethylphenyl (with CH₃) | 2-methylpyridin-yl | 403 (FAB) |
| 200[b)] | 2-(methylthio)phenyl (with CH₃) | 2-methylpyridin-yl | 421 (FAB) |
| 201[b)] | 2-bromophenyl | 4-hydroxy-3-(methoxycarbonylamino)-phenyl with CH₃ | 543, 541 (ESI) |
| 202[a)] | 2-bromophenyl | 4-hydroxy-3-(ethylsulfonylamino)phenyl with CH₃ | 577, 575 (FAB) |
| 203[a)] | 2-ethylphenyl (with CH₃) | 4-hydroxy-3-(methylsulfonylamino)phenyl with CH₃ | 511 (ESI) |
| 204[a)] | 2-ethylphenyl (with CH₃) | 4-hydroxy-3-((pyridin-2-ylmethyl)amino)phenyl with CH₃ | 524 (ESI) |

TABLE 5-continued
(I)-5
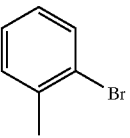
| Compound No. | R¹ | R² | MS m/z (M + H)⁺ |
|---|---|---|---|
| 205 [(−)-Compound 101] | 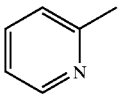 | 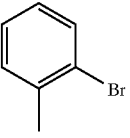 | 455, 453 (FAB) |
| 206 [(+)-Compound 101] | 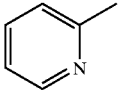 | 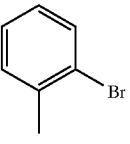 | 455, 453 (FAB) |
| 207<sup>c)</sup> | 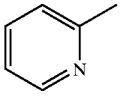 | 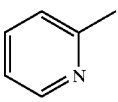 | 455, 453 (FAB) |
a): (±)-2 hydrochloride;
b): (±)-hydrochloride;
c): (+)-2 hydrochloride
TABLE 6
(I)-6
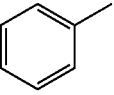
| Compound No. | X(CH₂)ₘR³ | R² | MS m/z (M + H)⁺ |
|---|---|---|---|
| 208 | H |  | 364, 362 (ESI) |
| 209 | H |  | 426 (ESI) |

TABLE 6-continued
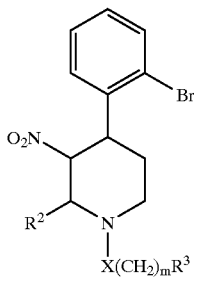
(I)-6
| Compound No. | X(CH$_2$)$_m$R$^3$ | R$^2$ | MS m/z (M + H)$^+$ |
|---|---|---|---|
| 210 | H | 3,4-disubstituted phenyl with OCH$_2$OCH$_3$ and CH$_2$OOCH$_3$ groups | 483, 481 (FAB) |
| 211 | 2-pyridylmethyl | 2-pyridyl | 455, 453 (FAB) |
| 212 | (1H-pyrrol-2-yl)methyl | phenyl | 444, 442 (ESI) |
| 213 | (1,3-dimethylimidazolium-5-yl)methyl iodide | phenyl | 600, 598 (ESI) |
| 214 | 4-cyanobenzyl | 2-pyridyl | 480, 478 (ESI) |
| 215 | (2,3-dichloropyridin-5-yl)methyl | phenyl | 524, 522 (ESI) |
| 216 | 3-cyanobenzyl | 2-pyridyl | 480, 478 (ESI) |

TABLE 6-continued
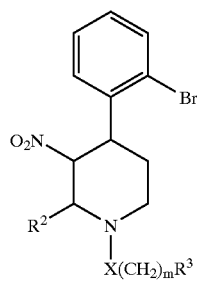
(I)-6
| Compound No. | X(CH₂)ₘR³ | R² | MS m/z (M + H)⁺ |
|---|---|---|---|
| 217 | 4-methyl(1-methylimidazol-4-yl)methyl | phenyl | 458, 456 (FAB) |
| 218 | (1-methylimidazol-5-yl)methyl | phenyl | 458, 456 (ESI) |
| 219 | 3-pyridylcarbonyl | 3,4-bis(methoxymethoxy)phenyl | 588, 586 (ESI) |
| 220 | 3-pyridylcarbonyl | 3,4-dihydroxyphenyl | 500, 498 (ESI) |
| 221 | (3-pyridyl)acetyl | 3,4-bis(methoxymethoxy)phenyl | Not tested |
| 222 | (3-pyridyl)acetyl | 3,4-dihydroxyphenyl | 514, 512 (FAB) |

TABLE 6-continued (I)-6

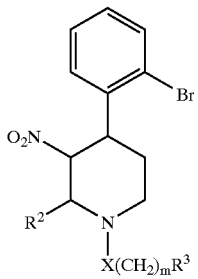

| Compound No. | X(CH$_2$)$_m$R$^3$ | R$^2$ | MS m/z (M + H)$^+$ |
|---|---|---|---|
| 223 | | | 558, 556 (ESI) |

The pharmacological activity of the compound (I) will be demonstrated in Test Examples.

TEST EXAMPLE 1

Proliferation Inhibition Test on Human Colonic Cancer Cells DLD-1

A 96-well microplate (Nunk #167008) was inoculated with 1000 human colonic cancer cells DLD-1 per well and pre-cultured in an RPMI 1640 medium containing 5% or 10% of fetal calf serum (FCS) in a 5% $CO_2$ incubator at 37° C. for 24 hours. A 10 mmol/l solution of each test compound in dimethyl sulfoxide (DMSO) was diluted with the medium for culturing and added to the wells at a serial dilution of ⅓, followed by culturing for 72 hours. After completion of the culturing, the medium was discarded, and to each well was added 50 μl of 3-(4,5-dimethylthiazol-2-yl)-2,5-diphenyltetrazolium bromide (Sigma, hereinafter abbreviated as MTT) dissolved in the medium for culturing in a final concentration of 1 mg/mL. The microplate was incubated in a 5% $CO_2$ incubator at 37° C. for 4 hours, the MTT solution was discarded, and 150 μl/well of DMSO was added to each well, followed by vigorously stirring by means of a plate mixer to completely dissolve the MTT-formazan crystals. The difference between the absorbance at 550 nm and that at 630 nm was measured with a microplate reader SPECTRAmax 250 (Wako Pure Chemical). The cell proliferation inhibitory activity in terms of 50% inhibitory concentration ($IC_{50}$) was calculated by use of the 4-parameter logistic calibration curve of the appended software SOFTmaxPRO. The results obtained are shown in Table 7.

TABLE 7

Proliferation Inhibitory Effect on Human Colonic Cancer Cells DLD-1

| Compound No. | $IC_{50}$ (μmol/L) |
|---|---|
| 1 | 10 |
| 11 | 11 |

TABLE 7-continued

Proliferation Inhibitory Effect on Human Colonic Cancer Cells DLD-1

| Compound No. | $IC_{50}$ (μmol/L) |
|---|---|
| 12 | 15 |
| 37 | 11 |
| 44 | 20 |
| 46 | 19 |
| 48 | 5.5 |
| 54 | 9.7 |
| 56 | 13 |
| 57 | 17 |

TEST EXAMPLE 2

Antitumor Test on Solid Tumor of Human Colonic Cancer Cells DLD-1 Transplanted into Nude Mouse A 2 mm square fragment was cut out of a selected part showing satisfactory proliferation of a tumor lump of human colonic cancer cells DLD-1 which had been subcultured in male nude mice (BALB/c-nu/nu mice, Clea Japan) and transplanted into the subcutaneous site of the abdomen of a 11-week-old male nude mouse with a trocar. When the tumor volume (formula 1) reached 50 to 70 mm$^3$, the test animals were divided into groups each consisting of 5 mice. Each test compound was dissolved in physiological saline containing polyoxyethylene sorbitan monooleate and intraperitoneally administered to the mice twice a day for consecutive 10 days. The antitumor activity of the test compound was obtained as a T/C (%; formula 2) as to the ratio of the tumor volume after administration (V) to the tumor volume before administration (V0), i.e., V/V0.

Tumor volume(mm$^3$)={length(mm)×[breadth(mm)]$^2$}×½ (formula 1)

T/C(%)=[(V/V0 of drug-administered group)/(V/V0 of no drug-administered group)]×100 (formula 2)

The results obtained are shown in Table 8.

TABLE 8

Antitumor Effect on Solid Tumor of Human Colonic Cancer Cells DLD-1 Transplanted into Nude Mouse

| Compound No. | Dose | T/C (%) |
|---|---|---|
| 5 | 10 mg/kg | 50 |
| 14 | 10 mg/kg | 46 |

TEST EXAMPLE 3

Proliferation Inhibition Test on Human Pancreatic Cancer Cells MIA-PaCa2

A 96-well microplate (Nunk #167008) was inoculated with 2000 human pancreatic cancer cells MIA-PaCa2 per well and pre-cultured in an RPMI 1640 medium containing 10% of fetal calf serum (FCS) in a 5% $CO_2$ incubator at 37° C. for 24 hours. A 10 mmol/l solution of each test compound in dimethyl sulfoxide (DMSO) was diluted with the medium for culturing and added to the wells at a serial dilution of ⅓, followed by culturing for 72 hours. After completion of the culturing, the medium was discarded, and to each well was added 50 µl of MTT dissolved in the medium for culturing in a final concentration of 1 mg/mL. The microplate was incubated in a 5% $CO_2$ incubator at 37° C. for 4 hours, the MTT solution was discarded, and 150 µl/well of DMSO was added to each well, followed by vigorously stirring by means of a plate mixer to completely dissolve the MTT-formazan crystals. The difference between the absorbance at 550 n and that at 630 nm was measured with a microplate reader SPECTRAmax 250 (Wako Pure Chemical). The cell proliferation inhibitory activity in terms of 50% inhibitory concentration ($IC_{50}$) was calculated by use of the 4-parameter logistic calibration curve of the appended software SOFTmaxPRO.

The results obtained are shown in Table 9.

TABLE 9

Proliferation Inhibitory Effect on Human Pancreatic Cancer Cells MIA-PaCa2

| Compound No. | $IC_{50}$ (µmol/L) |
|---|---|
| 1 | 20 |
| 6 | 9.9 |
| 11 | 23 |
| 50 | 6.9 |
| 52 | 9.6 |
| 60 | 6.1 |
| 61 | 15 |
| 63 | 11 |
| 64 | 16 |
| 82 | 10 |
| 105 | 5.1 |
| 106 | 3.4 |
| 107 | 4.0 |
| 109 | 7.1 |
| 152 | 15 |
| 153 | 7.4 |
| 154 | 5.0 |
| 156 | 4.0 |
| 164 | 7.0 |
| 166 | 7.3 |
| 167 | 5.7 |
| 170 | 13 |
| 171 | 8.0 |
| 172 | 11 |

TABLE 9-continued

Proliferation Inhibitory Effect on Human Pancreatic Cancer Cells MIA-PaCa2

| Compound No. | $IC_{50}$ (µmol/L) |
|---|---|
| 178 | 10 |
| 179 | 17 |
| 183 | 16 |

The compound (I) or pharmaceutically acceptable salts thereof can be administered alone as such, but usually these are desirably supplied as various pharmaceutical preparations. These pharmaceutical preparations are to be used for animals and humans.

The pharmaceutical preparations may contain the compound (I) or the pharmaceutically acceptable salt thereof as a sole active ingredient or as a mixture with other arbitrary active ingredients for treatment. The pharmaceutical preparations are prepared by mixing the active ingredients) with one or more pharmaceutically acceptable carriers and processing the mixture in an arbitrary method well-known in the art of pharmaceutics.

The administration route is desirably such that is the most effective for the treatment and includes oral or non-oral (e.g., intravenous) routes.

The dose form includes tablets, powders, granules, syrups, and injections.

Liquid preparations suitable for oral administration, such as syrups, can be prepared by using water, succharides such as sucrose, sorbitol or fructose, glycols such as polyethylene glycol or propylene glycol, oils such as sesame oil, olive oil or soybean oil, antiseptics such as p-hydroxybenzoic acid esters, flavors such as a strawberry flavor or a peppermint flavor, or the like. Tablets, powders, granules and the like can be prepared by using vehicles such as lactose, dextrose, sucrose, or mannitol, disintegrators such as starch or sodium alginate, lubricants such as magnesium stearate or talc, binders such as polyvinyl alcohol, hydroxypropyl cellulose, or gelatin, surfactants such as fatty acid esters, plasticizers such as glycerol, or the like.

Preparations suitable for non-oral administration preferably comprise a sterile aqueous preparation which contains an active compound and is isotonic with the blood of a recipient. In the case of an injection, for instance, an injectable solution is prepared by using a carrier comprising saline, a dextrose solution or a mixture of saline and a dextrose solution, or the like.

One or more than one adjuvants selected from those described as for oral preparations, such as diluents, antiseptics, flavors, vehicles, disintegrators, lubricants, binders, surfactants, plasticizers, etc. can be added to these non-oral preparations.

The dosage and the number of doses of the compound (I) or pharmaceutically acceptable salts thereof vary depending on the form of administration, the age or body weight of a patient, the character or severity of the symptoms to be treated, and the like. In the case of oral administration, a dose of 0.01 mg to 1 g, preferably 0.05 to 50 mg, is usually given to an adult in a single or several divided doses per day. In the case of non-oral administration such as intravenous administration, a dose of 0.001 to 100 mg, preferably 0.01 to 10 mg, is given to an adult in a single or several divided doses per day. These dose levels and numbers of doses are subject to variation according to the above-mentioned various conditions.

The embodiment of the present invention will be illustrated by way of Examples and Reference Examples.

EXAMPLE 1

Synthesis of Compound 1

A borane dimethyl sulfide complex (10.0 mL, 130 mmol) was added to a tetrahydrofuran solution (600 mL) of Compound A (10.0 g, 21 mmol), followed by refluxing for 10 hours. The reaction solution was cooled to room temperature, and methanol was added thereto dropwise to cease the reaction. The reaction solution was concentrated under reduced pressure, and the resulting residue was extracted with chloroform. The extract was washed with a 5% aqueous solution of sodium hydrogencarbonate, and the organic layer was concentrated. The crude product was purified by silica gel column chromatography (eluted with methanol/chloroform=5/95) and recrystallized from methanol to obtain Compound 1 (2.93 g, yield: 30%).

$^1$H-NMR (DMSO-$d_6$, 300 MHz) δ 9.53 (s, 1H), 8.44 (m, 1H), 8.16 (br s, 1H), 7.73 (m, 1H), 7.65–7.56 (m, 2H), 7.40–7.31 (m, 4H), 7.18 (m, 1H), 6.78 (br s, 1H), 6.75 (br s, 1H), 5.34 (dd, J=9.4, 11.7 Hz, 1H), 3.87 (dt, J=4.0, 11.7 Hz, 1H), 3.73 (d, J=9.4 Hz, 1H), 3.59 (d, J=13.9 Hz, 1H), 3.08 (d, J=13.9 Hz, 1H), 2.90 (m, 1H), 2.39 (m, 1H), 1.89–1.67 (m, 2H)

Elemental Analysis: $C_{23}H_{22}BrN_3O_3 \cdot 0.3H_2O$

Calcd. (%): C, 58.31; H, 4.81; N, 8.87

Found (%): C, 58.36; H, 5.02; N, 8.83

EXAMPLE 2

Synthesis of Compound 2 and Compound 3

Compound 4 (200 mg, 0.04 mmol) was optically resolved by high performance liquid chromatography (HPLC) (Chiralcel OD column (diameter: 2 cm; length: 25 cm); eluent: isopropyl alcohol/n-hexane/diethylamine=33/66/0.1; flow rate: 6 mL/min; detection: UV 254 nm). Each of the enantiomers was purified by column chromatography (eluted with methanol/chloroform=5/95) to obtain Compound 2 (36 mg; yield: 18%) and Compound 3 (48 mg; yield: 24%).

Compound 2: $[\alpha]^{26}_D$=+63.9° (c=0.23, methanol)
Compound 3: $[\alpha]^{26}_D$=−68.5° (c=0.20, methanol)

EXAMPLE 3

Synthesis of Compound 4

Compound 1 obtained by treating Compound A (10.0 g, 21 mmol) in a manner similar to that in Example 1 was dissolved in chloroform (300 mL), and a 10% methanol solution (20 mL) of hydrochloric acid was added thereto. The mixture was stirred, followed by concentration under reduced pressure. Recrystallization of the resulting crude hydrochloride from 2-propanol gave Compound 4 (2.87 g; yield: 25%).

$^1$H-NMR (CD$_3$OD, 300 MHz) δ 8.89 (br s, 1H), 8.81 (m, 1H) 8.62 (m, 1H), 8.04 (m, 1H), 7.69–7.57 (m, 4H), 7.40 (m, 1H), 7.18 (m, 1H), 6.82–6.78 (m, 2H), 5.79 (br s, 1H), 4.40–4.15 (m, 4H), 3.62–3.23 (m, 2H), 2.48 (br s, 1H), 2.17 (m, 1H)

EXAMPLE 4

Synthesis of Compound 5

To a tetrahydrofuran (300 mL) solution of Compound 1 (5.00 g, 10.7 mmol) were successively added diisopropyl ether (400 mL) and methanesulfonic acid (1.4 mL, 0.0196 mmol), and the mixture was stirred at room temperature for 1 hour. The precipitated crystals were collected by filtration to obtain Compound 5 (6.06 g; yield: 98%).

$^1$H-NMR (CD$_3$OD, 300 MHz) δ 8.79 (m, 2H), 8.54 (m, 1H), 8.03 (m, 1H), 7.72 (m, 1H), 7.58–7.36 (m, 4H), 7.16 (m, 1H), 6.80 (m, 2H), 5.73 (br s, 1H), 4.38–4.08 (m, 4H), 3.54–3.30 (m, 2H), 2.75 (s, 6H), 2.39–2.10 (m, 2H)

Elemental Analysis: $C_{23}H_{22}BrN_3O_4 \cdot 2CH_3SO_3H \cdot 1.3H_2O$

Calcd. (%): C, 43.90; H, 4.80; N, 6.14

Found (%): C, 43.86; H, 4.75; N, 6.02

EXAMPLE 5

Synthesis of Compound 6

Sodium borohydride (152 mg, 40 mmol) was added to a solution (20 mL) of Compound B (88 mg, 0.20 mmol) in a tetrahydrofuran/water (9/1) mixed solvent under cooling with ice, and the mixture was slowly heated up to 60° C. and stirred at that temperature for 30 minutes. Thereafter, the reaction solution was poured into water, washed with dilute hydrochloric acid, and extracted with a chloroform/methanol (9/1) mixed solvent. The extract was dried over sodium sulfate, and the solvent was removed under reduced pressure. The resulting residue was purified by silica gel column chromatography (eluted with chloroform/methanol= 98/2) to obtain Compound 6 (37 mg; yield: 42%).

$^1$H-NMR (CDCl$_3$, 270 MHz) δ 8.57 (br s, 1H), 8.47 (d, J=5.0 Hz, 1H), 7.57 (d, J=7.6 Hz, 1H), 7.36–7.15 (m, 8H), 6.86 (d, J=8.6 Hz, 2H), 6.68 (d, J=15.9 Hz, 1H), 6.09 (dq, J=15.9, 6.6 Hz, 1H), 4.96(dd, J=10.3, 9.6 Hz, 1H), 3.88–3.72 (m, 3H), 3.10–3.01 (m, 2H), 2.34 (m, 1H), 1.94–1.60 (m, 5H)

EXAMPLE 6

Synthesis of Compound 7

A borane dimethyl sulfide complex (0.760 mL, 15 mmol) was added to a tetrahydrofuran solution (500 mL) of Compound C (900 mg, 2.0 mmol), followed by stirring for 2 hours. Thereafter, the solvent was removed under reduced pressure. The residue was dissolved in methanol (100 mL), and hydrochloric acid (1 mol/l, 20 mL) was added thereto, followed by stirring at 50° C. for 5 hours. The mixture was neutralized with a saturated aqueous solution of sodium hydrogencarbonate and extracted with chloroform, and the extract was dried over sodium sulfate. The solvent was evaporated under reduced pressure. Recrystallization of the resulting residue from chloroform gave Compound 7 (515.9 mg; yield: 57%).

$^1$H-NMR (DMSO-$d_6$, 300 MHz) δ 9.68 (br s, 1H), 8.59 (br s, 2H), 7.86–7.81 (m, 2H), 7.52–7.32 (m, 6H), 6.93 (d, J=8.6 Hz, 2H), 6.93 (d, J=8.6 Hz, 2H), 5.48 (dd, J=10.6, 9.7 Hz, 1H), 4.06 (m, 1H), 3.88 (d, J=9.7 Hz, 1H), 3.76 (d, J=14.2 Hz, 1H), 3.24 (d, J=14.2 Hz, 1H), 3.05 (m, 1H), 2.59 (m, 4H), 2.51 (m, 1H), 2.05–1.86 (m, 2H)

EXAMPLE 7

Synthesis of Compound 8

Compound 8 (67 mg; yield: 54%) was obtained from Compound D (130 mg, 0.2 mmol) and a borane dimethyl sulfide complex (0.25 mL, 2.7 mmol) in a manner similar to that in Example 1.

$^1$H-NMR (CDCl$_3$, 300 MHz) δ 8.59 (br s, 1H), 8.47 (dd, J=4.9, 1.3 Hz, 1H), 7.57 (d, J=7.6 Hz, 1H), 7.35–7.24 (m,

5H), 7.07 (d, J=8.3 Hz, 1H), 6.88 (d, J=8.6 Hz, 2H), 4.97 (dd, J=10.6, 9.6 Hz, 1H), 4.02 (m, 1H), 3.86 (d, J=9.9 Hz, 1H), 3.79 (d, J=9.6 Hz, 1H), 3.07 (d, J=14.2 Hz, 1H), 3.02 (m, 1H), 2.46 (m, 1H), 1.99 (m, 1H), 1.69 (m, 1H)

EXAMPLE 8

Synthesis of Compound 9

Compound 9 (39.6 mg; yield: 41%) was obtained from Compound E (100 mg, 0.23 mmol) and a borane dimethyl sulfide complex (0.25 mL, 2.7 mmol) in a manner similar to that in Example 1.

$^1$H-NMR (CDCl$_3$, 300 MHz) δ 8.47 (br s, 2H), 7.76 (d, J=7.9 Hz, 1H), 7.41 (dd, J=7.6, 6.0 Hz, 1H), 7.27 (d, J=8.2 Hz, 2H), 7.19 (d, J=7.9 Hz, 1H), 7.01 (d, J=7.6 Hz, 1H), 6.94 (br s, 1H), 6.78 (d, J=8.2 Hz, 2H), 4.92 (dd, J=10.7, 9.8 Hz, 1H), 3.79 (d, J=14.5 Hz, 1H), 3.75 (d, J=9.8 Hz, 1H), 3.67 (m, 1H), 3.10 (d, J=14.5 Hz, 1H), 2.97 (m, 1H), 2.45 (m, 1H), 2.29 (s, 3H), 2.25 (s, 3H), 1.92 (m, 1H), 1.65 (m, 1H)

EXAMPLE 9

Synthesis of Compound 10

Compound 10 (134 mg; yield: 63%) was obtained from Compound F (216 mg, 0.5 mmol) and a borane dimethyl sulfide complex (0.14 mL, 1.5 mmol) in a manner similar to that in Example 1.

$^1$H-NMR (DMSO-d$_6$, 300 MHz) δ 9.62 (s, 1H), 8.52 (br s, 2H) 7.86 (d, J=7.3 Hz, 1H), 7.72 (d, J=7.9 Hz, 1H), 7.52–7.31 (m, 6H), 6.85 (d, J=8.6 Hz, 2H), 5.40 (dd, J=10.2, 9.9 Hz, 1H), 4.00 (m, 1H), 3.83 (d, J=9.9 Hz, 1H), 3.68 (d, J=13.9 Hz, 1H), 3.16 (d, J=13.9 Hz, 1H), 2.98 (m, 1H), 2.49 (m, 1H), 1.93–1.84 (m, 2H)

EXAMPLE 10

Synthesis of Compound 11

A borane dimethyl sulfide complex (3.50 mL, 46.0 mmol) was added to a tetrahydrofuran solution (400 mL) of Compound G (3.60 g, 7.24 mmol), followed by refluxing for 10 hours. The reaction solution was cooled to room temperature, and methanol (30 mL) was added thereto dropwise to cease the reaction. The reaction solution was concentrated under reduced pressure, and to the resulting residue was added a 2 mol/l aqueous hydrochloric acid solution (100 mL), followed by stirring at room temperature for 12 hours. The mixture was neutralized with a saturated aqueous sodium hydrogencarbonate solution and extracted with chloroform. The organic layer was concentrated. The crude product was purified by silica gel column chromatography (eluted with methanol/chloroform=5/95) and recrystallized from ethanol to obtain Compound 11 (0.998 g; yield: 29%).

$^1$H-NMR (DMSO-d$_6$, 300 MHz) δ 9.05 (s, 1H), 8.97 (s, 1H), 8.44 (m, 2H), 8.42 (m, 1H), 7.75 (m, 1H), 7.66–7.56 (m, 2H), 7.40–7.32 (m, 2H), 7.17 (m, 1H), 6.94 (br s, 1H), 6.72 (m, 1H), 5.25 (dd, J=9.4, 11.6 Hz, 1H), 3.86 (dt, J=4.0, 11.6 Hz, 1H), 3.64 (d, J=13.8 Hz, 1H), 3.63 (d, J=9.4 Hz, 1H), 3.05 (d, J=13.8 Hz, 1H), 2.88 (m, 1H), 2.36 (m, 1H), 1.86–1.71 (m, 2H)

Elemental Analysis: C$_{23}$H$_{22}$BrN$_3$O$_4$·1.0C$_2$H$_5$OH

Calcd. (%): C, 56.60; H, 5.33; N, 7.92

Found (%): C, 56.38; H, 5.58; N, 7.91

EXAMPLE 11

Synthesis of Compound 12

Water (0.4 mL) and sodium hydrogencarbonate (46 mg, 0.27 mmol) were added to a solution of Compound 31 (34 mg, 0.055 mmol) obtained in Example 28 in methanol (4.0 mL), and the mixture was stirred at room temperature for 9 hours. The reaction mixture was concentrated under reduced pressure, the residue was extracted with chloroform and the extract was washed with water. The organic layer was concentrated under reduced pressure. The crude product was purified by preparative thin layer chromatography (developed with methanol/chloroform=1/99) to obtain Compound 12 (20.3 mg; yield: 76%).

$[\alpha]^{26}_D$=+68.0° (c=0.225, methanol)

EXAMPLE 12

Synthesis of Compound 13

Compound 13 (9.5 mg; yield: 68%) was obtained from Compound 32 (18 mg, 0.029 mmol) obtained in Example 28 in a manner similar to that in Example 11.

$[\alpha]^{26}_D$=−66.5° (c=0.224, methanol)

EXAMPLE 13

Synthesis of Compound 14

Compound G (6.50 g, 13.1 mmol) was treated in a manner similar to that in Example 3 to prepare a crude hydrochloride. The resulting crude hydrochloride was recrystallized from methanol/chloroform in a manner similar to that in Example 3 to obtain Compound 14 (2.20 g; yield: 26%).

$^1$H-NMR (CD$_3$OD, 300 MHz) δ 8.87–8.76 (m, 2H), 8.59 (m, 1H) 8.01 (m, 1H), 7.67 (m, 1H), 7.58 (m, 1H), 7.40 (m, 1H), 7.18 (m, 1H), 7.33–6.80 (m, 2H), 6.75 (m, 1H), 5.72 (br s, 1H), 4.42–3.95 (m, 4H), 3.62–3.33 (m, 2H), 2.52 (br s, 1H), 2.16 (m, 1H)

EXAMPLE 14

Synthesis of Compound 15

Compound 15 (639 mg; yield: 60%) was obtained from Compound H (1.1 g, 2.0 mmol) and a borane dimethyl sulfide complex (0.95 mL, 10 mmol) in a manner similar to that in Example 1.

$^1$H-NMR (DMSO-d$_6$, 300 MHz) δ 9.24 (s, 1H), 8.95 (br s, 1H) 8.46–8.44 (m, 2H), 7.81 (d, J=7.9 Hz, 1H), 7.70–7.63 (m, 2H), 7.40–7.31 (m, 3H), 7.01–6.96 (m, 3H), 5.26 (dd, J=10.4, 10.2 Hz, 1H), 3.76–3.61 (m, 3H), 3.06 (d, J=13.9 Hz, 1H), 2.89 (dd, J=11.2, 2.4 Hz, 1H), 2.34 (m, 1H), 1.82 (m, 1H), 1.67 (m, 1H)

EXAMPLE 15

Synthesis of Compound 16

A borane dimethyl sulfide complex (1.4 mL, 15 mmol) was added to a tetrahydrofuran solution (300 mL) of Compound I (1.34 g, 3.0 mmol), followed by stirring for 2 hours. The solvent was removed under reduced pressure, chloroform was added to the residue, and the mixture was washed with a saturated aqueous solution of sodium hydrogencarbonate. The resulting chloroform solution was dried over sodium sulfate, and the solvent was evaporated under reduced pressure. The residue was dissolved in methanol (100 mL), and hydrochloric acid (1 mol/l, 20 mL) was added thereto, followed by stirring at 50° C. for 1 hour. The reaction mixture was neutralized with a saturated aqueous solution of sodium hydrogencarbonate and extracted with chloroform. The extract was dried over sodium sulfate, and the solvent was evaporated under reduced pressure. The resulting residue was purified by silica gel column chromatography (eluted with chloroform/methanol=19/1) to obtain Compound 16 (171 mg; yield: 13%).

$^1$H-NMR (DMSO-$d_6$, 300 MHz) δ 9.07 (br s, 1H), 8.95 (br s, 1H) 8.45 (d, J=6.5 Hz, 1H), 8.40 (br s, 1H), 8.01 (d, J=7.7 Hz, 1H), 7.60 (m, 1H), 7.56 (m, 1H), 7.19–7.14 (m, 3H), 6.69 (br s, 1H), 6.71–6.69 (m, 2H), 5.18 (dd, J=10.8, 10.3 Hz, 1H), 3.70–3.55 (m, 3H), 3.41–3.22 (m, 2H), 2.84 (d, J=11.7 Hz, 1H), 2.73–2.50 (m, 2H), 1.91–1.71 (m, 2H), 1.10 (t, J=7.5 Hz, 3H)

EXAMPLE 16

Synthesis of Compound 17, Compound 18 and Compound 19

Compound 17 (9.6 mg; yield: 12%), Compound 18 (9.5 mg; yield: 10%), and Compound 19 (2.6 mg; yield: 3%) were obtained from Compound J (100 mg, 2.0 mmol) and a borane dimethyl sulfide complex (0.90 mL, 10 mmol) in a manner similar to that in Example 1.

Compound 17:

$^1$H-NMR (DMSO-$d_6$, 300 MHz) δ 9.07 (br s, 1H), 8.95 (br s, 1H) 8.45 (d, J=6.5 Hz, 1H), 8.41 (br s, 1H), 8.01 (d, J=7.9 Hz, 1H), 7.69–7.64 (m, 2H), 7.33–7.12 (m, 3H), 6.88 (m, 1H), 6.80–6.68 (m, 2H), 5.24 (dd, J=10.8, 9.7 Hz, 1H), 4.65–4.59 (m, 2H), 4.63 (d, J=11.9 Hz, 1H), 3.70–3.62 (m, 3H), 3.55–3.44 (m, 4H), 3.23 (d, J=14.7 Hz, 1H), 2.50 (m, 1H), 1.99–1.79 (m, 3H)

Compound 18:

$^1$H-NMR (DMSO-$d_6$, 300 MHz) δ 9.07 (br s, 1H), 8.94 (br s, 1H), 8.45 (d, J=5.3 Hz, 1H), 8.31 (br s, 1H), 8.01 (d, J=7.9 Hz, 1H), 7.73–7.64 (m, 2H), 7.44–7.22 (m, 3H), 7.12 (m, 1H), 6.71–6.69 (m, 2H), 5.91 (s, 1H), 5.24 (dd, J=10.6, 9.7 Hz, 1H), 4.12–3.96 (m, 5H), 3.69–3.55 (m, 2H), 3.24 (d, J=14.5 Hz, 1H), 2.84 (m, 1H), 2.50 (m, 1H), 1.99–1.79 (m, 2H)

Compound 19:

$^1$H-NMR (DMSO-$d_6$, 300 MHz) δ 9.03 (br s, 1H), 8.99 (br s, 1H) 8.45 (m, 1H), 7.65 (d, J=7.8 Hz, 1H), 7.57 (d, J=7.8 Hz, 1H), 7.36–7.15 (m, 4H), 6.93 (br s, 1H), 6.72–6.68 (m, 2H), 5.17–5.06 (m, 2H), 4.61 (dd, J=12.5, 6.9 Hz, 1H), 4.40 (dd, J=12.5, 4.1 Hz, 1H), 3.68–3.58 (m, 3H), 3.06 (d, J=13.5 Hz, 1H), 2.85 (d, J=13.5 Hz, 1H), 2.33 (m, 1H), 1.89–1.75 (m, 2H)

EXAMPLE 17

Synthesis of Compound 20

Hydrochloric acid (2 mol/l, 0.2 mL) was added to an acetone solution (2 mL) of Compound 18 (7.5 mg, 3.0 mmol), and the mixture was stirred at room temperature for 1 hour. The reaction solution was neutralized with a saturated aqueous solution of sodium hydrogencarbonate and extracted with chloroform/methanol (9/1), and the extract was dried over sodium sulfate. The solvent was evaporated under reduced pressure. The resulting residue was purified by preparative thin layer chromatography (developed with chloroform/methanol=9/1) to obtain Compound 20 (4.8 mg; yield: 71%).

$^1$H-NMR (DMSO-$d_6$, 300 MHz) δ 10.26 (s, 1H), 9.04 (br s, 1H) 8.98 (br s, 1H), 8.46–8.44 (m, 2H), 7.82 (d, J=8.0 Hz, 1H), 7.70–7.58 (m, 3H), 7.48 (m, 1H), 7.32 (m, 1H), 6.93 (m, 1H), 6.73–6.70 (m, 2H), 5.21 (dd, J=10.7, 9.8 Hz, 1H), 4.65–4.51 (m, 2H), 3.64 (d, J=14.3 Hz, 1H), 3.06 (d, J=14.3 Hz, 1H), 2.88 (m, 1H), 2.45 (m, 1H), 1.89–1.75 (m, 2H)

EXAMPLE 18

Synthesis of Compound 21

Compound 21 (27 mg; yield: 27%) was obtained from Compound K (52 mg, 0.2 mmol) and a borane dimethyl sulfide complex (0.90 mL, 10 mmol) in a manner similar to that in Example 1.

$^1$H-NMR (DMSO-$d_6$, 300 MHz) δ 9.07 (br s, 1H), 8.94 (br s, 1H) 8.45 (d, J=5.3 Hz, 1H), 8.31 (br s, 1H), 8.01 (d, J=7.9 Hz, 1H), 7.73–7.64 (m, 2H), 7.44–7.22 (m, 3H), 7.12 (m, 1H), 6.71–6.69 (m, 2H), 6.19 (s, 1H), 5.24 (dd, J=10.4, 9.9 Hz, 1H), 3.80–3.64 (m, 4H), 3.40–3.23 (m, 2H), 3.24 (d, J=14.2 Hz, 1H), 2.84 (m, 1H), 2.46 (m, 1H), 2.00–1.81 (m, 2H)

EXAMPLE 19

Synthesis of Compound 22 p-Toluenesulfonic acid monohydrate (19 mg, 0.1 mmol) was added to a methanol solution (5 mL) of Compound 20 (43 mg, 0.1 mmol), and the mixture was stirred at room temperature for 3 hours. The reaction solution was neutralized with a saturated aqueous solution of sodium hydrogencarbonate and extracted with chloroform/methanol (9/1), and the extract was dried over sodium sulfate. The solvent was evaporated under reduced pressure, and the resulting residue was purified by preparative thin layer chromatography (developed with chloroform/methanol=9/1) to obtain Compound 22 (32 mg; yield: 67%).

$^1$H-NMR (CD$_3$OD, 300 MHz) δ 8.42 (d, J=7.9 Hz, 1H), 8.36–8.33 (br s, 2H), 7.47–7.42 (m, 2H), 7.34–7.26 (m, 2H), 7.16 (t, J=7.5 Hz, 1H), 6.92 (br s, 1H), 6.70–6.67 (m, 2H), 5.46 (s, 1H), 4.98 (dd, J=11.3, 9.4 Hz, 1H), 3.81 (m, 1H), 3.81 (d, J=14.0 Hz, 1H), 3.75 (d, J=9.4 Hz, 1H), 3.60 (d, J=9.4 Hz, 1H), 3.34 (s, 3H), 3.10 (s, 3H), 2.93 (m, 1H), 2.31 (m, 1H), 1.77–1.73(m, 2H)

EXAMPLE 20

Synthesis of Compound 23

To a DMF solution (2 mL) of palladium (II) diacetate (3 mg, 0.01 mmol) and triphenylphosphine (10 mg, 0.04 mmol) were added vinyltributyltin (0.058 mL, 0.2 mmol), Compound 15 (53 mg, 0.1 mmol), and triethylamine (0.3 mL) in an argon atmosphere, and the mixture was stirred at 60° C. for 2.5 hours. The reaction solution was filtered through Celite, and chloroform was added to the filtrate, followed by washing with hydrochloric acid (1 mol/l). The organic layer was neutralized with a saturated aqueous solution of sodium hydrogencarbonate and dried over sodium sulfate. The solvent was evaporated under reduced pressure, and the residue was purified by silica gel column chromatography (eluted with chloroform/methanol=1/19) to obtain Compound 23 (12 mg; yield: 28%).

$^1$H-NMR (CDCl$_3$, 300 MHz) δ 8.49 (s, 1H), 8.41 (d, J=4.4 Hz, 1H), 7.57 (d, J=7.7 Hz, 1H), 7.34 (d, J=8.8 Hz, 1H), 7.26–7.15 (m, 4H), 7.13–6.95 (m, 2H), 6.91–6.78 (m, 2H), 5.49 (dd, J=17.2, 1.1 Hz, 1H), 5.29 (dd, J=12.3, 1.1 Hz, 1H), 4.92 (dd, J=11.6, 10.3 Hz, 1H), 3.83 (d, J=14.0 Hz, 1H), 3.70 (m, 1H), 3.64 (d, J=10.3 Hz, 1H), 3.07 (d, J=14.0 Hz, 1H), 2.97 (d, J=11.6 Hz, 1H), 2.39 (m, 1H), 1.62–1.58 (m, 2H)

EXAMPLE 21

Synthesis of Compound 24

Compound 24 (9.6 mg; 4:1 diastereomer mixture; yield: 6.4%) was obtained from Compound L (60 mg, 0.13 mmol) and a borane dimethyl sulfide complex (0.95 mL, 10 mmol) in a manner similar to that in Example 1.

EXAMPLE 22

Synthesis of Compound 25

Compound 25 (23 mg; yield: 49%) was obtained from Compound M (49 mg, 0.1 mmol) and a borane dimethyl sulfide complex (0.047 mL, 0.5 mmol) in a manner similar to that in Example 1.

$^1$H-NMR (DMSO-$d_6$, 300 MHz) δ 9.18 (br s, 2H), 8.55–8.53 (m, 2H), 7.72 (d, J=7.9 Hz, 1H), 7.60–7.36 (m, 5H), 6.98 (br s, 1H), 6.83–6.75 (m, 2H), 5.83 (dd, J=11.5, 9.2 Hz, 1H), 4.39 (m, 1H), 3.76–3.70 (m, 2H), 3.15 (d, J=13.9 Hz, 1H), 3.01 (m, 1H), 2.60 (m, 1H), 2.45 (m, 1H), 1.90 (m, 1H)

EXAMPLE 23

Synthesis of Compound 26

Compound 26 (31 mg; yield; 55%) was obtained from Compound N (60 mg, 0.12 mmol) and a borane dimethyl sulfide complex (0.057 mL, 0.60 mmol) in a manner similar to that in Example 1.

$^1$H-NMR (DMSO-$d_6$, 300 MHz) δ 9.15 (br s, 2H), 8.57–8.55 (m, 2H), 8.11 (d, J=2.3 Hz, 1H), 7.75 (d, J=7.9 Hz, 1H), 7.55 (d, J=8.6 Hz, 1H), 7.46–7.42 (m, 2H), 7.10 (br s, 1H), 6.85–6.76 (m, 2H), 5.47 (dd, J=10.6, 9.9 Hz, 1H), 3.80 (m, 1H), 3.76–3.68 (m, 2H), 3.15 (d, J=13.9 Hz, 1H), 2.95 (m, 1H), 2.60 (m, 1H), 1.87–1.80 (m, 2H)

EXAMPLE 24

Synthesis of Compound 27

Compound 27 (21 mg; yield: 60%) was obtained from Compound O (36 mg, 0.069 mmol) and a borane dimethyl sulfide complex (0.033 mL, 0.35 mmol) in a manner similar to that in Example 1.

$^1$H-NMR (DMSO-$d_6$, 300 MHz) δ 9.15 (br s, 2H), 8.56–8.53 (m, 2H), 8.16 (d, J=2.3 Hz, 1H), 7.85 (d, J=2.3 Hz, 1H), 7.74 (d, J=2.3 Hz, 1H), 7.43 (dd, J=7.4, 4.3 Hz, 1H), 7.05 (br s, 1H), 6.81 (d, J=7.9 Hz, 2H), 5.51 (dd, J=11.2, 9.6 Hz, 1H), 4.05 (m, 1H), 3.77–3.71 (m, 2H), 3.15 (d, J=13.9 Hz, 1H), 2.95 (m, 1H), 2.50 (m, 1H), 1.90–1.80 (m, 2H)

EXAMPLE 25

Synthesis of Compound 28

Compound 28 (18 mg; yield: 60%) was obtained from Compound P (31 mg, 0.054 mmol) and a borane dimethyl sulfide complex (0.026 mL; 0.27 mmol) in a manner similar to that in Example 1.

$^1$H-NMR (CDCl$_3$, 300 MHz) δ 8.43 (S, 1H), 7.53 (d, J=7.6 Hz, 1H), 7.46 (m, 1H), 7.37 (d, J=3.6 Hz, 1H), 7.25–7.19 (m, 3H), 6.91 (br s, 1H), 6.77–6.60 (m, 2H), 4.65 (dd, J=11.2, 9.4 Hz, 1H), 3.78 (d, J=14.2 Hz, 1H), 3.56 (d, J=9.4 Hz, 1H), 3.15 (m, 1H), 3.04–2.93 (m, 2H), 2.40 (m, 1H), 1.90–1.80 (m, 2H)

EXAMPLE 26

Synthesis of Compound 29

Compound 29 (43 mg; yield: 69%) was obtained from Compound Q (33 mg, 0.072 mmol) and a borane dimethyl sulfide complex (0.025 mL, 0.27 mmol) in a manner similar to that in Example 1.

$^1$H-NMR (CDCl$_3$, 300 MHz) δ 8.49 (br s, 2H), 7.56–7.47 (m, 4H) 7.41–7.20 (m, 6H), 6.98 (m, 1H), 5.02 (dd, J=10.7, 10.1 Hz, 1H), 4.07 (m, 1H), 3.86 (d, J=9.4 Hz, 1H), 3.75 (d, J=13.7 Hz, 1H), 3.06–2.95 (m, 2H), 2.43 (m, 1H), 2.04 (d, J=11.4 Hz, 1H), 1.68 (m, 1H)

EXAMPLE 27

Synthesis of Compound 30

Triethylamine (5 mL) and isobutyryl chloride (1.00 mL) were added to a chloroform solution (10 mL) of Compound 14 (600 mg, 1.08 mmol), followed by stirring for 7 hours. After concentration under reduced pressure, the residue was purified by column chromatography (eluted with methanol/chloroform=5/95) to obtain Compound 30 (375 mg; yield: 56%).

$^1$H-NMR (CDCl$_3$, 300 MHz) δ 8.50–8.48 (m, 2H), 7.72–7.51 (m, 2H), 7.40–7.20 (m, 6H), 7.01 (m, 1H), 4.93 (dd, J=9.6, 11.2 Hz, 1H), 4.04 (m, 1H), 3.85 (d, J=9.6 Hz, 1H), 3.82 (d, J=13.1 Hz, 1H), 3.06 (d, J=13.1 Hz, 1H), 3.03 (m, 1H), 2.77 (m, 2H), 2.42 (m, 1H), 2.03 (m, 1H), 1.71 (m, 1H), 1.31 (d, J=7.0 Hz, 6H), 1.28 (d, J=7.0 Hz, 6H)

EXAMPLE 28

Synthesis of Compound 31 and Compound 32

Compound 31 (79 mg; yield: 26%) which is the (+)-form of Compound 30 and Compound 32 (52 mg; yield: 17%) which is the (–)-form of Compound 30 were obtained from Compound 30 (300 mg) in a manner similar to that in Example 2.

Compound 31: $[\alpha]^{28}_D$=+76.7° (c=0.34, methanol)
Compound 32: $[\alpha]^{26}_D$=−75.8° (c=0.36, methanol)

EXAMPLE 29

Synthesis of Compound 33

Compound 33 (290 mg; yield: 69%) was obtained from Compound 65 (370 mg, 0.74 mmol) and isobutyryl chloride (0.105 mL, 1.0 mmol) in a manner similar to that in Example 27.

$^1$H-NMR (CDCl$_3$, 270 MHz) δ 8.52 (br s, 1H), 8.49 (d, J=3.6 Hz, 1H), 7.55–7.51 (m, 2H), 7.38–7.12 (m, 3H), 7.09–7.05 (m, 4H), 4.96 (dd, J=11.2, 9.5 Hz, 1H), 4.10 (m, 1H), 3.86–3.81 (m, 5H), 3.08–3.03 (m, 2H), 2.81 (m, 1H), 2.43 (m, 1H), 2.04 (m, 1H), 1.74 (d, J=7.2 Hz, 1H), 1.30 (d, J=7.2 Hz, 6H)

EXAMPLE 30

Synthesis of Compound 34 and Compound 35

Compound 34 (79 mg; yield: 26%) and Compound 35 (52 mg; yield: 17%) were obtained from Compound 33 (290 mg) in a manner similar to that in Example 2.
Compound 34: Retention time=46 minutes
Compound 35: Retention time=58 minutes

EXAMPLE 31

Synthesis of Compound 36

Compound 36 (512 mg; yield: 31%) was obtained from Compound S (1.35 g, 2.6 mmol) in a manner similar to that in Example 1.

$^1$H-NMR (CDCl$_3$, 300 MHz) δ 8.52–8.49 (m, 2H), 7.61–7.53 (m, 2H), 7.38–7.21 (m, 3H), 7.09 (ddd, J=8.0, 7.2, 1.9 Hz, 1H), 7.02–6.91 (m, 2H), 6.84 (d, J=8.2 Hz, 1H), 4.98 (dd, J=10.7, 9.7 Hz, 1H), 4.03 (m, 1H), 3.92 (s, 3H), 3.87 (s, 3H), 3.87–3.78(m, 2H), 3.07–3.03 (m, 2H), 2.43 (m, 1H), 2.05 (m, 1H), 1.70 (m, 1H)

EXAMPLE 32

Synthesis of Compound 37

Triethylamine (0.5 ml) and N,N-dimethylcarbamyl chloride (0.184 mL, 2.0 mo) were successively added to a methylene chloride solution (200 mL) of Compound 1 (468 mg, 1.0 mmol) under cooling with ice, followed by stirring at room temperature for about 30 minutes. The reaction solution was poured into water and the mixture was extracted with a chloroform/methanol (9/1) mixed solvent. The extract was dried over sodium sulfate, and the solvent was removed under reduced pressure. The resulting residue was purified by silica gel column chromatography (eluted with chloroform) and re-precipitated in diethyl ether/hexane to obtain Compound 37 (212 mg; yield: 39%).

$^1$H-NMR (CDCl$_3$, 300 MHz) δ 8.50–8.48 (m, 2H), 7.61–7.46 (m, 4H), 7.36–7.21 (m, 4H), 7.17 (d, J=8.8 Hz, 1H), 7.08 (td, J=8.0, 1.8 Hz, 1H), 4.97 (dd, J=11.3, 9.3 Hz, 1H), 4.07 (m, 1H), 3.86 (d, J=9.3 Hz, 1H), 3.81 (d, J=13.7 Hz, 1H), 3.08 (s, 3H), 3.07 (d, J=13.7 Hz, 1H), 3.00 (s, 3H), 2.42 (dd, J=12.1, 9.5 Hz, 1H), 2.04 (d, J=9.5 Hz, 1H), 1.69 (m, 1H), 1.54 (m, 1H)

EXAMPLE 33

Synthesis of Compound 38

Compound 38 (475 mg; yield: 73%) was obtained from Compound 1 (468 mg, 1.0 mmol) and lauroyl chloride (0.23 mL, 1.0 mmol) in a manner similar to that in Example 32.

$^1$H-NMR (DMSO-d$_6$, 300 MHz) δ 8.51–8.49 (m, 2H), 7.54–7.48(m, 4H), 7.36–7.21 (m, 3H), 7.15–7.06 (m, 3H), 4.97 (dd, J=11.0, 9.5 Hz, 1H), 4.10–4.02 (m, 1H), 3.86 (d, J=9.5 Hz, 1H), 3.78 (d, J=13.9 Hz, 1H), 3.06–3.02 (m, 2H), 2.53 (t, J=7.5 Hz, 2H), 2.43 (dt, J=12.0, 2.0 Hz, 1H), 2.05 (d, J=10.9 Hz, 1H), 1.70 (m, 1H), 1.38–1.26 (m, 18H), 0.88 (t, J=6.7 Hz, 3H)

EXAMPLE 34

Synthesis of Compound 39

Compound 1 (65 mg, 0.139 mmol) was dissolved in pyridine (1.0 mL), and trifluoromethanesulfonic acid anhydride (0.03 mL, 0.178 mmol) was added thereto, followed by stirring at room temperature for 12 hours and 30 minutes. Trifluoromethanesulfonic acid anhydride (0.03 mL, 0.178 mmol) was further added thereto, and stirring was continued for 3 hours at room temperature. The reaction mixture was extracted with chloroform (50 mL×2), and the extract was washed with a saturated aqueous sodium hydrogencarbonate solution (10 mL) and dried over anhydrous sodium sulfate, followed by concentration under reduced pressure. The residue was purified by silica gel column chromatography (eluted with methanol/chloroform=3/7 to 1/1) to obtain Compound 39 (59 mg; yield: 71%).

$^1$H-NMR (CDCl$_3$, 300 MHz) δ 8.53–8.50 (m, 2H), 7.61–7.51 (m, 4H), 7.34–7.23 (m, 5H), 7.10 (m, 1H), 4.93 (dd, J=9.6, 11.0 Hz, 1H), 4.07 (dt, J=3.6, 11.0 Hz, 1H), 3.92 (d, J=9.6 Hz, 1H), 3.70 (d, J=13.8 Hz, 1H), 3.08 (m, 1H), 3.07 (d, J=13.8 Hz, 1H), 2.43 (dd, J=2.0, 11.0 Hz, 1H), 2.06 (br d, J=11.0 Hz, 1H), 1.73 (dq, J=3.0, 11.0 Hz, 1H)

EXAMPLE 35

Synthesis of Compound 40

Compound 40 (18 mg; yield: 30%) was obtained from Compound T (58 mg, 0.12 mmol) in a manner similar to that in Example 1.

$^1$H-NMR (CDCl$_3$, 300 MHz) δ 8.52–8.49 (m, 2H), 7.61–7.53 (m, 2H), 7.38–7.21 (m, 3H), 7.09 (ddd, J=8.0, 7.2, 1.9 Hz, 1H), 7.02 (d, J=8.2 Hz, 2H), 6.84 (d, J=8.2 Hz, 2H), 4.98 (dd, J=10.7, 9.7 Hz, 1H), 4.03 (m, 1H), 3.90 (s, 3H), 3.89–3.80 (m, 2H), 3.07–3.03 (m, 2H), 2.43 (m, 1H), 2.05 (m, 1H), 1.70 (m, 1H)

EXAMPLE 36

Synthesis of Compound 41

Potassium carbonate (690 mg, 5.0 mmol) and 3-chloro-2-methylpropene (0.492 mL, 4.8 mol) were successively added to a DMF solution (200 ml) of Compound 1 (467 mg, 1.0 mmol) under cooling with ice, and the mixture was stirred at 70° C. for 12 hours. The reaction solution was poured into water, the mixture was extracted with a chloroform/methanol (9/1) mixed solvent, and the extract was dried over sodium sulfate. The solvent was removed under reduced pressure. The resulting residue was purified by silica gel column chromatography (eluted with chloroform) and re-precipitated in diethyl ether/hexane to obtain Compound 41 (380 mg; yield: 73%).

$^1$H-NMR (CDCl$_3$, 270 MHz) δ 8.50–8.48 (m, 2H), 7.56–7.50 (m, 2H), 7.38–7.19 (m, 5H), 7.07 (m, 1H), 6.93–6.85 (m, 2H), 5.07–4.97 (m, 3H), 4.39 (s, 2H), 4.05 (m, 1H), 3.81–3.76 (m, 2H), 3.04–2.96 (m, 2H), 2.41 (m, 1H), 2.09 (m, 1H), 1.81 (s, 3H), 1.70 (m, 1H)

EXAMPLE 37

Synthesis of Compound 42

Compound 42 (34 mg; yield: 69%) was obtained from Compound U (50 mg, 0.072 mmol) and a borane dimethyl sulfide complex (0.025 mL, 0.27 mmol) in a manner similar to that in Example 1.

$^1$H-NMR (CDCl$_3$, 300 MHz) δ 8.52–8.46 (m, 2H), 7.64 (d, J=7.7 Hz, 1H), 7.58 (d, J=8.4 Hz, 1H), 7.52 (dd, J=7.9, 1.1 Hz, 1H), 7.35 (d, J=7.7 Hz, 1H), 7.30–7.20 (m, 3H), 7.08 (m, 1H), 6.67 (br s, 1H), 4.97 (dd, J=10.9, 9.5 Hz, 1H), 4.17 (m, 1H), 3.82 (d, J=9.5 Hz, 1H), 3.79 (d, J=13.8 Hz, 1H), 3.04–3.00 (m, 2H), 2.40 (m, 1H), 2.03 (m, 1H), 1.62 (m, 1H), 1.52 (s, 9H), 1.49 (s, 9H)

EXAMPLE 38

Synthesis of Compound 43 and Compound 44

Hydrochloric acid (6 mol/l, 2.0 mL) was added to a tetrahydrofuran solution (10 mL) of Compound 42 (34 mg, 0.05 mmol), followed by refluxing for 3 hours. The reaction solution was poured into a saturated aqueous solution of sodium hydrogencarbonate and the mixture was extracted with a chloroform/methanol (9/1) mixed solvent. The extract was dried over sodium sulfate, and the solvent was removed under reduced pressure. The resulting residue was dissolved in methylene chloride (5 mL), and triphosgene (15 mg, 0.054 mmol) and pyridine (1 mL) were added thereto, followed by stirring at room temperature for 2 hours. The reaction mixture was poured into an aqueous sodium hydroxide solution (0.5 mol/l) and, after stirring for 10 minutes, the mixture was neutralized with dilute hydrochloric acid and extracted with a chloroform/methanol (9/1) mixed solvent. The extract was dried over sodium sulfate, and the solvent was evaporated under reduced pressure. The residue was purified by silica gel column chromatography (eluted with chloroform/methanol=96/4), and each product was re-precipitated in diethyl ether/hexane to obtain Compound 43 (3.4 mg; yield: 11%) and Compound 44 (4.3 mg; yield: 17%).

Compound 43:

$^1$H-NMR (CDCl$_3$, 300 MHz) δ 8.51–8.49 (m, 2H), 7.70 (m, 1H) 7.62 (d, J=4.6 Hz, 1H), 7.54–7.51 (m, 2H), 7.35 (d,

J=7.5 Hz, 1H), 7.31–7.11 (m, 2H), 7.09 (m, 1H), 7.06 (m, 1H), 4.97 (dd, J=11.4, 9.7 Hz, 1H), 4.04 (m, 1H), 3.85–3.67 (m, 2H), 3.83 (s, 3H), 3.81 (s, 3H), 3.07–3.02 (m, 2H), 2.24 (m, 1H), 2.00 (m, 1H), 1.64 (m, 1H)

Compound 44:

$^1$H-NMR (DMSO-d$_6$, 300 MHz) δ 9.71 (br s, 1H), 9.60 (br s, 1H) 8.63 (br s, 1H), 8.48 (d, J=4.1 Hz, 1H), 7.54–7.51 (m, 2H), 7.40–7.18 (m, 4H), 7.11–7.00 (m, 3H), 5.04 (dd, J=10.5, 10.2 Hz, 1H), 4.10 (m, 1H), 3.87–3.81 (m, 2H), 3.07–3.00 (m, 2H), 2.45 (m, 1H), 2.04 (m, 1H), 1.72 (m, 1H)

EXAMPLE 39

Synthesis of Compound 45

Concentrated nitric acid (0.055 mL, 1.4 mmol) was added to an acetic acid solution (10 mL) of Compound 1 (302 mg, 0.69 mmol) under cooling with ice. The temperature was raised up to room temperature, at which the mixture was stirred for 1.5 hours. The reaction solution was poured into water, and the mixture was neutralized with a dilute aqueous solution of sodium hydroxide and extracted with a chloroform/methanol (9/1) mixed solvent. The extract was dried over sodium sulfate, and the solvent was removed under reduced pressure. The resulting residue was purified by silica gel column chromatography (eluted with chloroform/methanol=98/2) to obtain Compound 45 (219 mg; yield: 62%).

$^1$H-NMR (CDCl$_3$, 300 MHz) δ 10.61 (br s, 1H), 8.51 (dd, J=4.8, 1.2 Hz, 1H), 8.47 (d, J=1.7 Hz, 1H), 8.23 (br s, 1H), 7.72 (d, J=8.3 Hz, 1H), 7.56–7.53 (m, 2H), 7.37–7.15 (m, 4H), 7.10 (m, 1H), 4.93 (dd, J=10.8, 9.9 Hz, 1H), 4.08 (m, 1H), 3.90 (d, J=9.4 Hz, 1H), 3.73 (d, J=13.6 Hz, 1H), 3.11–3.06 (m, 2H), 2.46 (td, J=12.3, 2.0 Hz, 1H), 2.06 (d, J=11.2 Hz, 1H), 1.71 (m, 1H)

EXAMPLE 40

Synthesis of Compound 46

Palladium on carbon (21 mg) was added to a methanol solution (20 mL) of Compound 45 (210 mg, 0.41 mmol) in a nitrogen atmosphere, and the mixture was refluxed for 5 hours. The catalyst was removed by Celite filtration, and the solvent was evaporated under reduced pressure. The resulting residue was purified by silica gel column chromatography (eluted with chloroform/methanol=95/5) to obtain Compound 46 (87 mg; yield: 44%).

$^1$H-NMR (DMSO-d$_6$, 300 MHz) δ 9.14 (br s, 1H), 8.46 (m, 2H) 7.71 (d, J=6.6 Hz, 1H), 7.65 (d, J=7.9 Hz, 1H), 7.57 (dd, J=8.1, 1.1 Hz, 1H), 7.40–7.29 (m, 2H), 7.17(m, 1H), 6.77 (br s, 1H), 6.63 (d, J=7.7 Hz, 1H), 6.53 (m, 1H), 5.19 (dd, J=11.0, 9.6 Hz, 1H), 4.60 (br s, 2H), 3.86 (m, 1H), 3.67 (d, J=13.8 Hz, 1H), 3.56 (d, J=9.1 Hz, 1H), 3.04 (d, J=13.8 Hz, 1H), 2.87 (dd, J=11.6, 3.3 Hz, 1H), 2.34 (m, 1H), 1.90 (m, 1H), 1.73 (m, 1H)

EXAMPLE 41

Synthesis of Compound 47

Methanesulfonyl chloride (0.008 mL, 0.1 mol) was added to a DMF solution (5 mL) of Compound 46 (24 mg, 0.05 mmol), and the mixture was stirred at room temperature for 1 hour. The reaction solution was poured into water and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform) and re-precipitated in diethyl ether/hexane to obtain Compound 47 (8.9 mg; yield: 16%).

$^1$H-NMR (DMSO-d$_6$, 300 MHz) δ 9.64 (s, 1H), 8.58–8.55 (m, 2H) 7.93 (d, J=7.9 Hz, 1H), 7.79 (d, J=7.9 Hz, 1H), 7.62–7.58 (m, 2H), 7.45–7.39 (m, 3H), 7.19 (m, 1H), 5.44 (dd, J=13.2, 9.2 Hz, 2H), 3.98–3.88 (m, 2H), 3.62 (d, J=12.9 Hz, 1H), 3.51 (s, 3H), 3.15 (d, J=12.9 Hz, 1H), 3.04 (s, 3H), 2.90 (m, 1H), 2.50 (m, 1H), 1.90–1.82 (m, 2H)

EXAMPLE 42

Synthesis of Compound 48

Methanesulfonyl chloride (0.0077 mL, 0.10 mol) was added to a methylene chloride/DMF solution (2/1, 3 mL) of Compound 46 (48 mg, 0.10 mmol), and the mixture was stirred at room temperature for 30 minutes. The reaction solution was poured into water and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform) and re-precipitated in diethyl ether/hexane to obtain Compound 48 (8.9 mg; yield: 16%).

$^1$H-NMR (CDCl$_3$, 300 MHz) δ 8.54 (br s, 1H), 8.45 (d, J=4.0 Hz, 1H), 7.69 (d, J=7.6 Hz, 1H), 7.69 (m, 1H), 7.53 (d, J=8.1 Hz, 1H), 7.38–7.21 (m, 4H), 7.08 (d, J=7.0 Hz, 1H), 6.92 (d, J=8.1 Hz, 1H), 4.98 (dd, J=10.7, 9.8 Hz, 1H), 4.06 (m, 1H), 3.90 (d, J=14.1 Hz, 1H), 3.82 (d, J=9.0 Hz, 1H), 3.18 (d, J=14.1 Hz, 1H), 3.05 (dd, J=11.6 Hz, 1H), 2.51 (m, 1H), 2.04 (m, 1H), 1.76 (m, 1H), 1.43 (s, 3H)

EXAMPLE 43

Synthesis of Compound 49

Ethanesulfonyl chloride (0.0094 mL, 0.10 mol) and pyridine (0.1 mL) were added to a DMF solution (5 mL) of Compound 46 (24 mg, 0.05 mmol), and the mixture was stirred at room temperature for 1 hour. The reaction solution was poured into water and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform) and re-precipitated in diethyl ether/hexane to obtain Compound 49 (7.3 mg; yield: 22%).

$^1$H-NMR (DMSO-d$_6$, 270 MHz) δ 8.43–8.41 (m, 2H), 7.74 (d, J=7.9 Hz, 1H), 7.68 (d, J=7.9 Hz, 1H), 7.56 (d, J=7.9 Hz, 1H), 7.37–7.27 (m, 2H), 7.18–7.05 (m, 2H), 6.83 (m, 1H), 5.24 (dd, J=10.2, 9.2 Hz, 1H), 3.90 (d, J=13.5 Hz, 1H), 3.88 (m, 1H), 3.62 (d, J=9.2 Hz, 1H), 3.59 (d, J=13.5 Hz, 1H), 3.08 (d, J=13.5 Hz, 1H), 3.04 (m, 1H), 2.50 (m, 1H), 1.70 (m, 1H)

EXAMPLE 44

Synthesis of Compound 50

Ethanesulfonyl chloride (0.0094 mL, 0.10 mol) and pyridine (0.1 mL) were added to a methylene chloride solution (10 mL) of Compound 46 (24 mg, 0.05 mmol), and the mixture was stirred at room temperature for 30 minutes. The reaction solution was poured into water and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform) and re-precipitated in diethyl ether/hexane to obtain Compound 50 (2.3 mg; yield: 8%).

$^1$H-NMR (DMSO-$d_6$, 270 MHz) δ 10.04 (s, 1H), 8.71 (s, 1H) 8.56 (d, J=4.6 Hz, 1H), 8.44–8.30 (m, 2H), 7.75 (d, J=8.9 Hz, 1H), 7.68 (d, J=7.6 Hz, 1H), 7.55 (d, J=7.9 Hz, 1H), 7.49 (m, 1H), 7.38–7.29 (m, 2H), 7.16 (m, 1H), 6.83 (d, J=8.3 Hz, 1H), 5.27 (dd, J=10.6, 9.3 Hz, 1H), 3.86 (m, 1H), 3.70 (d, J=9.2 Hz, 1H), 3.60 (d, J=13.5 Hz, 1H), 3.05 (d, J=13.5 Hz, 1H), 3.00 (q, J=7.4 Hz, 2H), 2.86 (d, J=12.2 Hz, 1H), 2.33 (m, 1H), 1.80–1.70 (m, 2H), 1.18 (t, J=7.4 Hz, 3H)

EXAMPLE 45

Synthesis of Compound 51

Phenylsulfonyl chloride (0.0064 mL, 0.05 mol) and pyridine (0.1 mL) were added to a methylene chloride solution (10 mL) of Compound 46 (24 mg, 0.05 mmol), and the mixture was stirred at room temperature for 30 minutes. The reaction solution was poured into water and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform) and re-precipitated in diethyl ether/hexane to obtain Compound 51 (12.2 mg; yield: 39%).

$^1$H-NMR (CD$_3$_D, 270 MHz) δ 8.34–8.32 (m, 2H), 7.67–7.59 (m, 4H), 7.54–7.39 (m, 5H), 7.34–7.28 (m, 2H), 7.08–6.98 (m, 3H), 5.01 (m, 1H), 3.90 (m, 1H), 3.67 (d, J=9.5 Hz, 1H), 3.42 (d, J=13.5 Hz, 1H), 2.97 (d, J=13.5 Hz, 1H), 2.86 (d, J=12.5 Hz, 1H), 2.32 (m, 1H), 1.85 (d, J=11.2 Hz, 1H), 1.65 (m, 1H)

EXAMPLE 46

Synthesis of Compound 52 p-Toluenesulfonyl chloride (0.0095 mg, 0.05 mol) was added to a methylene chloride solution (2 mL) of Compound 46 (24 mg, 0.05 mmol), and the mixture was stirred at room temperature for 2 hours. The reaction solution was poured into water and the mixture was extracted with a chloroform/methanol (9/1) mixed solvent. The extract was dried over sodium sulfate, and the solvent was evaporated under reduced pressure. The resulting residue was purified by preparative thin layer chromatography (developing solvent: chloroform/methanol=9/1) to obtain Compound 52 (9.5 mg; yield: 30%).

$^1$H-NMR (DMSO-$d_6$, 270 MHz) δ 9.73 (br s, 1H), 9.11 (br s, 1H), 8.46 (br s, 1H), 7.72 (m, 1H), 7.56 (d, J=8.0 Hz, 1H), 7.37–7.33 (m, 2H), 7.18 (d, J=8.2 Hz, 4H), 7.20–7.13 (m, 3H), 6.66 (d, J=7.9 Hz, 1H), 5.20 (dd, J=10.9, 10.2 Hz, 1H), 3.87 (m, 1H), 3.67 (d, J=9.2 Hz, 1H), 3.50 (d, J=14.2 Hz, 1H), 3.04 (d, J=14.2 Hz, 1H), 2.86 (d, J=10.9 Hz, 1H), 2.41 (m, 1H), 2.24 (s, 3H), 1.82–1.70 (m, 2H)

EXAMPLE 47

Synthesis of Compound 53 and Compound 54

Methyl chlorocarbonate (0.0036 mL, 0.05 mol) was added to a methylene chloride/DMF solution (2/1, 3 mL) of Compound 46 (48 mg, 0.10 mmol), and the mixture was stirred at room temperature for 30 minuets. The reaction solution was poured into water and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform), and each product was re-precipitated in diethyl ether/hexane to obtain Compound 53 (25.4 mg; yield: 42%) and Compound 54 (11.5 mg; yield: 21%).

Compound 53:

$^1$H-NMR (CDCl$_3$, 300 MHz) δ 8.51–8.48 (m, 2H), 7.69 (d, J=7.8 Hz, 1H), 7.52 (d, J=7.8 Hz, 1H), 7.38–7.23 (m, 5H), 7.10–7.01 (m, 3H), 4.99 (dd, J=10.6, 10.1 Hz, 1H), 4.06 (m, 1H), 3.91 (s, 3H), 3.88–3.80 (m, 5H), 3.05–2.88 (m, 2H), 2.42 (dd, J=13.0, 10.3 Hz, 1H), 1.99 (m, 1H), 1.70 (m, 2H)

Compound 54:

$^1$H-NMR (CDCl$_3$, 300 MHz) δ 8.51 (br s, 1H), 8.47 (d, J=3.3 Hz, 1H), 7.67 (d, J=7.7 Hz, 1H), 7.52 (d, J=7.7 Hz, 1H), 7.35 (d, J=7.3 Hz, 1H), 7.27–7.23 (m, 3H), 7.08 (t, J=7.2 Hz, 1H), 7.04 (br s, 1H), 6.85 (d, J=7.3 Hz, 1H), 5.01 (dd, J=10.8, 8.8 Hz, 1H), 4.04 (m, 1H), 3.94–3.76 (m, 5H), 3.13 (d, J=13.6 Hz, 1H), 3.02 (d, J=12.3 Hz, 1H), 2.47 (m, 1H), 2.03 (d, J=12.3 Hz, 1H), 1.69 (m, 1H)

EXAMPLE 48

Synthesis of Compound 55

Isobutyl chlorocarbonate (0.0068 mL, 0.05 mol) was added to a methylene chloride solution (2 mL) of Compound 46 (24 mg, 0.05 mmol), and the mixture was stirred at room temperature for 2 hours. The reaction solution was poured into water and the mixture was extracted with a chloroform/methanol (9/1) mixed solvent. The extract was dried over sodium sulfate, and the solvent was evaporated under reduced pressure. The resulting residue was purified by preparative thin layer chromatography (developing solvent: chloroform/methanol=9/1) to obtain Compound 55 (66 mg; yield: 26%).

$^1$H-NMR (CDCl$_3$, 270 MHz) δ 8.50 (br s, 1H), 8.45 (d, J=4.3 Hz, 1H), 8.10 (m, 1H), 7.53 (m, 1H), 7.52 (d, J=8.0 Hz, 1H), 7.33 (d, J=8.0 Hz, 1H), 7.31–7.29 (m, 2H), 7.22–7.04 (m, 2H), 6.96 (m, 1H), 4.98 (dd, J=11.2, 9.2 Hz, 1H), 4.02 (m, 1H), 3.79 (d, J=13.9 Hz, 1H), 3.74 (d, J=9.6 Hz, 1H), 3.15 (d, J=13.9 Hz, 1H), 3.01 (d, J=11.2 Hz, 1H), 2.64 (m, 2H), 2.45 (dd, J=11.2, 10.5 Hz, 1H), 2.01 (d, J=10.5 Hz, 1H), 1.70 (m, 1H), 1.29–1.23 (m, 7H)

EXAMPLE 49

Synthesis of Compound 56 and Compound 57

Acetyl chloride (0.0036 mL, 0.05 mol) was added to a methylene chloride solution (5 mL) of Compound 46 (24 mg, 0.05 mmol), and the mixture was stirred at room temperature for 1 hour. The reaction solution was poured into water and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform), and each product was re-precipitated in diethyl ether/hexane to obtain Compound 56 (23.1 mg; yield: 41%) and Compound 57 (7.2 mg; yield: 13%).

Compound 56:

$^1$H-NMR (CDCl$_3$, 300 MHz) δ 8.51–8.49 (m, 2H), 7.71 (m, 1H) 7.52 (d, J=7.9 Hz, 1H), 7.40–7.04 (m, 7H), 4.97 (dd, J=9.7, 8.8 Hz, 1H), 4.05 (m, 1H), 3.86 (d, J=8.8 Hz, 1H), 3.83 (d, J=13.4 Hz, 1H), 3.05–2.96 (m, 2H), 2.42 (m, 1H), 2.36 (s, 3H), 2.22 (s, 3H), 1.99 (m, 1H), 1.80–1.62 (m, 2H)

Compound 57:

$^1$H-NMR (CDCl$_3$, 300 MHz) δ 8.51–8.49 (m, 2H), 7.97 (m, 1H) 7.69 (d, J=7.9 Hz, 1H), 7.53 (d, J=9.0 Hz, 1H), 7.38–7.11 (m, 4H), 7.10 (t, J=7.3 Hz, 1H), 7.01 (d, J=7.5 Hz, 1H), 4.97 (dd, J=10.8, 8.8 Hz, 1H), 4.05 (m, 1H), 3.80 (d, J=13.6 Hz, 1H), 3.76 (d, J=8.8 Hz, 1H), 3.07–3.05 (m, 2H), 2.42 (m, 1H), 2.27 (s, 3H), 2.03 (d, J=15.2 Hz, 1H), 1.80 (m, 1H)

EXAMPLE 50

Synthesis of Compound 58

Valeryl chloride (0.0142 mL, 0.05 mol) was added to a methylene chloride solution (2 mL) of Compound 46 (24 mg, 0.05 mmol), and the mixture was stirred at room temperature for 2 hours. The reaction solution was poured into water and the mixture was extracted with a chloroform/methanol (9/1) mixed solvent. The extract was dried over sodium sulfate, and the solvent was evaporated under reduced pressure. The resulting residue was purified by preparative thin layer chromatography (developing solvent: chloroform/methanol=9/1) to obtain Compound 58 (14.2 mg; yield: 50%).

$^1$H-NMR (CDCl$_3$, 270 MHz) δ 8.48–8.42 (br s, 2H), 7.65 (d, J=7.1 Hz, 1H), 7.56 (d, J=8.2 Hz, 1H), 7.36–7.22 (m, 3H), 7.09–7.06 (m, 3H), 6.97 (d, J=7.9 Hz, 1H), 4.97 (dd, J=10.9, 9.9 Hz, 1H), 3.99 (m, 1H), 3.78 (d, J=14.1 Hz, 1H), 3.73 (d, J=9.6 Hz, 1H), 3.07 (d, J=14.1 Hz, 1H), 3.00 (d, J=12.2 Hz, 1H), 2.47–2.39 (m, 2H), 2.00 (d, J=10.9 Hz, 1H), 1.76–1.65 (m, 3H), 1.44–1.33 (m, 3H), 0.93 (d, J=7.4 Hz, 3H)

EXAMPLE 51

Synthesis of Compound 59

Isobutyryl chloride (0.0053 mL, 0.05 mol) was added to a methylene chloride solution (2 mL) of Compound 46 (24 mg, 0.05 mmol), and the mixture was stirred at room temperature for 2 hours. The reaction solution was poured into water and the mixture was extracted with a chloroform/methanol (9/1) mixed solvent. The extract was dried over sodium sulfate, and the solvent was evaporated under reduced pressure. The resulting residue was purified by preparative thin layer chromatography (developing solvent: chloroform/methanol=9/1) to obtain Compound 59 (8.3 mg; yield: 29%).

$^1$H-NMR (CDCl$_3$, 270 MHz) δ 8.48 (br s, 1H), 8.45 (d, J=4.0 Hz, 1H), 8.06 (br s, 1H), 7.69 (d, J=7.3 Hz, 1H), 7.65 (d, J=7.9 Hz, 1H), 7.39–7.26 (m, 3H), 7.08 (m, 1H), 6.93 (d, J=7.6 Hz, 1H), 5.00 (dd, J=10.5, 9.5 Hz, 1H), 4.05 (m, 1H), 3.80 (d, J=14.2 Hz, 1H), 3.75 (d, J=9.5 Hz, 1H), 3.15 (d, J=14.2 Hz, 1H), 3.03 (d, J=12.5 Hz, 1H), 2.66 (m, 1H), 2.50 (m, 1H), 2.00 (m, 1H), 1.80 (m, 1H), 1.27 (d, J=6.9 Hz, 6H), 1.22 (m, 1H)

EXAMPLE 52

Synthesis of Compound 60

Acetone (0.015 mL, 0.20 mmol) and a borane dimethyl sulfide complex (0.0104 mL, 0.11 mmol) were added to a tetrahydrofuran solution (10 mL) of Compound 46 (48 mg, 0.1 mmol), followed by stirring at room temperature for 12 hours. Thereafter, the solvent was evaporated under reduced pressure. The residue was dissolved in methanol (10 mL), and hydrochloric acid (1 mol/l, 2 mL) was added thereto, followed by stirring at 50° C. for 1 hour. The mixture was neutralized with a saturated aqueous solution of sodium hydrogencarbonate and extracted with chloroform. The extract was dried over sodium sulfate, and the solvent was evaporated under reduced pressure. The resulting residue was purified by silica gel column chromatography (eluted with chloroform/methanol=9/1) to obtain Compound 60 (24 mg; yield: 46%).

$^1$H-NMR (CDCl$_3$, 270 MHz) δ 8.52 (s, 1H), 8.47 (d, J=6.9 Hz, 1H), 7.75 (d, J=8.6 Hz, 1H), 7.53 (d, J=7.6 Hz, 1H), 7.42–7.28 (m, 3H), 7.13 (m, 1H), 6.74–6.64 (m, 3H), 4.99 (dd, J=10.9, 9.5 Hz, 1H), 4.11 (m, 1H), 3.90 (d, J=14.2 Hz, 1H), 3.74 (d, J=9.5 Hz, 1H), 3.63 (m, 1H), 2.96 (m, 2H), 2.47 (m, 1H), 2.05 (m, 1H), 1.73 (m, 1H), 1.25 (d, J=6.2 Hz, 3H), 1.17 (d, J=6.2 Hz, 3H)

EXAMPLE 53

Synthesis of Compound 61

Step 1

To a DMF solution (2 mL) of palladium (II) diacetate (2.2 mg, 0.01 mmol) and triphenylphosphine (10.5 mg, 0.04 mmol) were added diethylamine (0.05 mL), N,N-dimethylpropargylamine (0.11 mL, 1.0 mmol), copper (I) iodide (190 mg, 1.0 mmol), and Compound 63 (64 mg, 0.1 mmol) in an argon atmosphere, and the mixture was stirred at room temperature for 1 hour. The reaction mixture was filtered through Celite, and the solvent was evaporated under reduced pressure. The resulting residue was purified by preparative thin layer chromatography (developed with chloroform/methanol=19/1) to obtain a methoxymethyl derivative of Compound 61 (42 mg; yield: 72%).

FAB-MS (m/z): 595, 593 (M+1)

Step 2

Hydrochloric acid (6 mol/l, 1.0 mL) was added to a methanol solution (10 mL) of the methoxymethyl derivative of Compound 61 (34 mg, 0.05 mmol) obtained in step 1, and the mixture was refluxed for 3 hours. The reaction solution was poured into a saturated aqueous solution of sodium hydrogencarbonate and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform/methanol=95/5) and re-precipitated in diethyl ether/hexane to obtain Compound 61 (8.9 mg; yield: 62%).

$^1$H-NMR (CDCl$_3$, 270 MHz) δ 8.49 (br s, 2H), 7.56–7.51 (m, 3H) 7.38–7.26 (m, 4H), 7.09 (dd, J=8.2, 7.3 Hz, 1H), 6.96 (d, J=8.2 Hz, 1H), 4.95 (dd, J=10.9, 10.3 Hz, 1H), 4.04 (m, 1H), 3.81–3.74 (m, 3H), 3.63 (br s, 2H), 3.05–3.00 (m, 2H), 2.50–2.41 (m, 7H), 2.03 (m, 1H), 1.66 (m, 1H)

EXAMPLE 54

Synthesis of Compound 62

Compound 62 (21 mg; yield: 42%) was obtained from Compound V (51 mg, 0.1 mmol) and a borane dimethyl sulfide complex (0.030 mL, 0.5 mmol) in a manner similar to that in Example 1.

$^1$H-NMR (CDCl$_3$, 270 MHz) δ 8.45 (d, J=2.3 Hz, 1H), 7.74–7.50 (m, 2H), 7.48 (d, J=7.6 Hz, 1H), 7.37–7.21 (m, 2H), 7.10–7.03 (m, 3H), 5.05 (dd, J=10.9, 9.2 Hz, 1H), 4.00 (m, 1H), 3.80 (d, J 13.8 Hz, 1H), 3.69 (d, J=10.2 Hz, 1H), 3.02–2.96 (m, 2H), 2.35 (m, 1H), 2.22 (s, 6H), 2.11(m, 1H), 1.86 (m, 1H)

EXAMPLE 55

Synthesis of Compound 63

Compound 63 (18.4 mg; yield: 28%) was obtained from Compound W (65 mg, 0.1 mmol) and a borane dimethyl sulfide complex (0.047 ml, 0.5 mmol) in a manner similar to that in Example 1.

$^1$H-NMR (CDCl$_3$, 270 MHz) δ 8.48–8.46 (m, 2H), 7.94 (br s, 1H), 7.55–7.50 (m, 2H), 7.39–7.21 (m, 3H), 7.10–7.02 (m, 3H), 5.21 (s, 2H), 4.95 (dd, J=10.9, 9.9 Hz, 1H), 4.03 (m, 1H), 3.76 (d, J=8.6 Hz, 2H), 3.49 (s, 3H), 3.48 (d, J=14.3 Hz, 1H), 3.00 (d, J=14.3 Hz, 1H), 2.40 (m, 1H), 2.00 (m, 1H), 1.70 (m, 1H)

EXAMPLE 56

Synthesis of Compound 64

Compound 64 (470 mg; yield: 40%) was obtained from Compound X (1.3 g, 2.0 mmol) and a borane dimethyl sulfide complex (1.85 mL, 10 mmol) in a manner similar to that in Example 1.

$^1$H-NMR (DMSO-d$_6$, 270 MHz) δ 10.45 (br s, 1H), 8.44–8.30 (m, 2H), 7.91 (m, 1H), 7.80 (d, J=7.91 Hz, 1H), 7.57 (d, J=9.4 Hz, 1H), 7.55 (dd, J=8.0, 1.1 Hz, 1H), 7.39–7.30 (m, 3H), 7.16 (m, 1H), 6.85 (d, J=8.0 Hz, 1H), 5.39 (dd, J=11.0, 9.5 Hz, 1H), 3.85 (m, 1H), 3.73 (d, J=9.5 Hz, 1H), 3.55 (d, J=14.0 Hz, 1H), 3.07 (d, J=14.0 Hz, 1H), 2.88 (m, 1H), 2.48 (m, 1H), 1.87–1.72 (m, 2H)

EXAMPLE 57

Synthesis of Compound 65

Compound 65 (47 mg; yield: 39%) was obtained from Compound R (135 mg, 0.26 mmol) and a borane dimethyl sulfide complex (0.95 mL, 10 mmol) in a manner similar to that in Example 1.

$^1$H-NMR (CD$_3$OD, 300 MHz) δ 8.48 (s, 1H), 8.39 (m, 1H), 7.88 (d, J=7.9 Hz, 1H), 7.73 (d, J=6.4 Hz, 1H), 7.53–7.46 (m, 2H), 7.35 (m, 1H), 7.17–7.08 (m, 2H), 6.96–6.86 (m, 2H), 5.13 (dd, J=11.2, 9.7 Hz, 1H), 3.88–3.71 (m, 7H), 3.31–3.07 (m, 2H), 2.95 (dd, J=12.1, 3.5 Hz, 1H), 2.02 (td, J=12.1, 8.9 Hz, 1H)

EXAMPLE 58

Synthesis of Compound 66

An aqueous sodium hydroxide solution (2 mol/l, 1 mL) was added to a tetrahydrofuran (20 mL) solution of Compound 34 (120 mg, 0.021 mmol), and the mixture was stirred at room temperature for 9 hours. After concentration under reduced pressure, the residue was extracted with chloroform and the extract was washed with water. The organic layer was concentrated under reduced pressure, and the crude product was purified by preparative thin layer chromatography (developed with methanol/chloroform=5/95) to obtain Compound 66 (21 mg; yield: 42%).

$[α]^{26}_D$=+57.6° (c=0.12, methanol/chloroform=1/9)

EXAMPLE 59

Synthesis of Compound 67

An aqueous sodium hydroxide solution (2 mol/l, 1 mL) was added to a tetrahydrofuran (20 mL) solution of Compound 35 (130 mg, 0.023 mmol), and the mixture was stirred at room temperature for 9 hours. After concentration under reduced pressure, the residue was extracted with chloroform and the extract was washed with water. The organic layer was concentrated under reduced pressure, and the crude product was purified by preparative thin layer chromatography (developed with methanol/chloroform=5/95) to obtain Compound 67 (29 mg; yield: 58%).

$[α]^{26}_D$=−57.9° (c=0.13, methanol/chloroform=1/9)

EXAMPLE 60

Synthesis of Compound 68

A tetrahydrofuran solution (10 mL) of Compound 57 (52 mg, 0.1 mmol) was added to a tetrahydrofuran suspension (100 mL) of lithium aluminum hydride (20 mg, 0.5 mmol) under cooling with ice, and the mixture was stirred for 12 hours while elevating the temperature to room temperature. The reaction solution was poured into dilute hydrochloric acid, followed by stirring for 10 minutes. The mixture was neutralized with a saturated aqueous solution of sodium hydrogencarbonate and extracted with a chloroform/methanol (9/1) mixed solvent. The extract was dried over sodium sulfate, and the solvent was evaporated under reduced pressure. The resulting residue was purified by preparative thin layer chromatography (developed with chloroform) and re-precipitated in diethyl ether/hexane to obtain Compound 68 (15.2 mg; yield: 31%).

$^1$H-NMR (CDCl$_3$, 270 MHz) δ 9.45 (br s, 1H), 8.65 (br s, 1H), 8.48 (dd, J=4.8, 1.5 Hz, 1H), 7.80 (br s, 1H), 7.59–7.52 (m, 2H), 7.37–7.06 (m, 7H), 4.99 (dd, J=10.8, 9.9 Hz, 1H), 4.05 (m, 1H), 3.89–3.83 (m, 2H), 3.08–3.03 (m, 2H), 2.45 (m, 1H), 2.04 (m, 1H), 1.66 (m, 1H)

EXAMPLE 61

Synthesis of Compound 69

Sulfamoyl chloride (115 mg, 1.0 nmol) was added to an N,N-dimethylacetamide solution (2 mL) of Compound 1 (96 mg, 0.2 mmol), and the mixture was stirred at room temperature for 2 hours. The reaction solution was poured into water, and the powder formed was collected by filtration and purified by preparative thin layer chromatography (developing solvent: chloroform/methanol=9/1) to obtain Compound 69 (45.6 mg; yield: 42%).

$^1$H-NMR (CDCl$_3$, 270 MHz) δ 8.53 (br s, 1H), 8.48 (dd, J=4.8, 1.5 Hz, 1H), 7.74 (br s, 1H), 7.60 (m, 1H), 7.56–7.52 (m, 2H), 7.38–7.23 (m, 3H), 7.22–7.08 (m, 2H), 6.85 (d, J=8.9 Hz, 1H), 6.10 (br s, 1H), 4.98 (dd, J=11.2, 9.8 Hz, 1H), 4.10 (m, 1H), 3.89–3.79 (m, 2H), 3.60–3.25 (m, 2H), 3.20 (m, 1H), 3.03 (d, J=13.9 Hz, 1H), 2.70 (m, 1H), 2.40 (m, 1H), 1.13 (m, 1H)

EXAMPLE 62

Synthesis of Compound 70 and Compound 71

Compound 70 (14.8 g; yield: 13%) and Compound 71 (20.6 mg; yield: 20%) were obtained from Compound 46 (96 mg, 0.2 mmol) and potassium cyanate (162 mg, 2.0 mmol) in a manner similar to that in Example 73 described below.

Compound 70:

$^1$H-NMR (DMSO-d$_6$, 270 MHz) δ 10.15 (br s, 1H), 10.08 (br s, 1H), 9.11 (s, 1H), 8.47 (s, 1H), 8.43 (dd, J=4.6, 1.3 Hz, 1H), 8.27 (br s, 1H), 7.74–7.70 (m, 2H), 7.57 (dd, J=7.9, 1.0 Hz, 1H), 7.39–7.21 (m, 2H), 7.16 (m, 1H), 6.91–6.65 (m, 4H), 5.21 (dd, J=10.6, 8.9 Hz, 1H), 3.88 (m, 1H), 3.72–3.62 (m, 2H), 3.04 (d, J=13.5 Hz, 1H), 2.88 (m, 1H), 2.38 (m, 1H), 1.90–1.65 (m, 2H)

Compound 71:

$^1$H-NMR (DMSO-d$_6$, 270 MHz) δ 10.08 (s, 1H), 8.48 (d, J=1.3 Hz, 1H), 8.44 (dd, J=4.8, 1.4 Hz, 1H), 8.12 (br s, 1H), 8.03 (s, 1H), 7.76–7.71 (m, 2H), 7.57 (dd, J=7.9, 1.0 Hz, 1H), 7.39–7.29 (m, 2H), 7.17 (m, 1H), 6.89 (br S, 1H), 6.67 (d, J=7.9 Hz, 1H), 6.24 (br s, 2H), 5.19 (dd, J=10.9, 9.9 Hz, 1H), 3.88 (m, 1H), 3.69–3.65 (m, 2H), 3.04 (d, J=13.5 Hz, 1H), 2.95 (m, 1H), 2.38 (m, 1H), 1.88–1.68 (m, 2H)

EXAMPLE 63

Synthesis of Compound 72

Compound 72 (33 mg; yield: 26%) was obtained from Compound 46 (96 mg, 0.2 mmol) and sulfamoyl chloride (23 mg, 0.2 mmol) in a manner similar to that in Example 47.

$^1$H-NMR (DMSO-$d_6$, 270 MHz) δ 8.46 (br s, 2H), 8.43 (br s, 1H), 8.35 (br s, 1H), 8.17 (br s, 2H), 7.79–7.69 (m, 2H), 7.69–7.54 (m, 2H), 7.41–7.32 (m, 4H), 7.22–7.16 (m, 2H), 5.44 (dd, J=10.6, 8.9 Hz, 1H), 3.94–3.85 (m, 2H), 3.58 (d, J=13.5 Hz, 1H), 3.07 (d, J=13.5 Hz, 1H), 2.90 (m, 1H), 2.42 (m, 1H), 1.90 (m, 1H), 1.71 (m, 1H)

EXAMPLE 64

Synthesis of Compound 73

Compound 73 (23 mg; yield: 41%) was obtained from Compound 46 (48 mg, 0.1 mmol) and sulfamoyl chloride (11.5 mg, 0.1 mmol) in a manner similar to that in Example 47.

$^1$H-NMR (DMSO-$d_6$, 270 MHz) δ 9.87 (br s, 1H), 8.45 (br s, 2H), 7.87 (br s, 1H), 7.75 (d, J=6.9 Hz, 1H), 7.68 (m, 1H), 7.62–7.59 (m, 2H), 7.39 (m, 1H), 7.31 (m, 1H), 7.21–7.18 (m, 3H), 6.98 (br s, 1H), 6.79 (d, J=7.9 Hz, 1H), 5.38 (dd, J=10.9, 9.6 Hz, 1H), 3.87 (m, 1H), 3.69 (d, J=9.6 Hz, 1H), 3.65 (d, J=14.2 Hz, 1H), 3.03 (d, J=14.2 Hz, 1H), 2.88 (m, 1H), 2.37 (m, 1H), 1.88 (m, 1H), 1.65 (m, 1H)

EXAMPLE 65

Synthesis of Compound 74

Compound 74 (12.5 mg; yield: 12%) was obtained from Compound Y (81 mg, 0.16 mmol) and a borane dimethyl sulfide complex (0.074 mL, 0.78 mmol) in a manner similar to that in Example 1.

$^1$H-NMR (CDCl$_3$, 270 MHz) δ 8.53–8.49 (m, 2H), 7.54–7.52 (m, 2H), 7.39–7.03 (m, 5H), 6.95 (m, 1H), 6.72–6.66 (m, 2H), 5.77 (dd, J=9.2, 8.6 Hz, 1H), 5.09 (br s, 2H), 4.08–3.83 (m, 3H), 3.17 (d, J=13.5 Hz, 1H), 3.09 (dd, J=11.9, 3.0 Hz, 1H), 2.33 (m, 1H), 2.05 (m, 1H), 1.65 (m, 1H)

EXAMPLE 66

Synthesis of Compound 75

Compound 75 (8.8 mg; yield: 11%) was obtained from Compound Z (81 mg, 0.16 mmol) and a borane dimethyl sulfide complex (0.074 mL, 0.78 mmol) in a manner similar to that in Example 1.

$^1$H-NMR (CDCl$_3$, 270 MHz) δ 8.51 (dd, J=4.6, 1.3 Hz, 1H) 8.46 (d, J=1.6 Hz, 1H), 8.22 (dt, J=8.2, 1.0 Hz, 1H), 7.77 (d, J=6.6 Hz, 1H), 7.61–7.53 (m, 4H), 7.36–7.29 (m, 3H), 7.11 (td, J=7.3, 1.1 Hz, 1H), 4.99 (dd, J=10.9, 9.9 Hz, 1H), 4.15–4.00 (m, 2H), 3.78 (d, J=13.8 Hz, 1H), 3.14–3.05 (m, 2H), 2.49 (m, 1H), 2.10 (m, 1H), 1.78 (m, 1H)

EXAMPLE 67

Synthesis of Compound 76

Compound 76 (110 mg; yield: 59%) was obtained from Compound 75 (200 mg, 0.43 mmol) in a manner similar to that in Example 40.

$^1$H-NMR (CDCl$_3$, 270 MHz) δ 8.50–8.46 (m, 2H), 7.60–7.50 (m, 2H), 7.38–7.04 (m, 7H), 6.88 (m, 1H), 6.75 (m, 1H), 6.61 (m, 1H), 5.00 (dd, J=11.2, 9.6 Hz, 1H), 4.05 (m, 1H), 3.88–3.71 (m, 2H), 3.05–2.85 (m, 2H), 2.33 (m, 1H), 2.10 (m, 1H), 1.78 (m, 1H)

EXAMPLE 68

Synthesis of Compound 77

Compound 77 (7.2 mg; yield: 41%) was obtained from Compound 76 (15 mg, 0.032 mmol) and sulfamoyl chloride (3.7 mg, 0.032 mmol) in a manner similar to that in Example 61.

$^1$H-NMR (CDCl$_3$, 270 MHz) δ 8.64 (br s, 1H), 8.46 (br s, 1H) 7.59–7.50 (m, 2H), 7.39 (m, 1H), 7.28–7.20 (m, 2H), 7.07 (m, 1H), 6.74–6.64 (m, 3H), 5.03 (dd, J=11.2, 9.9 Hz, 1H), 4.09–3.91 (m, 2H), 3.73 (m, 1H), 3.30–3.06 (m, 4H), 2.46 (m, 1H), 2.01 (m, 1H), 1.71 (m, 1H), 1.29 (t, J=6.6 Hz, 3H)

EXAMPLE 69

Synthesis of Compound 78

Compound 78 (164 mg; yield: 64%) was obtained from Compound AA (670 mg, 1.56 mmol) and a borane dimethyl sulfide complex (0.74 mL, 7.81 mmol) in a manner similar to that in Example 1.

$^1$H-NMR (CDCl$_3$, 300 MHz) δ 8.59 (br s, 1H), 8.48 (dd, J=5.0, 1.6 Hz, 1H), 8.15 (m, 1H), 7.56 (d, J=7.9 Hz, 1H), 7.37–7.28 (m, 4H), 7.20–7.13 (m, 2H), 6.87 (d, J=8.6 Hz, 2H), 4.97 (dd, J=10.9, 9.6 Hz, 1H), 3.85 (d, J=9.2 Hz, 1H), 3.70 (d, J=5.9 Hz, 1H), 3.65 (m, 1H), 3.09–3.04 (m, 2H), 2.79–2.57 (m, 2H), 2.43 (m, 1H), 1.90 (m, 2H), 1.20 (t, J=7.6 Hz, 3H)

EXAMPLE 70

Synthesis of Compound 79

Concentrated nitric acid (1.0 mL, 25 mmol) was added to an acetic acid solution (20 mL) of Compound 78 (1.7 g, 3.9 mmol) under cooling with ice. The temperature was raised up to room temperature, at which the mixture was stirred for 1 hour. The reaction solution was poured into water, and the mixture was neutralized with a dilute aqueous solution of sodium hydroxide and extracted with a chloroform/methanol (9/1) mixed solvent. The extract was dried over sodium sulfate, and the solvent was removed under reduced pressure. The resulting residue was purified by silica gel column chromatography (eluted with chloroform/methanol= 98/2) to obtain Compound 79 (1.3 g; yield: 69%).

$^1$H-NMR (CDCl$_3$, 270 MHz) δ 8.51 (d, J=3.3 Hz, 1H), 8.47 (br s, 1H), 7.72 (d, J=7.6 Hz, 1H), 7.57 (d, J=7.6 Hz, 1H), 7.32–7.15 (m, 7H), 4.93 (dd, J=11.2, 9.8 Hz, 1H), 3.86 (d, J=9.6 Hz, 1H), 3.76–3.66 (m, 2H), 3.12–3.05 (m, 2H), 2.78–2.57 (m, 2H), 2.43 (m, 1H), 1.95–1.86 (m, 2H), 1.20 (t, J=7.6 Hz, 3H)

EXAMPLE 71

Synthesis of Compound 80

Palladium on carbon (47 mg) was added to a methanol solution (20 mL) of Compound 79 (467 mg, 1.0 mmol) in a nitrogen atmosphere, and the mixture was refluxed for 5 hours. The catalyst was removed by Celite filtration, and the solvent was evaporated under reduced pressure. The resulting residue was purified by silica gel column chromatography (eluted with chloroform/methanol=95/5) to obtain Compound 80 (160 mg; yield: 37%).

$^1$H-NMR (CDCl$_3$, 270 MHz) δ 8.52 (br s, 1H), 8.43 (d, J=4.0 Hz, 1H), 7.58 (d, J=7.9 Hz, 1H), 7.35–7.11 (m, 5H), 6.80–6.61 (m, 3H), 4.98 (dd, J=10.9, 9.9 Hz, 1H), 3.86 (d, J=14.2 Hz, 1H), 3.71–3.63 (m, 2H), 3.07 (d, J=14.2 Hz, 1H), 3.01 (d, J=14.5 Hz, 1H), 2.78–2.55 (m, 2H), 2.40 (m, 1H), 1.90–1.50 (m, 2H), 1.18 (t, J=7.6 Hz, 3H)

EXAMPLE 72

Synthesis of Compound 81

Acetyl chloride (0.014 mL, 0.2 mol) was added to a DMF solution (5 mL) of Compound 80 (86 mg, 0.2 mmol), and the mixture was stirred at room temperature for 1 hour. The reaction solution was poured into water and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform) and re-precipitated in diethyl ether/hexane to obtain Compound 81 (44 mg; yield: 46%).

$^1$H-NMR (CDCl$_3$, 270 MHz) δ 8.51–8.49 (m, 2H), 7.61 (d, J=7.6 Hz, 1H), 7.52 (m, 1H), 7.31–7.13 (m, 5H), 6.94 (d, J=8.2 Hz, 1H), 4.95 (dd, J=10.6, 9.6 Hz, 1H), 3.81 (d, J=13.6 Hz, 1H), 3.73 (d, J=9.6 Hz, 1H), 3.68 (m, 1H), 3.10–3.01 (m, 2H), 2.77–2.58 (m, 2H), 2.41 (m, 1H), 2.23 (s, 3H), 1.90–1.85 (m, 2H), 1.80 (m, 1H), 1.19 (t, J=7.8 Hz, 3H)

EXAMPLE 73

Synthesis of Compound 82

Acetic acid (1.0 mL) and potassium cyanate (162 mg, 2.0 mmol) were added to a tetrahydrofuran solution (10 mL) of Compound 80 (86 mg, 0.2 mmol), and the mixture was stirred at room temperature for 1 hour. The reaction solution was poured into water and the mixture was extracted with a chloroform/methanol (9/1) mixed solvent. The extract was dried over sodium sulfate, and the solvent was evaporated under reduced pressure. The resulting residue was purified by silica gel column chromatography (eluted with chloroform) and re-precipitated in diethyl ether/hexane to obtain Compound 82 (30.4 mg; yield: 32%).

$^1$H-NMR (CDCl$_3$, 270 MHz) δ 8.44 (br s, 1H), 8.36 (br s, 1H) 7.92 (br s, 1H), 7.52 (m, 1H), 7.25–7.09 (m, 4H), 6.94–6.81 (m, 3H), 5.45 (br s, 2H), 4.96 (dd, J=10.8, 9.6 Hz, 1H), 3.77–3.66 (m, 4H), 2.95–2.88 (m, 2H), 2.81–2.50 (m, 2H), 2.34 (m, 1H), 1.84–1.82 (m, 2H), 1.16 (t, J=7.8 Hz, 3H)

Elemental Analysis: C$_{26}$H$_{29}$Cl$_2$N$_5$O$_4$

Found (%): C:65.91, H:6.38, N:14.45

Calcd. (%): C:65.67, H:6.15, N:14.73

EXAMPLE 74

Synthesis of Compound 83

Compound 83 (46 mg; yield: 23%) was obtained from Compound AB (200 mg, 0.41 mmol) in a manner similar to that in Example 1.

$^1$H-NMR (DMSO-d$_6$, 270 MHz) δ 8.63 (br s, 1H), 8.58 (br s, 1H) 8.56 (br s, 1H), 7.81 (d, J=7.9 Hz, 1H), 7.74 (d, J=7.9 Hz, 1H), 7.46 (m, 1H), 7.34–7.26 (m, 3H), 6.93 (br s, 2H), 5.47 (dd, J=10.9, 9.5 Hz, 1H), 3.90 (s, 6H), 3.87 (m, 1H) 3.79–3.71 (m, 2H), 3.23 (d, J=14.2 Hz, 1H), 3.00 (m, 1H), 2.96–2.58 (m, 2H), 2.55 (m, 1H), 1.96–1.87 (m, 2H), 1.26 (t, J=7.6 Hz, 3H)

EXAMPLE 75

Synthesis of Compound 84

Sulfamoyl chloride (79 mg, 0.69 mol) was added to an N,N-dimethylacetamide solution (5 mL) of Compound 80 (200 mg, 0.46 mmol), and the mixture was stirred at room temperature for 15 minutes. The reaction solution was poured into water, and the powder formed was collected by filtration. The resulting crude product was purified by silica gel column chromatography (eluted with chloroform/methanol=98/2) and re-precipitated in diethyl ether/hexane to obtain Compound 84 (62 mg; yield: 26%).

$^1$H-NMR (DMSO-d$_6$, 270 MHz) δ 9.84 (br s, 1H), 8.46–8.43 (m, 2H), 7.98 (br s, 1H), 7.73 (d, J=7.9 Hz, 1H), 7.64–7.53 (m, 2H), 7.32 (dd, J=7.9, 5.0 Hz, 1H), 7.19–7.13 (m, 4H), 7.00 (br s, 1H), 6.81 (d, J=8.3 Hz, 1H), 5.25 (dd, J=10.2, 10.0 Hz, 1H), 3.84–3.72 (m, 2H), 3.16 (d, J=13.5 Hz, 1H), 3.00 (d, J=11.2 Hz, 1H), 2.81–2.51 (m, 3H), 1.94–1.85 (m, 2H), 1.26 (t, J=7.6 Hz, 3H)

EXAMPLE 76

Synthesis of Compound 85

Methanesulfonyl chloride (0.0079 mL, 0.1 mol) was added to an N,N-dimethylacetamide solution (2 mL) of Compound 80 (43 mg, 0.1 mmol), and the mixture was stirred at room temperature for 3 hours. The reaction solution was poured into water, and the powder formed was collected by filtration. The resulting crude product was purified by preparative thin layer chromatography (developed with chloroform/methanol=90/10) and re-precipitated in diethyl ether/hexane to obtain Compound 85 (23 mg; yield: 45%).

$^1$H-NMR (DMSO-d$_6$, 270 MHz) δ 10.02 (br s, 1H), 8.76 (br s, 1H), 8.46–8.43 (m, 2H), 7.68 (d, J=7.6 Hz, 1H), 7.55 (d, J=6.3 Hz, 1H), 7.45 (m, 1H), 7.32 (dd, J=7.6, 4.8 Hz, 1H), 7.20–7.12 (m, 4H), 6.87 (d, J=8.3 Hz, 1H), 5.17 (dd, J=10.9, 9.6 Hz, 1H), 3.72 (d, J=9.6 Hz, 1H), 3.65–3.60 (m, 2H), 3.06 (d, J=13.5 Hz, 1H), 2.92 (s, 3H), 2.85 (m, 1H), 2.69–2.51 (m, 2H), 2.40 (m, 1H), 1.81 (br s, 2H), 1.12 (t, J=7.6 Hz, 3H)

EXAMPLE 77

Synthesis of Compound 86

Compound 86 (1.2 g; yield: 49%) was obtained from Compound AC (2.5 g, 4.2 mmol) in a manner similar to that in Example 1.

$^1$H-NMR (CDCl$_3$, 270 MHz) δ 8.46 (br s, 2H), 7.93 (m, 1H) 7.56 (d, J=7.9 Hz, 1H), 7.34–7.13 (m, 6H), 7.04 (m, 1H) 5.21 (s, 2H), 4.93 (dd, J=11.2, 9.6 Hz, 1H), 3.78–3.61 (m, 3H), 3.47 (s, 3H), 3.04–2.99 (m, 2H), 2.77–2.58 (m, 2H), 2.37 (m, 1H), 1.87–1.82 (m, 2H), 1.92 (m, 1H), 1.19 (t, J=7.6 Hz, 3H)

EXAMPLE 78

Synthesis of Compound 87

Step 1

To a DMF solution (2 mL) of palladium (II) diacetate (5.6 mg, 0.025 mmol) and triphenylphosphine (26 mg, 0.1 mmcol) were added tributylvinyltin (0.073 mL, 0.25 mmol), Compound 86 (168 mg, 0.25 mmol), and triethylamine (0.3 mL) in an argon atmosphere, and the mixture was stirred at 60° C. for 2.5 hours. The reaction mixture was filtered through Celite. Chloroform was added to the filtrate, followed by washing with hydrochloric acid (1 mol/l). The organic layer was neutralized with a saturated aqueous solution of sodium hydrogencarbonate and dried over sodium sulfate. The solvent was evaporated under reduced pressure, and the residue was roughly purified by silica gel column chromatography (eluted with chloroform/methanol= 1/19) to obtain a methoxymethyl derivative of Compound 87 (73 mg; yield: 60%).

Step 2

Hydrochloric acid (1 mol/l, 5 mL) was added to a methanol (20 mL) solution of the methoxymethyl derivative of Compound 87 (70 mg, 0.15 mmcol) obtained in step 1, and the mixture was stirred at 60° C. for 3 hours. The reaction mixture was neutralized with a saturated aqueous solution of sodium hydrogencarbonate and extracted with chloroform. The extract was dried over sodium sulfate, and the solvent was evaporated under reduced pressure. The resulting residue was purified by preparative thin layer chromatography (developed with chloroform/methanol=1/19) to obtain Compound 87 (51 mg; yield: 48%).

$^1$H-NMR (CDCl$_3$, 270 MHz) δ 10.01 (br s, 1H) 8.67 (br s, 1H) 8.59 (br s, 1H), 7.62 (d, J=7.2 Hz, 1H), 7.55–7.14 (m, 8H), 6.95 (d, J=7.6 Hz, 1H), 5.91 (d, J=17.5 Hz, 1H), 5.42 (d, J=11.2 Hz, 1H), 5.11 (m, 1H), 4.01–3.87 (m, 2H), 3.15–3.04 (m, 2H), 2.99 (d, J=14.5 Hz, 1H), 2.85–2.73 (m, 2H), 2.54 (m, 1H), 2.01 (m, 1H), 1.76 (m, 1H), 1.04 (t, J=6.9 Hz, 3H)

EXAMPLE 79

Synthesis of Compound 88

Step 1

To a DMF solution (2 mL) of palladium (II) diacetate (5.6 mg, 0.025 mmol) and triphenylphosphine (26 mg, 0.1 mmol) were added methylvinylsulfone (0.087 mL, 1.0 mmol), Compound 86 (168 mg, 0.25 mmol), and triethylamine (0.3 mL) in an argon atmosphere, and the mixture was stirred at 60° C. for 2 hours. The reaction mixture was filtered through Celite. Chloroform was added to the filtrate, followed by washing with hydrochloric acid (1 mol/l). The organic layer was neutralized with a saturated aqueous solution of sodium hydrogencarbonate and dried over sodium sulfate. The solvent was evaporated under reduced pressure, and the residue was roughly purified by silica gel column chromatography (eluted with chloroform/methanol=1/19) to obtain a methoxymethyl derivative of Compound 88 (68 mg; yield: 48%).

Step 2

Hydrochloric acid (1 mol/l, 5 mL) was added to a methanol (20 mL) solution of the methoxymethyl derivative of Compound 88 (70 mg, 0.15 mmol) obtained in step 1, and the mixture was stirred at 60° C. for 3 hours. The reaction mixture was neutralized with a saturated aqueous solution of sodium hydrogencarbonate and extracted with chloroform. The extract was dried over sodium sulfate, and the solvent was evaporated under reduced pressure. The resulting residue was purified by preparative thin layer chromatography (developed with chloroform/methanol=1/19) to obtain Compound 88 (42 mg; yield: 70%).

$^1$H-NMR (CDCl$_3$, 270 MHz) δ 8.52 (br s, 1H), 8.48 (dd, J=5.0, 1.7 Hz, 1H), 7.74 (d, J=15.5 Hz, 1H), 7.63 (d, J=7.9 Hz, 1H), 7.50 (br s, 1H), 7.38 (d, J=15.5 Hz, 1H), 7.35–7.31 (m, 3H), 7.21–7.13 (m, 3H), 6.95 (d, J=8.5 Hz, 1H), 4.97 (dd, J=10.6, 9.6 Hz, 1H), 3.83 (d, J=15.5 Hz, 1H), 3.74 (d, J=12.9 Hz, 1H), 3.70 (m, 1H), 3.29–3.04 (m, 5H), 2.79–2.44 (m, 3H), 2.00–1.90 (m, 2H), 1.20 (t, J=7.6 Hz, 3H)

EXAMPLE 80

Synthesis of Compound 89

Palladium on carbon (5 mg) was added to a methanol solution (2 mL) of Compound 87 (30 mg, 0.07 mmol) in a hydrogen atmosphere, and the mixture was stirred at 50° C. for 5 hours. The catalyst was removed by Celite filtration, and the solvent was evaporated under reduced pressure. The resulting residue was purified by silica gel thin layer chromatography (developed with chloroform/methanol 1/20) to obtain Compound 89 (16.5 mg; yield: 55%).

$^1$H-NMR (CDCl$_3$, 270 MHz) δ 8.55 (br s, 1H), 8.49 (dd, J=4.9, 1.6 Hz, 1H), 7.57 (d, J=7.6 Hz, 1H), 7.35–7.24 (m, 7H), 6.78 (d, J=8.2 Hz, 1H), 4.97 (dd, J=11.0, 9.7 Hz, 1H), 3.85 (d, J=13.9 Hz, 1H), 3.75–3.65 (m, 2H), 3.08–3.02 (m, 2H), 2.79–2.57 (m, 4H), 2.37 (m, 1H), 1.92 (m, 1H), 1.68 (m, 1H), 1.26–1.20 (m, 6H)

EXAMPLE 81

Synthesis of Compound 90

Step 1

Compound F (437 mg, 0.64 mmol) and concentrated nitric acid (1.0 ml) were treated in a manner similar to that in Example 39 to prepare a nitro compound (300 mg; yield: 64%).

Step 2

Compound 90 (210 mg; yield: 75%) was obtained from the nitro compound (300 mg, 0.64 mmol) obtained in step 1 and a borane dimethyl sulfide complex (0.28 mL, 3.2 mmol) in a manner similar to that in Example 1.

$^1$H-NMR (CDCl$_3$, 300 MHz) δ 8.61 (br S, 1H), 8.48 (d, J=3.3 Hz, 1H), 7.56 (d, J=7.9 Hz, 1H), 7.35–7.13 (m, 6H), 6.83–6.78 (m, 2H), 4.99 (m, 1H), 3.91 (d, J=14.2 Hz, 1H), 3.77 (m, 1H), 3.69 (d, J=9.2 Hz, 1H), 3.09–3.01 (m, 2H), 2.44 (m, 1H), 1.98 (m, 1H), 1.70 (m, 1H)

EXAMPLE 82

Synthesis of Compound 91

Compound 91 (21 mg; yield: 44%) was obtained from Compound 90 (44 mg, 0.1 mmol) and potassium cyanate (81 mg, 1.0 mmol) in a manner similar to that in Example 73.

$^1$H-NMR (DMSO-d$_6$, 270 MHz) δ 10.04 (br S, 1H), 8.46 (br S, 1H), 8.22 (dd, J=4.6, 1.4 Hz, 1H), 8.10 (br s, 1H), 7.73–7.70 (m, 2H), 7.39 (d, J=8.0 Hz, 1H), 7.32–7.21 (m, 5H), 6.76 (d, J=8.0 Hz, 2H), 6.23 (br s, 1H), 5.17 (m, 1H), 3.91 (m, 1H), 3.67 (d, J=9.2 Hz, 1H), 3.65 (d, J=13.7 Hz, 1H), 3.14–2.75 (m, 2H), 2.35 (m, 1H), 1.85–1.65 (m, 2H)

EXAMPLE 83

Synthesis of Compound 92

Compound 92 (37 mg; yield: 82%) was obtained from Compound 80 (43 mg, 0.1 mmol) and methyl chloroformate (0.0077 mL, 0.1 mmol) in a manner similar to that in Example 47.

$^1$H-NMR (CDCl$_3$, 270 MHz) δ 8.51 (br S, 1H), 8.46 (d, J=3.8 Hz, 1H), 7.74 (br S, 1H), 7.63 (d, J=7.8 Hz, 1H), 7.34–7.25 (m, 3H), 7.18–7.08 (m, 3H), 6.88 (d, J=8.1 Hz, 1H), 4.97 (dd, J=11.3, 9.5 Hz, 2H), 3.85 (d, J=13.8 Hz, 1H), 3.82 (s, 3H), 3.72 (d, J=9.5 Hz, 1H), 3.69 (m, 1H), 3.12–3.02 (m, 2H), 2.75–2.59 (m, 2H), 2.42 (m, 1H), 1.94 (t, J=7.6 Hz, 3H), 1.89–1.85 (m, 2H)

EXAMPLE 84

Synthesis of Compound 93

Formaldehyde (0.81 mL, 37 wt % in water, 10 mmol) was added to an acetonitrile solution (10 ml) of Compound 46

(400 mg, 0.83 mmol), and the mixture was stirred at room temperature for 30 minutes. Sodium borohydride (100 mg, 2.6 mmol) was added thereto, and the stirring was continued at the same temperature for 20 minutes. The reaction solution was poured into water, and the mixture was washed with dilute hydrochloric acid, neutralized with an aqueous sodium hydrogencarbonate solution, and extracted with chloroform. The extract was dried over sodium sulfate, and the solvent was evaporated under reduced pressure. The residue was purified by silica gel column chromatography (eluted with chloroform/methanol 99/1) to obtain Compound 93 (203 mg, yield: 48%).

$^1$H-NMR (CDCl$_3$, 270 MHz) δ 8.49 (d, J=2.8 Hz, 2H), 7.53 (d, J=7.9 Hz, 2H), 7.39–7.05 (m, 6H), 6.92 (d, J=8.2 Hz, 1H), 4.94 (dd, J=11.4, 9.9 Hz, 1H), 4.05 (m, 1H), 3.80 (d, J=14.3 Hz, 1H), 3.76 (d, J=10.7 Hz, 1H), 3.04–2.99 (m, 2H), 2.65 (s, 6H), 2.43 (m, 1H), 1.94 (m, 1H), 1.65 (m, 1H)

EXAMPLE 85

Synthesis of Compound 94

Compound 94 (43 mg; yield: 57%) was obtained from Compound AD (78 mg, 0.16 mmol) and a borane dimethyl sulfide complex (0.10 mL, 1.0 mmol) in a manner similar to that in Example 1.

$^1$H-NMR (CDCl$_3$, 300 MHz) δ 8.58 (br s, 1H), 8.48 (br s, 1H) 7.57 (d, J=6.7 Hz, 1H), 7.37–7.16 (m, 7H), 6.86 (d, J=7.8 Hz, 2H), 4.77 (dd, J=10.7, 9.5 Hz, 1H), 3.85 (d, J=13.0 Hz, 1H), 3.72 (d, J=9.5 Hz, 1H), 3.45 (m, 1H), 3.07–3.03 (m, 2H), 2.40 (m, 1H), 1.96 (m, 2H)

EXAMPLE 86

Synthesis of Compound 95

Compound 39 (26 mg, 0.043 mmol) was dissolved in acetonitrile (1.0 mL), and N-methylmorpholine (0.010 mL, 0.091 mmol), diethyl phosphite (0.010 mL, 0.078 mmol) and tetrakistriphenylphosphine palladium (10 mL, 87 pmol) were added thereto, followed by heating under reflux for 8 hours. The reaction mixture was extracted with chloroform (10 mL), and the extract was washed with 1 mol/l hydrochloric acid (10 mL) and dried over anhydrous sodium sulfate. After concentration under reduced pressure, the residue was purified by preparative thin layer chromatography (developed with methanol/chloroform=5/95) to obtain Compound 95 (10 mg; yield: 40%).

$^1$H-NMR (CDCl$_3$, 300 MHz) δ 8.52–8.48 (m, 2H), 7.85 (d, J=7.7 Hz, 1H), 7.81 (d, J=8.3 Hz, 1H), 7.61 (m, 2H), 7.54 (d, J=7.9 Hz, 2H), 7.36–7.22 (m, 3H), 7.10 (m, 1H), 4.98 (t, J=9.3 Hz, 1H), 4.21–4.03 (m, 5H), 3.92 (d, J=9.3 Hz, 1H), 3.70 (d, J=13.8 Hz, 1H), 3.05 (d, J=13.8 Hz, 1H), 2.44 (t, J=11.0 Hz, 1H), 2.06 (br d, J=11.0 Hz, 1H), 1.77–1.69 (m, 2H), 1.31 (t, J=7.1 Hz, 6H)

EXAMPLE 87

Synthesis of Compound 96

Compound 95 (2.0 mg, 0.00034 mmol) was dissolved in hydrochloric acid (12 mol/l, 2.0 mL), and the solution was stirred at 80° C. for 8 hours, followed by concentration under reduced pressure to obtain Compound 96 (1.0 mg; yield: 55%).

$^1$H-NMR (CD$_3$OD, 300 MHz) δ 8.76–8.48 (m, 2H), 8.56 (d, J=8.1 Hz, 1H), 8.00 (m, 1H), 7.81–7.50 (m, 6H), 7.35 (m, 1H), 7.17 (m, 1H), 5.43 (t, J=7.3 Hz, 1H), 4.21–4.15 (m, 2H), 4.02 (t, J=7.3 Hz, 1H), 3.87 (d, J=15.0 Hz, 1H), 3.67 (t, J=15.0 Hz, 1H), 3.17 (m, 1H), 2.82 (m, 1H), 2.05 (m, 1H)

EXAMPLE 88

Synthesis of Compound 97

Benzaldehyde (0.010 mL, 0.10 mmol) and sodium triacetoxyborohydride (212 mg, 1.0 mmol) were added to a tetrahydrofuran solution (10 mL) of Compound 80 (23 mg, 0.05 mmol), and the mixture was stirred at room temperature for 12 hours. The reaction solution was poured into water, and the mixture was neutralized with a saturated aqueous solution of sodium hydrogencarbonate and extracted with chloroform. The extract was dried over sodium sulfate, and the solvent was evaporated under reduced pressure. The resulting residue was purified by silica gel column chromatography (eluted with chloroform/methanol=9/1) to obtain Compound 97 (16 mg; yield: 61%).

$^1$H-NMR (CDCl$_3$, 270 MHz) δ 8.55 (br s, 1H), 8.45 (d, J=4.0 Hz, 1H), 7.50 (d, J=7.9 Hz, 1H), 7.43–7.11 (m, 10H), 6.87–6.66 (m, 3H), 4.92 (dd, J=10.5, 9.9 Hz, 1H), 4.38 (s, 2H), 3.85 (d, J=13.5 Hz, 1H), 3.67–3.64 (m, 2H), 3.06–2.97 (m, 2H), 2.80–2.52 (m, 2H), 2.37 (m, 1H), 1.90–1.85 (m, 2H), 1.18 (t, J=7.6 Hz, 3H)

EXAMPLE 89

Synthesis of Compound 98

Compound 98 (14 mg; yield: 48%) was obtained from Compound AE (30 mg, 0.064 mmol) in a manner similar to that in Example 1.

$^1$H-NMR (CDCl$_3$, 270 MHz) δ 8.51–8.42 (m, 2H), 7.58–7.52 (m, 2H), 7.40–7.18 (m, 6H), 7.10 (m, 1H), 5.00 (dd, J=11.5, 10.8 Hz, 1H), 4.05–3.96 (m, 2H), 3.81 (d, J=13.8 Hz, 1H), 3.08 (d, J=13.8 Hz, 1H), 2.98 (m, 1H), 2.40 (m, 1H), 2.03 (m, 1H), 1.68 (m, 1H)

EXAMPLE 90

Synthesis of Compound 99 and Compound 100

Compound 98 (200 mg) was optically resolved by high performance liquid chromatography (HPLC) (Chiralcel OD column (diameter: 2 cm; length: 25 cm); eluent: isopropyl alcohol/n-hexane/diethylamine=20/80/0.1; flow rate: 5 mL/min; detection: UV 254 nm) to obtain Compound 99 (15.9 mg; >99% e.e.; yield: 21%) that is the (+)-form of Compound 98 and Compound 100 (12.4 mg; 92% e.e.; yield: 17%) that is the (−)-form of Compound 98.

Compound 99: $[\alpha]^{26}_D$=+25.9° (c=0.15, methanol)
Compound 100: $[\alpha]^{26}_D$=−24.6° (c=0.10, methanol)

EXAMPLE 91

Synthesis of Compound 101

Compound 101 (14 mg; yield: 48%) was obtained from Compound AF (30 mg, 0.064 mmol) in a manner similar to that in Example 1.

$^1$H-NMR (CDCl$_3$, 270 MHz) δ 8.72 (d, J=4.6 Hz, 1H), 8.49 (dd, J=4.6, 1.8 Hz, 1H), 8.44 (d, J=1.8 Hz, 1H), 8.11 (td, J=7.4, 1.8 Hz, 1H), 7.59 (d, J=7.9 Hz, 1H), 7.52 (dd, J=8.2, 1.0 Hz, 1H), 7.40 (m, 1H), 7.29–7.21 (m, 4H), 7.08 (m, 1H), 5.37 (dd, J=11.2, 9.9 Hz, 1H), 4.11–4.03 (m, 2H), 3.61 (d, J=13.5 Hz, 1H), 3.20 (d, J=13.5 Hz, 1H), 2.52 (m, 1H), 2.08–2.01 (m, 2H), 1.81 (m, 1H)

Elemental Analysis: $C_{22}H_{21}BrN_4O_2$
Found (%): C:58.32, H:4.90, N:12.37
Calcd. (%): C:58.29, H:4.67, N:12.36

EXAMPLE 92

Synthesis of Compound 102

Compound 102 (53 mg; yield: 57%) was obtained from Compound AG (100 mg, 0.064 mmol) in a manner similar to that in Example 1.

$^1$H-NMR (DMSO-$d_6$, 270 MHz) δ 9.05 (s, 1H), 9.02 (s, 1H), 8.42 (m, 2H), 7.62 (d, J=7.6 Hz, 1H), 7.44 (dd, J=4.7, 3.3 Hz, 1H), 7.33 (br s, 2H), 7.11 (d, J=4.7 Hz, 1H), 6.88 (m, 1H), 6.69 (m, 2H), 4.85 (t, J=10.2 Hz, 1H), 3.64–3.40 (m, 3H), 3.01 (d, J=13.5 Hz, 1H), 2.83 (d, J=11.5 Hz, 1H), 2.29 (m, 1H), 1.95–1.86 (m, 2H)

EXAMPLE 93

Synthesis of Compound 103

Compound 103 (12 mg; yield: 62%) was obtained from Compound AH (30 mg, 0.064 mmol) in a manner similar to that in Example 1.

$^1$H-NMR (CDCl$_3$, 270 MHz) δ 8.76 (br s, 1H), 8.60 (dd, J=4.5, 1.5 Hz, 1H), 8.51 (d, J=3.3 Hz, 1H), 8.47 (br s, 1H), 7.82 (br d, J=7.9 Hz, 1H), 7.55 (br d, J=7.9 Hz, 1H), 7.36–7.23 (m, 5H), 7.11 (m, 1H), 4.79 (d, J=9.4 Hz, 1H), 4.70 (dt, J=11.2, 9.6 Hz, 1H), 3.31 (m, 1H), 2.05–1.89 (m, 3H)

EXAMPLE 94

Synthesis of Compound 104

Compound 104 (29.5 mg; yield: 30%) was obtained from Compound AI (100 mg, 0.19 mmol) in a manner similar to that in Example 1.

$^1$H-NMR (DMSO-$d_6$, 270 MHz) δ 8.49 (br s, 1H), 8.44 (d, J=5.3 Hz, 1H), 7.73 (d, J=6.9 Hz, 1H), 7.70 (d, J=7.9 Hz, 1H), 7.57 (d, J=8.2 Hz, 1H), 7.42–7.14 (m, 4H), 6.98 (d, J=6.3 Hz, 1H), 5.24 (dd, J=10.6, 9.6 Hz, 1H), 4.20 (d, J=9.6 Hz, 1H), 3.85 (m, 1H), 3.79 (d, J=14.2 Hz, 1H), 3.10 (d, J=14.2 Hz, 1H), 2.85 (m, 1H), 2.45 (m, 1H), 1.78 (m, 2H)

EXAMPLE 95

Synthesis of Compound 105

Compound 105 (11 mg; yield: 42%) was obtained from Compound 80 (23 mg, 0.05 mmol) and 4-fluorobenzaldehyde (0.011 mg, 0.10 mmol) in a manner similar to that in Example 88.

$^1$H-NMR (CDCl$_3$, 270 MHz) δ 8.55 (br s, 1H), 8.46 (d, J=3.6 Hz, 1H), 7.48 (d, J=7.9 Hz, 1H), 7.39–7.11 (m, 7H), 7.08–6.99 (m, 2H), 6.63 (br s, 1H), 4.89 (dd, J=10.6, 9.4 Hz, 1H), 3.85 (d, J=13.8 Hz, 1H), 3.66–3.62 (m, 2H), 3.06–2.98 (m, 2H), 2.77–2.55 (m, 2H), 2.39 (m, 1H), 1.85–1.80 (m, 2H), 1.19 (t, J=7.6 Hz, 3H)

Compound 106 and Compounds 108 to 113 were synthesized in a manner similar to that in Example 88.

EXAMPLE 96

Synthesis of Compound 107

Compound 107 (14 mg; yield: 52%) was obtained from Compound 80 (23 mg, 0.05 mmol) and 2-thiophenecarboxaldehyde (0.0094 mL, 0.10 mmol) in a manner similar to that in Example 88.

$^1$H-NMR (CDCl$_3$, 270 MHz) δ 8.56 (br s, 1H), 8.45 (d, J=4.3 Hz, 1H), 7.53 (d, J=7.9 Hz, 1H), 7.26–7.13 (m, 7H), 7.13 (m, 1H), 6.96 (dd, J=4.6, 3.6 Hz, 1H), 6.75 (br s, 1H), 4.96 (dd, J=10.6, 10.2 Hz, 1H), 4.56 (br s, 2H), 3.87 (d, J=13.5 Hz, 1H), 3.70–3.66 (m, 2H), 3.09–3.04 (m, 2H), 2.78–2.55 (m, 2H), 2.40 (m, 1H), 1.89–1.85 (m, 2H), 1.19 (t, J=7.4 Hz, 3H)

EXAMPLE 97

Synthesis of Compound 114

Compound 114 (3.0 mg; yield: 17%) was obtained from Compound AJ (18 mg, 0.0395 mmol) in a manner similar to that in Example 1.

$^1$H-NMR (CDCl$_3$, 270 MHz) δ 10.74 (br s, 1H), 8.61 (br s, 1H) 8.56 (dd, J=4.8, 1.5 Hz, 1H), 7.62 (d, J=7.9 Hz, 1H), 7.51 (d, J=7.6 Hz, 1H), 7.33–7.01 (m, 6H), 5.32 (dd, J=11.2, 10.6 Hz, 1H), 4.25 (d, J=10.6 Hz, 1H), 4.04 (m, 1H), 3.68 (d, J=13.8 Hz, 1H), 3.33 (d, J=13.8 Hz, 1H), 3.03 (m, 1H), 2.52 (m, 1H), 2.03 (m, 1H), 1.70 (m, 1H)

EXAMPLE 98

Synthesis of Compound 115

Compound 115 (18.4 mg; yield: 38%) was obtained from Compound AK (50 mg, 0.099 mmol) in a manner similar to that in Example 1.

$^1$H-NMR (DMSO-$d_6$, 270 MHz) δ 11.12 (br s, 1H), 8.43–8.37 (m, 2H), 7.74 (d, J=7.9 Hz, 1H), 7.63–7.55 (m, 2H), 7.40–7.15 (m, 8H), 5.50 (dd, J=10.2, 8.9 Hz, 1H), 4.13 (m, 1H), 3.95 (m, 1H), 3.71 (d, J=13.9 Hz, 1H), 3.16 (d, J=13.9 Hz, 1H), 2.90 (m, 1H), 2.45 (m, 1H), 1.93–1.85 (m, 2H)

EXAMPLE 99

Synthesis of Compound 116

Compound 116 (10.1 mg; yield: 30%) was obtained from Compound AL (36 mg, 0.077 mmol) in a manner similar to that in Example 1.

$^1$H-NMR (CDCl$_3$, 270 MHz) δ 8.49–8.46 (br s, 2H), 7.70–7.68 (m, 2H), 7.51 (d, J=7.9 Hz, 1H), 7.39 (d, J=7.9 Hz, 1H), 7.29–7.22 (m, 4H), 7.09–7.03 (m, 2H), 5.36 (dd, J=10.5, 9.6 Hz, 1H), 4.04 (m, 1H), 4.01 (m, 1H), 3.98 (d, J=9.6 Hz, 1H), 3.85 (d, J=13.5 Hz, 1H), 3.20 (d, J=13.5 Hz, 1H), 3.03 (m, 1H), 2.52 (m, 1H), 2.01 (m, 1H), 1.72 (m,

EXAMPLE 100

Synthesis of Compound 117

Compound 117 (10.1 mg; yield: 9.7%) was obtained from Compound AM (107 mg, 0.24 mmol) in a manner similar to that in Example 1.

$^1$H-NMR (CDCl$_3$, 270 MHz) δ 8.74 (br s, 1H), 8.62 (dd, J=4.9, 1.6 Hz, 1H), 8.51 (dd, J 4.9, 1.6 Hz, 1H), 8.49 (d, J=2.0 Hz, 1H), 7.83 (d, J=7.9 Hz, 1H), 7.55 (d, J=7.9 Hz, 2H), 7.36–7.22 (m, 3H), 7.11 (m, 1H), 5.00 (dd, J=10.9, 9.6 Hz, 1H), 4.10 (m, 1H), 3.92 (d, J=9.6 Hz, 1H), 3.71 (d, J=13.5 Hz, 1H), 3.13–3.06 (m, 2H), 2.45 (m, 1H), 2.08 (m, 1H), 1.75 (m, 1H)

EXAMPLE 101

Synthesis of Compound 118

Compound 118 (67 mg; yield: 68%) was obtained from Compound AN (102 mg, 0.20 mmol) in a manner similar to that in Example 1.

¹H-NMR (CDCl₃, 270 MHz) δ 8.50–8.49 (m, 2H), 7.58–7.51 (m, 2H), 7.37–7.22 (m, 3H), 7.12–7.04 (m, 2H), 6.85–6.76 (m, 2H), 5.97 (s, 2H), 4.95 (dd, J=11.2, 9.5 Hz, 1H), 4.04 (m, 1H), 3.83 (d, J=13.9 Hz, 1H), 3.77 (d, J=9.5 Hz, 1H), 3.06–3.01 (m, 2H), 2.40 (m, 1H), 2.06 (m, 1H), 1.69 (m, 1H)

EXAMPLE 102

Synthesis of Compound 119

Compound 119 (0.7 mg; yield: 8.9%) was obtained from Compound AO (8.0 mg, 0.016 mmol) in a manner similar to that in Example 1.

¹H-NMR (CDCl₃, 270 MHz) δ 8.49–8.47 (m, 2H), 8.06 (br s, 1H), 7.78–7.67 (m, 2H), 7.59–7.48 (m, 3H), 7.35 (m, 1H), 7.28–7.20 (m, 3H), 7.08 (m, 1H), 5.08 (dd, J=10.8, 9.2 Hz, 1H), 4.09 (m, 1H), 3.99 (d, J=9.2 Hz, 1H), 3.80 (d, J=13.9 Hz, 1H), 3.09–3.04 (m, 2H), 2.45 (m, 1H), 2.08 (m, 1H), 1.75 (m, 1H)

EXAMPLE 103

Synthesis of Compound 120

Compound 120 (11.7 mg; yield: 60%) was obtained from Compound AP (20.0 mg, 0.041 mmol) in a manner similar to that in Example 1.

¹H-NMR (CDCl₃, 270 MHz) δ 8.51 (br s, 1H), 8.47 (d, J=3.3 Hz, 1H), 7.72 (m, 1H), 7.61 (d, J=7.6 Hz, 1H), 7.53 (d, J=7.9 Hz, 1H), 7.44 (dd, J=6.2, 2.0 Hz, 1H), 7.35 (d, J=7.6 Hz, 1H), 7.31–7.19 (m, 2H), 7.09 (m, 1H), 6.35 (dd, J=6.9, 6.2 Hz, 1H), 5.38 (br s, 1), 4.28 (br s, 1H), 4.08 (m, 1H), 3.85 (d, J=13.9 Hz, 1H), 3.23 (d, J=13.9 Hz, 1H), 3.03 (m, 1H), 2.45 (m, 1H), 2.01 (m, 1H), 1.85 (m, 1H)

EXAMPLE 104

Synthesis of Compound 121

Compound 121 (11.7 mg; yield: 60%) was obtained from Compound AQ (19.0 mg, 0.039 mmol) in a manner similar to that in Example 1.

¹H-NMR (CDCl₃, 270 MHz) δ 8.53–8.50 (m, 2H), 7 73 (d, J=7.3 Hz, 1H), 7.53 (d, J=7.9 Hz, 1H), 7.32–7.23 (m, 4H), 7.10 (m, 1H), 6.68 (d, J=9.5 Hz, 1H), 4.89 (dd, J=10.6, 9.6 Hz, 1H), 3.89 (m, 1H), 3.87 (d, J=13.9 Hz, 1H), 3.65 (d, J=9.6 Hz, 1H), 3.09 (d, J=13.9 Hz, 1H), 3.03 (m, 1H), 2.38 (m, 1H), 2.05 (m, 1H), 1.80 (m, 1H)

EXAMPLE 105

Synthesis of Compound 122

Compound 122 (78 mg; yield: 54%) was obtained from Compound AR (150 mg, 0.32 mmol) in a manner similar to that in Example 1.

¹H-NMR (CDCl₃, 270 MHz) δ 8.54 (s, 1H), 8.50 (d, J=4.3 Hz, 1H), 7.66 (d, J=7.6 Hz, 1H), 7.52 (d, J=7.9 Hz, 1H), 7.37–7.22 (m, 4H), 7.15–7.08 (m, 2H), 6.92 (m, 1H), 5.01 (dd, J=10.8, 9.8 Hz, 1H), 4.24 (d, J=9.8 Hz, 1H), 3.97 (d, J=13.7 Hz, 1H), 3.08 (d, J=13.7 Hz, 1H), 3.01 (m, 1H), 2.42 (m, 1H), 1.99 (m, 1H), 1.69 (m, 1H)

EXAMPLE 106

Synthesis of Compound 123

Compound 123 (80 mg; yield: 18%) was obtained from Compound AS (190 mg, 0.41 mmol) in a manner similar to that in Example 1.

¹H-NMR (CDCl₃, 270 MHz) δ 8.74 (br s, 1H), 8.61 (m, 1H) 8.52–8.48 (m, 2H), 7.83 (d, J=7.9 Hz, 1H), 7.54 (d, J=7.9 Hz, 2H), 7.38–7.22 (m, 4H), 7.09 (m, 1H), 5.01 (dd, J=10.8, 9.8 Hz, 1H), 4.08 (m, 2H), 3.93 (d, J=9.5 Hz, 1H), 3.70 (d, J=13.4 Hz, 1H), 3.11–3.06 (m, 2H), 2.46 (m, 1H), 2.07 (m, 1H), 1.70 (m, 1H)

EXAMPLE 107

Synthesis of Compound 124

Compound 124 (437 mg; yield: 53%) was obtained from Compound AT (854 mg, 2.0 mmol) and a borane dimethyl sulfide complex (0.57 ml, 6 mmol) in a manner similar to that in Example 1.

¹H-NMR (DMSO-d₆, 300 MHz) δ 8.46–8.44 (m, 2H), 7.81 (d, J=7.9 Hz, 1H), 7.70–7.63 (m, 2H), 7.40–7.31 (m, 3H), 7.01–6.96 (m, 3H), 5.26 (dd, J=10.4, 10.2 Hz, 1H), 3.76–3.61 (m, 3H), 3.06 (d, J=13.9 Hz, 1H), 2.89 (dd, J=11.2, 2.4 Hz, 1H), 2.34 (m, 1H), 1.82 (m, 1H), 1.67 (m, 1H)

EXAMPLE 108

Synthesis of Compound 125

Compound 125 (80 mg; yield: 18%) was obtained from Compound AU (180 mg, 0.41 mmol) in a manner similar to that in Example 1.

¹H-NMR (CDCl₃, 270 MHz) δ 8.50 (s, 1H) 8.49 (d, J=2.0 Hz, 1H), 7.60 (dt, J=7.5, 1.9 Hz, 1H), 7.50 (dd, J=7.9, 1.1 Hz, 1H), 7.46 (d, J=1.3 Hz, 1H), 7.38 (d, J=7.3 Hz, 1H), 7.31–7.20 (m, 4H), 7.07 (td, J=7.3, 1.8 Hz, 1H), 6.41 (dd, J=3.1, 1.0 Hz, 1H), 6.32 (dd, J=3.1, 1.0 Hz, 1H), 5.28 (dd, J=10.9, 9.8 Hz, 1H), 4.04–3.98 (m, 2H), 3.71 (d, J=13.9 Hz, 1H), 3.18 (d, J=13.9 Hz, 1H), 3.00 (td, J=8.2, 3.0 Hz, 1H), 2.42 (m, 1H), 2.05 (m, 1H), 1.68 (m, 1H)

EXAMPLE 109

Synthesis of Compound 126

Compound 126 (9.4 mg; yield: 40%) was obtained from Compound AV (25 mg, 0.05 mmol) and a borane dimethyl sulfide complex (0.014 ml, 0.15 mmol) in a manner similar to that in Example 1.

¹H-NMR (DMSO-d₆, 300 MHz) δ 9.24 (s, 1H), 8.95 (br s, 1H) 8.45 (m, 1H), 7.81 (d, J=7.9 Hz, 1H), 7.67 (m, 1H), 7.40–7.31 (m, 3H), 7.01–6.96 (m, 3H), 5.26 (dd, J=10.4, 10.2 Hz, 1H), 3.76–3.61 (m, 3H), 3.06 (d, J=13.9 Hz, 1H), 2.89 (dd, J=11.2, 2.4 Hz, 1H), 2.34 (m, 1H), 1.82 (m, 1H), 1.67 (m, 1H)

EXAMPLE 110

Synthesis of Compound 127

Compound 127 (95 mg; yield: 51%) was obtained from Compound AW (191 mg, 0.4 mmol) and a borane dimethyl sulfide complex (0.113 mL, 1.2 mmol) in a manner similar to that in Example 1.

¹H-NMR (CDCl₃, 300 MHz) δ 8.50 (dd, J=4.6, 1.3 Hz, 1H) 8.47 (d, J=1.7 Hz, 1H), 7.55 (d, J=7.6 Hz, 1H), 7.38 (dd, J=4.9, 3.0 Hz, 1H), 7.26–7.22 (m, 3H), 6.85 (d, J=3.6 Hz, 1H), 6.60 (d, J=3.6 Hz, 1H), 4.65 (dd, J=10.9, 9.6 Hz, 1H), 3.92 (d, J=9.6 Hz, 1H), 3.78 (d, J=13.9 Hz, 1H), 3.57 (m, 1H), 3.06–3.01 (m, 2H), 2.31 (m, 1H), 2.10 (m, 1H), 1.92 (m, 1H)

EXAMPLE 111

Synthesis of Compound 128

Compound 128 (420 mg; yield: 49%) was obtained from Compound AX (890 mg, 2.1 mmol) and a borane dimethyl sulfide complex (0.95 mL, 10 mmol) in a manner similar to that in Example 1.

$^1$H-NMR (CDCl$_3$, 300 MHz) δ 8.51 (d, J=1.5 Hz, 1H), 8.49 (d, J=1.8 Hz, 1H), 7.55 (m, 1H), 7.39 (dd, J=5.1, 2.8 Hz, 1H), 7.31–7.11 (m, 7H), 4.98 (dd, J=11.4, 9.4 Hz, 1H), 3.99 (d, J=9.4 Hz, 1H), 3.81 (d, J=13.9 Hz, 1H), 3.68 (m, 1H), 3.08 (d, J=13.9 Hz, 1H), 3.04 (m, 1H), 2.81–2.53 (m, 2H), 2.38 (m, 1H), 1.92–1.87 (m, 2H), 1.22 (t, J=7.6 Hz, 3H)

EXAMPLE 112

Synthesis of Compound 129 and Compound 130

Compound 128 (200 mg) was optically resolved by high performance liquid chromatography (HPLC) (Chiralcel OD column (diameter: 2 cm; length: 25 cm); eluent: ethanol/n-hexane/diethylamine=33/66/0.1; flow rate: 5 mL/min; detection: UV 254 nm) to obtain Compound 129 (21 mg; 94% e.e.; yield: 31%) that is the (+)-form of Compound 128 and Compound 130 (28 mg; >99% e.e.; yield: 130 (28 mg; >99% e.e.; yield: 43%) that is the (–)-form of Compound 128.
Compound 129: $[\alpha]^{26}_D$=+13.2° (c=0.10, methanol)
Compound 130: $[\alpha]^{26}_D$=–13.9° (c=0.17, methanol)

EXAMPLE 113

Synthesis of Compound 131

Compound 131 (65 mg; yield: 67%) was obtained from Compound AY (100 mg, 2.0 mmol) and a borane dimethyl sulfide complex (0.57 ml, 6 mmol) in a manner similar to that in Example 1.

$^1$H-NMR (CDCl$_3$, 300 MHz) δ 8.51–8.47 (m, 2H), 7.57 (d, J=7.7 Hz, 1H), 7.37 (dd, J=4.8, 3.1 Hz, 1H), 7.26–7.24 (m, 4H), 6.71 (d, J=5.5 Hz, 1H), 4.70 (dd, J=11.0, 9.6 Hz, 1H), 3.97 (d, J=9.6 Hz, 1H), 3.82–3.73 (m, 2H), 3.08–2.89 (m, 2H), 2.34 (s, 3H), 2.08–1.85 (m, 2H)

EXAMPLE 114

Synthesis of Compound 132

Compound 132 (196 mg; yield: 51%) was obtained from Compound AZ (409 mg, 1.0 mmol) and a borane dimethyl sulfide complex (0.57 mL, 6 mmol) in a manner similar to that in Example 1.

$^1$H-NMR (CDCl$_3$, 300 MHz) δ 8.54 (d, J=1.8 Hz, 1H), 8.48 (dd, J=5.0, 1.8 Hz, 1H), 7.95 (br s, 1H), 7.57 (d, J=7.7 Hz, 1H), 7.32–7.26 (m, 4H), 7.10 (d, J=5.3 Hz, 1H), 6.84 (d, J=5.3 Hz, 1H), 6.70 (d, J=6.1 Hz, 1H), 4.69 (dd, J=11.2, 9.5 Hz, 1H), 3.85–3.72 (m, 3H), 3.06–3.00 (m, 2H), 2.40 (m, 1H), 2.13 (s, 3H), 2.07–1.87 (m, 2H)

EXAMPLE 115

Synthesis of Compound 133

Compound 133 (60 mg; yield: 52%) was obtained from Compound BA (100 mg, 0.21 mmol) and a borane dimethyl sulfide complex (0.57 mL, 6 mmol) in a manner similar to that in Example 1.

$^1$H-NMR (CDCl$_3$, 300 MHz) δ 8.51 (d, J=1.6 Hz, 1H), 8.48 (d, J=2.1 Hz, 1H), 7.76 (d, J=8.4 Hz, 1H), 7.38 (dd, J=4.9, 3.1 Hz, 1H), 7.28–7.22 (m, 5H), 4.83 (dd, J=11.4, 9.4 Hz, 1H), 4.00 (d, J=9.4 Hz, 1H), 3.93 (m, 1H), 3.80 (d, J=13.8 Hz, 1H), 3.18–2.99 (m, 2H), 2.38 (m, 1H), 2.11–1.86 (m, 2H)

EXAMPLE 116

Synthesis of Compound 134

4-Cyanobenzyl bromide (0.078 mL, 0.4 mmol) was added to an acetonitrile solution (5 mL) of Compound 46 (96 mg, 0.2 mmol), and the mixture was stirred at 60° C. for 1.5 days. The solvent was evaporated under reduced pressure, and the residue was purified by preparative thin layer chromatography (developing solvent: chloroform:methanol=19:1) to obtain Compound 134 (8.2 mg; yield: 6.9%).

$^1$H-NMR (CDCl$_3$, 300 MHz) δ 8.47–8.03 (m, 2H), 7.62 (d, J=8.2 Hz, 2H), 7.53–7.47 (m, 4H), 7.29–7.25 (m, 3H), 7.07 (m, 1H), 6.80 (br s, 2H), 6.45 (br s, 1H), 4.96 (m, 1H), 4.54–4.41 (m, 2H), 3.99 (m, 1H), 3.85 (m, 1H), 3.65 (d, J=9.6 Hz, 1H), 3.22–2.97 (m,2H), 2.43 (m, 1H), 1.99 (m, 1H), 1.67 (m, 1H)

EXAMPLE 117

Synthesis of Compound 135

Compound 135 (24 mg; yield: 65%) was obtained from Compound BB (32 mg, 0.08 mmol) and a borane dimethyl sulfide complex (0.057 mL, 0.6 mmol) in a manner similar to that in Example 1.

$^1$H-NMR (CDCl$_3$, 300 MHz) δ 8.50–8.46 (m, 2H), 7.56 (d, J=7.9 Hz, 1H), 7.37 (dd, J=4.3, 3.6 Hz, 1H), 7.25–7.21 (m, 3H), 6.45 (m, 1H), 6.06–6.03 (m, 2H), 4.75 (dd, J=10.9, 9.6 Hz, 1H), 3.92 (d, J=9.6 Hz, 1H), 3.79 (d, J=13.8 Hz, 1H), 3.51 (s, 3H), 3.43 (m, 1H), 3.05 (d, J=13.5 Hz, 1H), 2.97 (m, 1H), 2.31 (m, 1H), 2.04–1.71 (m, 2H)

EXAMPLE 118

Synthesis of Compound 136 and Compound 137

Compound 136 (21 mg; yield: 12%) and Compound 137 (74 mg; yield: 40%) were obtained from a Compound BC/Compound BD mixture (96 mg, 0.23 mmol) and a borane dimethyl sulfide complex (0.095 mL, 1.0 mmol) in a manner similar to that in Example 1

Compound 136:

$^1$H-NMR (CDCl$_3$, 270 MHz) δ 8.66 (d, J=2.0 Hz, 1H), 8.61 (dd, J=4.9, 1.7 Hz, 1H), 8.46 (dd, J=4.9, 1.3 Hz, 1H), 8.39 (d, J=1.9 Hz, 1H), 7.76 (dt, J=7.9, 1.7 Hz, 1H), 7.47 (dt, J=7.9, 1.7 Hz, 1H), 7.35–7.17 (m, 7H), 4.50 (dd, J=10.2, 9.7 Hz, 1H), 3.73 (d, J=9.7 Hz, 1H), 3.62 (d, J=13.8 Hz, 1H), 2.97 (d, J=13.8 Hz, 1H), 2.90 (m, 1H), 2.75 (m, 1H), 2.45–2.11 (m, 2H), 2.06 (m, 1H), 1.75–1.65 (m, 2H), 1.35 (m, 1H)

Compound 137:

$^1$H-NMR (CDCl$_3$, 270 MHz) δ 8.51 (br s, 1H), 8.48 (dd, J=4.7, 1.1 Hz, 1H), 7.51 (d, J=7.9 Hz, 1H), 7.30–7.09 (m, 8H), 6.85 (d, J=8.6 Hz, 1H), 4.50 (dd, J=9.9, 9.6 Hz, 1H), 3.78 (d, J=14.2 Hz, 1H), 3.61 (d, J=9.6 Hz, 1H), 2.96 (d, J=14.2 Hz, 1H), 2.88–2.71 (m, 2H), 2.43–2.30 (m, 2H), 2.12 (m, 1H), 2.06 (m, 1H), 1.70 (m, 1H), 1.35 (m, 1H)

EXAMPLE 119

Synthesis of Compound 138

Compound 138 (27 mg; yield: 10%) was obtained from Compound BE (274 mg, 0.6 mmol) and a borane dimethyl sulfide complex (0.19 mg, 2.0 mmol) in a manner similar to that in Example 1.

$^1$H-NMR (CDCl$_3$, 270 MHz) δ 8.51–8.49 (m, 2H), 7.58–7.22 (m, 7H), 7.10 (m, 1H), 6.61 (d, J=1.0 Hz, 1H), 4.95 (dt, J=11.2, 9.7 Hz, 1H), 4.06–3.88 (m, 3H), 3.04 (d, J=13.7 Hz, 1H), 2.98 (m, 1H), 2.38 (m, 1H), 2.01 (m, 1H), 1.66 (m, 1H)

EXAMPLE 120

Synthesis of Compound 139

Compound 139 (40 mg; yield: 41%) was obtained from Compound BF (0.10 mL, 1.0 mmol) in a manner similar to that in Example 1.

¹H-NMR (CDCl₃, 270 MHz) δ 8.69 (d, J=4.3 Hz, 1H), 8.49 (d, J=3.0 Hz, 1H), 8.45 (br s, 1H), 7.74–7.13 (m, 9H), 5.30 (dd, J=10.9, 9.9 Hz, 1H), 4.03 (d, J=9.9 Hz, H), 3.78–3.61 (m, 2H), 3.10 (d, J=13.8 Hz, 1H), 3.08 (d, J=11.6 Hz, 1H), 2.79–2.44 (m, 3H), 1.94–1.91 (m, 2H), 1.20 (t, J=7.6 Hz, 3H)

EXAMPLE 121

Synthesis of Compound 140

Compound 140 (43 mg; yield: 57%) was obtained from Compound BG (80 mg, 0.24 mmol) and a borane dimethyl sulfide complex (0.10 mL, 1.0 mmol) in a manner similar to that in Example 1.

¹H-NMR (CDCl₃, 300 MHz) δ 8.54 (s, 1H), 8.45 (d, J=4.0 Hz, 1H), 7.51 (d, J=7.2 Hz, 1H), 7.31–7.14 (m, 8H), 6.88 (d, J=7.6 Hz, 2H), 4.69 (dd, J=10.2, 9.2 Hz, 1H), 3.78 (d, J=13.9 Hz, 1H), 3.60 (d, J=9.2 Hz, 1H), 2.98–2.85 (m, 3H), 2.37 (m, 1H), 2.06 (m, 1H), 1.54–1.40 (m, 2H), 1.30 (d, J=6.9 Hz, 3H)

EXAMPLE 122

Synthesis of Compound 141

Compound 141 (160 mg; yield: 51%) was obtained from Compound BH (330 mg, 0.81 mmol) and a borane dimethyl sulfide complex (0.30 mL, 3.0 mmol) in a manner similar to that in Example 1.

¹H-NMR (DMSO-d₆, 270 MHz) δ 12.72 (br s, 1H), 7.77 (br s, 1H), 7.66 (d, J=7.8 Hz, 1H), 7.52 (d, J=6.9 Hz, 1H), 7.44–7.42 (m, 2H), 7.31 (dd, J=7.9, 3.0 Hz, 1H), 7.20–7.11 (m, 3H), 6.56 (br s, 1H), 5.26 (dd, J=10.7, 9.9 Hz, 1H), 4.00 (d, J=9.9 Hz, 1H), 3.62–3.57 (m, 2H), 3.18 (d, J=13.8 Hz, 1H), 2.86 (m, 1H), 2.70–2.45 (m, 3H), 1.80 (br s, 2H), 1.05 (t, J=7.8 Hz, 3H)

EXAMPLE 123

Synthesis of Compound 142

Compound 142 (24 mg; yield: 25%) was obtained from Compound BI (100 mg, 0.24 mmol) and a borane dimethyl sulfide complex (0.10 ml, 1.0 mmol) in a manner similar to that in Example 1.

¹H-NMR (CDCl₃, 300 MHz) δ 8.69 (d, J=4.3 Hz, 1H), 8.49 (d, J=3.0 Hz, 1H), 8.45 (br s, 1H), 7.74–7.13 (m, 9H), 5.30 (dd, J=10.9, 9.9 Hz, 1H), 4.03 (s, 3H), 3.78–3.61 (m, 2H), 3.10 (d, J=13.8 Hz, 1H), 3.08 (d, J=11.6 Hz, 1H), 2.79–2.44 (m, 3H), 1.94–1.91 (m, 2H), 1.20 (t, J=7.6 Hz, 3H)

EXAMPLE 124

Synthesis of Compound 143

Compound 143 (6.7 mg; yield: 35%) was obtained from Compound BJ (20 mg, 0.047 mmol) and a borane dimethyl sulfide complex (0.05 mL, 0.5 mmol) in a manner similar to that in Example 1.

¹H-NMR (CDCl₃, 300 MHz) δ 8.57 (br s, 1H), 8.50 (d, J=4.1 Hz, 1H), 8.44 (br s, 1H), 7.70–7.45 (m, 2H), 7.36–7.17 (m, 4H), 5.37 (dd, J=10.7, 9.8 Hz, 1H), 4.65 (d, J=9.8 Hz, 1H), 3.82–3.45 (m, 2H), 3.25 (d, J=13.8 Hz, 1H), 3.13 (d, J=11.7 Hz, 1H), 2.79–2.54 (m, 2H), 1.94–1.91 (m, 2H), 1.21 (t, J=7.6 Hz, 3H)

EXAMPLE 125

Synthesis of Compound 144

Compound 144 (32 mg; yield: 9.6%) was obtained from Compound BK (350 mg, 0.84 mmol) and a borane dimethyl sulfide complex (0.30 mL, 3.0 mmol) in a manner similar to that in Example 1.

¹H-NMR (CDCl₃, 300 MHz) δ 8.47 (dd, J=4.8, 1.5 Hz, 1H) 8.40 (br s, 1H), 7.58 (d, J=7.4 Hz, 1H), 7.38 (d, J=7.4 Hz, 1H), 7.24–7.11 (m, 4H), 7.03 (s, 1H), 6.76 (s, 1H), 5.48 (dd, J=10.9, 9.9 Hz, 1H), 4.28 (d, J=9.9 Hz, 1H), 3.91–3.64 (m, 4H), 3.53 (d, J=13.8 Hz, 1H), 3.32 (d, J=13.8 Hz, 1H), 3.08 (m, 1H), 2.78–2.55 (m, 3H), 1.93–1.85 (m, 2H), 1.18 (t, J=7.6 Hz, 3H)

EXAMPLE 126

Synthesis of Compound 145

Compound 145 (160 mg; yield: 46%) was obtained from Compound BL (380 mg, 0.82 mmol) and a borane dimethyl sulfide complex (0.40 mL, 4.0 mmol) in a manner similar to that in Example 1.

¹H-NMR (CDCl₃, 300 MHz) δ 8.52 (dd, J=4.8, 1.5 Hz, 1H) 8.47 (d, J=2.0 Hz, 1H), 8.09 (d, J=1.8 Hz, 1H), 7.57 (dt, J=7.6, 1.7 Hz, 1H), 7.48 (d, J=1.8 Hz, 1H), 7.31–7.13 (m, 5H), 4.92 (dd, J=11.2, 9.7 Hz, 1H), 3.94 (d, J=9.7 Hz, 1H), 3.79 (d, J=13.7 Hz, 1H), 3.67 (m, 1H), 3.17 (d, J=13.7 Hz, 1H), 3.07 (dt, J=11.9, 3.2 Hz, 1H), 2.79–2.58 (m, 2H), 2.40 (m, 1H), 1.94–1.89 (m, 2H), 1.19 (t, J=7.6 Hz, 3H)

EXAMPLE 127

Synthesis of Compound 146

Compound 146 (167 mg; yield: 45%) was obtained from Compound BM (360 mg, 0.74 mmol) and a borane dimethyl sulfide complex (0.3 mL, 3.0 mmol) in a manner similar to that in Example 1.

¹H-NMR (CDCl₃, 300 MHz) δ 8.52 (dd, J=4.8, 1.7 Hz, 1H) 8.47 (d, J=2.2 Hz, 1H), 8.09 (d, J=1.7 Hz, 1H), 7.57–7.51 (m, 2H), 7.49 (d, J=2.0 Hz, 1H), 7.34–7.26 (m, 3H), 7.15 (m, 1H), 4.91 (dd, J=11.1, 9.9 Hz, 1H), 4.09–3.96 (m, 2H), 3.78 (d, J=13.8 Hz, 1H), 3.17 (d, J=13.8 Hz, 1H), 3.08 (dt, J=11.7, 3.1 Hz, 1H), 2.43 (m, 1H), 2.06 (m, 1H), 1.65 (m, 1H)

EXAMPLE 128

Synthesis of Compound 147

Compound 147 (172 mg; yield: 44%) was obtained from Compound BN (400 mg, 0.82 mmol) and a borane dimethyl sulfide complex (0.40 mL, 4.0 mmol) in a manner similar to that in Example 1.

¹H-NMR (CDCl₃, 300 MHz) δ 8.55 (d, J=1.8 Hz, 1H), 8.50 (dd, J=4.8, 1.8 Hz, 1H), 7.67 (d, J=7.6 Hz, 1H), 7.52 (dd, J=8.0, 1.1 Hz, 1H), 7.31–7.23 (m, 3H), 7.08 (m, 1H), 6.80 (d, J=3.5 Hz, 1H), 6.55 (m, 1H), 4.98 (dd, J=11.2, 9.6 Hz, 1H), 4.14–4.00 (m, 3H), 3.07 (d, J=13.7 Hz, 1H), 2.98 (dt, J=11.9, 3.0 Hz, 1H), 2.52–2.39 (m, 4H), 1.99 (m, 1H), 1.65 (m, 1H)

EXAMPLE 129

Synthesis of Compound 148

Compound 148 (37 mg; yield: 79%) was obtained from Compound 146 (50 mg, 0.1 mmol) and palladium on carbon (10 mg) in a manner similar to that in Example 40.

¹H-NMR (CD₃OD, 300 MHz) δ 8.44 (d, J=2.0 Hz, 1H), 8.39 (dd, J=4.9, 1.5 Hz, 1H), 7.79 (dt, J=7.8, 1.7 Hz, 1H), 7.55–7.50 (m, 2H), 7.40–7.25 (m, 2H), 7.11 (m, 1H), 6.44 (d, J=1.5 Hz, 1H), 6.40 (d, J=1.5 Hz, 1H), 5.12 (dd, J=11.4, 9.6 Hz, 1H), 4.03–3.88 (m, 2H), 3.75 (d, J=9.4 Hz, 1H), 3.14 (d, J=14.0 Hz, 1H), 2.94 (m, 1H), 2.41 (m, 1H), 1.95 (m, 1H), 1.71 (m, 1H)

EXAMPLE 130

Synthesis of Compound 149 and Compound 150

Compound 149 (6 mg; yield: 23%) and Compound 150 (8 mg; yield: 31%) were obtained from Compound 148 (25 mg, 0.05 mmol) and potassium cyanate (4.1 mg, 0.05 mmol) in a manner similar to that in Example 73.
Compound 149:
$^1$H-NMR (CDCl$_3$, 270 MHz) δ 8.75 (br s, 1H), 8.51 (s, 1H) 8.48 (dd, J=4.7, 1.2 Hz, 1H), 7.56–7.51 (m, 2H), 7.34–7.22 (m, 3H), 7.10 (m, 1H), 6.82 (s, 1H), 6.81 (s, 1H), 4.95 (dd, J=10.9, 9.9 Hz, 1H), 4.01 (m, 1H), 3.91–3.85 (m, 2H), 3.04 (d, J=13.5 Hz, 1H), 2.92 (m, 1H), 2.38 (m, 1H), 2.16 (s, 3H), 1.99 (m, 1H), 1.65 (m, 1H)
Compound 150:
$^1$H-NMR (CDCl$_3$, 270 MHz) δ 8.66 (br s, 1H), 8.51 (s, 1H) 8.43 (d, J=4.7 Hz, 1H), 7.53–7.48 (m, 2H), 7.34–7.19 (m, 3H), 7.04 (m, 1H), 6.75 (s, 2H), 5.26 (br s, 2H), 4.97 (dd, J=10.7, 9.9 Hz, 1H), 3.98 (m, 1H), 3.88–3.78 (m, 2H), 3.07 (d, J=14.0 Hz, 1H), 2.97 (d, J=11.5 Hz, 1H), 2.37 (m, 1H), 1.95 (m, 1H), 1.63 (m, 1H)

EXAMPLE 131

Synthesis of Compound 151

Compound 151 (33 mg; yield: 16%) was obtained from Compound BO (216 mg, 0.5 mmol) and a borane dimethyl sulfide complex (0.40 mL, 4.0 mmol) in a manner similar to that in Example 1.
$^1$H-NMR (CDCl$_3$, 300 MHz) δ 8.49 (br s, 2H), 7.72–7.47 (m, 3H), 7.42–7.14 (m, 8H), 5.04 (dd, J=10.6, 9.6 Hz, 1H), 4.16 (m, 1H), 3.86 (d, J=9.6 Hz, 1H), 3.77 (d, J=13.9 Hz, 1H), 3.06–3.01 (m, 2H), 2.47–2.39 (m, 4H), 1.95 (m, 1H), 1.71 (m, 1H)

Compounds 152 to 156 and Compounds 159 to 183 were synthesized in a manner similar to that in Example 1.

EXAMPLE 132

Synthesis of Compound 157 and Compound 158

Compound 157 (15.9 mg; >99% e.e.; yield: 21%) which is the (+)-form of Compound 156 and Compound 158 (31.1 mg; >99% e.e.; yield: 41%) which is the (−)-form of Compound 156 were obtained from Compound 156 in a manner similar to that in Example 90.
Compound 157: $[α]^{26}_D$=+26.0° (c=0.15, methanol)
Compound 158: $[α]^{26}_D$=−28.4° (c=0.15, methanol)

EXAMPLE 133

Synthesis of Compound 184

Compound 185 (170 mg; yield: 68%) was obtained from Compound BP (260 mg, 0.60 mmol) and a borane dimethyl sulfide complex (0.27 mL, 3.0 mmol) in a manner similar to that in Example 1.
$^1$H-NMR (CDCl$_3$, 270 MHz) δ 8.50–8.48 (m, 2H), 7.56 (d, J=7.8 Hz, 1H), 7.37 (m, 1H), 7.30–7.17 (m, 7H), 5.02 (dd, J=11.4, 9.5 Hz, 1H), 4.14 (m, 1H), 4.03 (d, J=9.5 Hz, 1H), 3.80 (d, J=13.8 Hz, 1H), 3.08 (d, J=13.8 Hz, 1H), 2.99 (m, 1H), 2.44–2.41 (m, 4H), 1.97 (m, 1H), 1.73 (m, 1H)

EXAMPLE 134

Synthesis of Compound 185

Compound 185 (150 mg; yield; 50%) was obtained from Compound BQ (310 mg, 0.71 mmol) and a borane dimethyl sulfide complex (0.27 ml, 3.0 mmol) in a manner similar to that in Example 1.
$^1$H-NMR (CDCl$_3$, 270 MHz) δ 8.71 (d, J=4.8 Hz, 1H), 8.46 (d, J=3.3 Hz, 1H), 8.44 (br s, 1H), 7.71 (m, 1H), 7.59 (d, J=7.7 Hz, 1H), 7.43 (d, J=7.7 Hz, 1H), 7.34 (m, 1H), 7.29–7.17 (m, 5H), 5.37 (dd, J=10.8, 9.4 Hz, 1H), 4.10 (m, 1H), 4.06 (d, J=9.4 Hz, 1H), 3.62 (d, J=13.8 Hz, 1H), 3.20 (d, J=13.8 Hz, 1H), 3.04 (m, 1H), 2.52 (m, 1H), 2.44 (s, 3H), 2.04 (m, 1H), 1.80 (m, 1H)

EXAMPLE 135

Synthesis of Compound 186

Compound 186 (19 mg; yield; 40%) was obtained from Compound BR (50 mg, 0.11 mmol) and sodium borohydride (45 mg, 1.2 mmol) in a manner similar to that in Example 5.
$^1$H-NMR (CDCl$_3$, 270 MHz) δ 8.50–8.48 (m, 2H), 7.56 (d, J=7.9 Hz, 1H), 7.40–7.15 (m, 8H), 6.66 (d, J=15.7 Hz, 1H), 5.84 (dq, J=15.7, 6.5 Hz, 1H), 4.97 (dd, J=10.9, 9.6 Hz, 1H), 4.00 (d, J=9.6 Hz, 1H), 3.87–3.77 (m, 2H), 3.08 (d, J=13.7 Hz, 1H), 3.02 (m, 1H), 2.37 (m, 1H), 1.92 (dd, J=6.5, 1.3 Hz, 3H), 1.91 (m, 1H), 1.35 (m, 1H)

EXAMPLE 136

Synthesis of Compound 187

Compound 187 (8.0 mg; yield; 42%) was obtained from Compound BS (20 mg, 0.047 mmol) and sodium borohydride (15 mg, 0.4 mmol) in a manner similar to that in Example 5.
$^1$H-NMR (CDCl$_3$, 270 MHz) δ 8.69 (d, J=4.0 Hz, 1H), 8.49 (dd, J=4.8, 1.6 Hz, 1H), 8.44 (d, J=2.1 Hz, 1H), 7.71 (m, 1H), 7.59 (d, J=7.7 Hz, 1H), 7.45 (d, J=7.7 Hz, 1H), 7.31–7.14 (m, 1H), 6.69 (d, J=15.2 Hz, 1H), 5.98 (dq, J=15.2, 6.6 Hz, 1H), 5.28 (dd, J=11.3, 9.5 Hz, 1H), 4.03 (d, J=9.5 Hz, 1H), 3.63 (d, J=13.6 Hz, 1H), 3.20 (d, J=13.6 Hz, 1H), 3.08 (m, 1H), 2.68–2.60 (m, 2H), 2.48 (m, 1H), 2.37 (m, 1H), 1.92 (dd, J=6.6, 1.8 Hz, 3H)

EXAMPLE 137

Synthesis of Compound 188

Compound 188 (179 mg; yield: 62%) was obtained from Compound BT (300 mg, 0.74 mmol) and a borane dimethyl sulfide complex (0.90 mL, 10 mmol) in a manner similar to that in Example 1.
$^1$H-NMR (CDCl$_3$, 270 MHz) δ 8.51 (d, J=1.3 Hz, 1H), 8.49 (d, J=1.3 Hz, 1H), 7.62 (d, J=7.8 Hz, 1H), 7.46 (d, J=1.0 Hz, 1H), 7.33 (d, J=6.6 Hz, 1H), 7.28–7.13 (m, 4H), 6.40 (dd, J=3.2, 0.8 Hz, 1H), 6.33 (dd, J=3.3, 1.8 Hz, 1H), 5.24 (dd, J=11.3, 9.6 Hz, 1H), 3.99 (d, J=9.6 Hz, 1H), 3.73 (d, J=3.6 Hz, 1H), 3.66 (m, 1H), 3.19 (d, J=13.8 Hz, 1H), 3.00 (m, 1H), 2.77–2.55 (m, 2H), 2.42 (m, 1H), 1.91–1.88 (m, 2H), 1.19 (t, J=7.6 Hz, 3H)

EXAMPLE 138

Synthesis of Compound 189

Compound 189 (170 mg; yield: 85%) was obtained from Compound BU (200 mg, 0.44 mmol) and a borane dimethyl sulfide complex (0.360 mL, 4.0 mmol) in a manner similar to that in Example 1.
$^1$H-NMR (CDCl$_3$, 270 MHz) δ 8.49–8.48 (m, 2H), 7.56 (d, J=7.9 Hz, 1H), 7.46–7.21 (m, 8H), 7.13 (dd, J=8.1, 8.0

Hz, 1H), 6.88 (d, J=7.4 Hz, 1H), 5.98 (dd, J=11.2, 9.5 Hz, 1H), 4.46 (m, 1H), 3.82 (d, J=9.5 Hz, 1H), 3.75 (d, J=13.9 Hz, 1H), 3.08 (m, 1H), 3.02 (d, J=13.9 Hz, 1H), 2.66 (m, 1H), 2.40 (m, 1H), 1.79 (m, 1H)

EXAMPLE 139

Synthesis of Compound 190

Compound 190 (183 mg; yield: 89%) was obtained from Compound BV (262 mg, 0.12 mmol) and a borane dimethyl sulfide complex (0.090 mL, 1.0 mmol) in a manner similar to that in Example 1.

$^1$H-NMR (CDCl$_3$, 270 MHz) δ 8.52–8.49 (m, 2H), 7.66 (d, J=7.9 Hz, 1H), 7.40–7.15 (m, 7H), 7.13 (dd, J=8.1, 8.0 Hz, 1H), 6.88 (d, J=7.4 Hz, 1H), 5.98 (dd, J=11.2, 9.6 Hz, 1H), 4.46 (m, 1H), 4.22 (d, J=9.6 Hz, 1H), 3.91 (d, J=13–5 Hz, 1H), 3.08–2.99 (m, 2H), 2.58 (m, 1H), 2.42 (m, 1H), 2.26–2.18 (m, 4H), 1.78 (m, 1H)

EXAMPLE 140

Synthesis of Compound 191 and Compound 192

Compound 185 (26 mg; yield: 28%), Compound 191 (26 mg; yield: 26%) and Compound 192 (11 mg; yield: 12%) were obtained from a mixture of Compound BW, Compound BX, and Compound BY (BW:BX:BY=1:1:1; 100 mg, 0.22 mmol) and a borane dimethyl sulfide complex (0.090 mL, 1.0 mmol) in a manner similar to that in Example 1.
Compound 191:

$^1$H-NMR (CDCl$_3$, 270 MHz) δ 8.49–8.47 (m, 2H), 8.05 (d, J=7.9 Hz, 1H), 7.63–7.51 (m, 3H), 7.47–7.41 (m, 2H), 7.32–7.21 (m, 3H), 5.17 (dd, J=11.5, 9.3 Hz, 1H), 4.43 (m, 1H), 4.03 (d, J=9.3 Hz, 1H), 3.81 (d, J=13.8 Hz, 1H), 3.18 (s, 3H), 3.10 (m, 1H), 3.10 (d, J=13.8 Hz, 1H), 2.45 (m, 1H), 2.25 (m, 1H), 1.75 (m, 1H)
Compound 192:

$^1$H-NMR (CDCl$_3$, 270 MHz) δ 8.50–8.49 (m, 2H), 8.02 (m, 1H), 7.56–7.49 (m, 3H), 7.47–7.42 (m, 2H), 7.29–7.22 (m, 3H), 5.03 (dd, J=11.2, 9.4 Hz, 1H), 3.97 (d, J=9.4 Hz, 1H), 3.81–3.74 (m, 2H), 3.11–3.01 (m, 2H), 2.74 (s, 3H), 2.38 (m, 1H), 2.07 (m, 1H), 1.85 (m, 1H)

EXAMPLE 141

Synthesis of Compound 193

Compound 193 (1.13 g; yield: 35%) was obtained from Compound 98 (2.7 g, 5.9 mmol) and hydrochloric acid (a 4 mol/l solution in ethyl acetate, 3.0 mL) in a manner similar to that in Example 3.

$^1$H-NMR (DMSO-d$_6$, 270 MHz) δ 8.76 (d, J=5.3 Hz, 1H), 8.71 (br S, 1H), 8.35 (d, J=8.7 Hz, 1H), 7.93 (m, 1H), 7.75 (d, J=6.9 Hz, 1H), 7.64–7.53 (m, 4H), 7.42 (dd, J=7.6, 6.6 Hz, 1H), 7.20 (dd, J=8.7, 6.6 Hz, 1H), 5.59 (m, 1H), 4.40–4.10 (m, 2H), 3.89 (m, 1H), 3.65 (m, 1H), 3.10 (br s, 1H), 2.85 (m, 1H), 1.91–1.85 (m, 2H)

Elemental Analysis: C$_{21}$H$_{22}$BrCl$_2$N$_3$O$_2$S.0.4H$_2$0.2C$_2$H$_5$OH

Calcd. (%): C, 46.93; H, 4.42; N, 7.67

Found (%): C, 46.96; H, 4.48; N, 7.75

EXAMPLE 142

Synthesis of Compound 194

Compound 194 (0.60 g; yield: 65%) was obtained from Compound 101 (0.84 g, 1.5 mmol) and hydrochloric acid (a 4 mol/l solution in ethyl acetate, 2.0 mL) in a manner similar to that in Example 3.

$^1$H-NMR (D$_2$O, 270 MHz) δ 8.50–8.44 (m, 3H), 8.23 (d, J=7.9 Hz, 1H), 7.91 (m, 1H), 7.78 (m, 1H), 7.67 (d, J=8.6 Hz, 1H), 7.46 (m, 1H), 7.35 (m, 2H), 7.19 (m, 1H), 6.94 (m, 1H), 5.29 (dd, J=10.6, 9.8 Hz, 1H), 4.23 (d, J=9.8 Hz, 1H), 3.96 (m, 1H), 3.58–3.43 (m, 2H), 2.87 (m, 1H), 2.52 (m, 1H), 1.91–1.81 (m, 2H)

Elemental Analysis: C$_{21}$H$_{22}$Cl$_2$N$_3$O$_2$.3.2H$_2$O.0.5C$_2$H$_5$OH

Calcd. (%): C, 48.42; H, 5.55; N, 9.82

Found (%): C, 48.40; H, 5.47; N, 9.79

EXAMPLE 143

Synthesis of Compound 195

Compound 195 (0.94 g; yield: 80%) was obtained from Compound 29 (1.1 g, 2.4 mmol) and hydrochloric acid (a 4 mol/l solution in ethyl acetate, 4.0 mL) in a manner similar to that in Example 3.

$^1$H-NMR (DMSO-d$_6$, 270 MHz) δ 8.78 (d, J=5.6 Hz, 1H), 8.75 (br S, 1H), 8.39 (m, 1H), 7.96 (m, 1H), 7.78 (d, J=7.5 Hz, 1H), 7.59 (dd, J=7.9, 1.1 Hz, 2H), 7.44–7.36 (m, 5H), 7.20 (dd, J=7.5, 6.9 Hz, 1H), 5.5 (m, 1H), 4.22–3.85 (m, 3H), 3.73 (m, 2H), 3.09 (m, 1H), 2.76 (m, 1H), 2.00 (m, 1H)

Elemental Analysis: C$_{23}$H$_{24}$BrCl$_2$N$_3$O$_2$.0.8H$_2$O.0.1C$_2$H$_5$OH Calcd. (%): C, 51.20; H, 4.85; N, 7.72

Found (%): C, 51.15; H, 4.76; N, 7.67

EXAMPLE 144

Synthesis of Compound 196

Compound 196 (0.28 g; yield: 56%) was obtained from Compound 156 (0.40 g, 1.0 mmol) and hydrochloric acid (a 4 mol/l solution in ethyl acetate, 1.0 mL) in a manner similar to that in Example 3.

$^1$H-NMR (DMSO-d$_6$, 270 MHz) δ 8.74 (d, J=4.6 Hz, 1H), 8.70 (br s, 1H), 8.33 (m, 1H), 7.90 (m, 1H), 7.58 (d, J=7.3 Hz, 2H), 7.41–7.32 (m, 4H), 7.21–7.14 (m, 3H), 5.41 (m, 1H), 4.20–3.80 (m, 4H), 2.98 (m, 1H), 2.72–2.48 (m, 2H), 2.05–1.80 (m, 3H), 1.13 (t, J=7.6 Hz, 3H)

Elemental Analysis: C$_{25}$H$_{28}$ClN$_3$O$_2$.2.9H$_2$O

Calcd. (%): C, 61.25; H, 6.95; N, 8.57

Found (%): C, 61.26; H, 6.79; N, 8.49

EXAMPLE 145

Synthesis of Compound 197

Compound 197 (0.54 g; yield: 35%) was obtained from Compound 155 (1.21 g, 31 mmol) and hydrochloric acid (a 4 mol/l solution in ethyl acetate, 2.0 mL) in a manner similar to that in Example 3.

$^1$H-NMR (DMSO-d$_6$, 270 MHz) δ 8.79–8.74 (m, 2H), 8.38 (m, 1H), 8.33 (m, 1H), 7.93 (m, 1H), 7.80–7.45 (m, 2H), 7.40–7.28 (m, 3H), 7.20–7.07 (m, 3H), 5.47 (m, 1H), 4.10 (m, 1H), 3.85–3.50 (m, 3H), 3.15 (m, 1H), 2.75 (m, 1H), 2.28 (s, 3H), 2.05–1.90 (m, 2H)

Elemental Analysis: C$_{24}$H$_{26}$ClN$_3$O$_2$.2.7H$_2$O.0.1C$_2$H$_5$OH

Calcd. (%): C, 60.91; H, 6.75; N, 8.81

Found (%): C, 60.90; H, 6.90; N, 8.85

EXAMPLE 146

Synthesis of Compound 198

Compound 198 (0.23 g; yield: 28%) was obtained from Compound 59 (0.79 g, 1.4 mmol) and hydrochloric acid (a 4 mol/l solution in ethyl acetate, 1.4 mL) in a manner similar to that in Example 3.

$^1$H-NMR (DMSO-d$_6$, 270 MHz) δ 9.20 (m, 1H), 8.77–8.75 (m, 2H) 8.43 (m, 1H), 8.00 (m, 1H), 7.91 (m, 1H), 7.74 (d, J=7.9 Hz, 1H), 7.58 (d, J=8.6 Hz, 1H), 7.39 (dd, J=7.9, 6.9 Hz, 1H), 7.21–6.85 (m, 2H), 6.84 (d, J=7.9 Hz, 1H), 5.40 (m, 1H), 3.93–3.52 (m, 3H), 3.14–2.90 (m, 3H), 2.81 (m, 1H), 1.97–1.85 (m, 2H), 1.12 (d, J=7.1 Hz, 3H), 1.09 (d, J=7.1 Hz, 3H)

Elemental Analysis: C$_{27}$H$_{30}$BrClN$_4$O$_4$·3.4H$_2$O·0.1C$_2$H$_5$OH

Calcd. (%): C, 49.81; H, 5.75; N, 8.54

Found (%): C, 49.85; H, 5.69; N, 8.50

EXAMPLE 147

Synthesis of Compound 199

Compound 199 (0.54 g; yield; 43%) was obtained from Compound 139 (1.0 g, 2.5 mmol) and hydrochloric acid (a 4 mol/l solution in ethyl acetate, 2.0 mL) in a manner similar to that in Example 3.

$^1$H-NMR (DMSO-d$_6$, 270 MHz) δ 8.77 (d, J=4.6 Hz, 1H), 8.73 (m, 1H), 8.54 (m, 1H), 8.35 (m, 1H), 7.97–7.89 (m, 3H), 7.55 (m, 1H), 7.43 (m, 1H), 7.21–7.15 (m, 3H), 5.55 (m, 1H), 4.31–3.80 (m, 4H), 3.03 (m, 1H), 2.66 (m, 1H), 2.62–2.48 (m, 2H), 2.02 (m, 1H), 1.90 (m, 1H), 1.13 (t, J=7.5 Hz, 3H)

EXAMPLE 148

Synthesis of Compound 200

Compound 200 (0.65 g; yield: 42%) was obtained from Compound 184 (1.3 g, 3.0 mmol) and hydrochloric acid (a 4 mol/l solution in ethyl acetate, 2.0 mL) in a manner similar to that in Example 3.

$^1$H-NMR (DMSO-d6, 270 MHz) δ 8.89 (br s, 1H), 8.83 (br s, 1H), 8.63 (m, 1H), 8.45 (m, 1H), 8.03–7.85 (m, 3H), 7.64 (d, J=6.9 Hz, 1H), 7.42 (m, 1H), 7.36–7.25 (m, 3H), 5.75 (m, 1H), 4.42 (m, 1H), 4.05 (m, 1H), 3.79–3.60 (m, 2H), 3.10 (m, 1H), 2.80 (m, 1H), 2.49 (s, 3H), 1.98–1.88 (m, 2H)

Elemental Analysis: C$_{23}$H$_{25}$ClN$_4$O$_2$S·2.8H$_2$O·0.2C$_2$H$_5$OH

Calcd. (%): C, 54.40; H, 6.20; N, 10.84

Found (%): C, 54.40; H, 6.39; N, 11.02

EXAMPLE 149

Synthesis of Compound 201

Compound 201 (1.2 g; yield: 63%) was obtained from Compound 54 (2.0 g, 3.7 mmol) and hydrochloric acid (a 4 mol/l solution in ethyl acetate, 2.0 ml) in a manner similar to that in Example 3.

$^1$H-NMR (DMSO-d$_6$, 270 MHz) δ 8.78 (br s, 2H), 8.76 (br s, 1H), 8.44–8.40 (m, 2H), 7.95 (m, 1H), 7.83 (m, 1H), 7.74 (d, J=8.6 Hz, 1H), 7.58 (dd, J=7.9, 1.0 Hz, 1H), 7.39 (dd, J=8.2, 6.9 Hz, 1H), 7.20 (br s, 1H), 7.19 (dd, J=7.9, 7.3 Hz, 1H), 6.79 (d, J=7.9 Hz, 1H), 5.50 (m, 1H), 4.20–3.80 (m, 4H), 3.66 (s, 3H), 3.09 (m, 1H), 2.80 (m, 1H), 2.10 (m, 1H), 1.94 (m, 1H)

Elemental Analysis: C$_{25}$H$_{26}$ClN$_4$O$_5$·2.5H$_2$O·0.1C$_2$H$_5$OH

Calcd. (%): C, 48.23; H, 5.08; N, 8.93

Found (%): C, 48.22; H, 5.05; N, 8.85

EXAMPLE 150

Synthesis of Compound 202

Compound 202 (2.0 g; yield: 52%) was obtained from Compound 50 (3.2 g, 5.6 mmol) and hydrochloric acid (a 4 mol/l solution in ethyl acetate, 3.5 ml) in a manner similar to that in Example 3.

$^1$H-NMR (DMSO-d$_6$, 270 MHz) δ 10.31 (br s, 1H), 8.80–8.76 (m, 3H) 8.42 (d, J=8.1 Hz, 1H), 7.94 (dd, J=7.9, 5.8 Hz, 1H), 7.74 (d, J=7.6 Hz, 1H), 7.61–7.50 (m, 2H), 7.41 (dd, J=7.4, 7.3 Hz, 1H), 7.19 (m, 1H), 6.88 (d, J=8.2 Hz, 1H), 5.60 (br s, 1H), 5.10 (m, 1H), 4.24 (m, 1H), 4.00–3.50 (m, 5H), 3.15 (m, 1H), 3.02–2.94 (m, 2H), 1.18 (t, J=7.2 Hz, 3H)

Elemental Analysis: C$_{25}$H$_{29}$BrCl$_2$N$_4$O$_5$S·0.8H$_2$O·0.4C$_2$H$_5$OH Calcd. (%): C, 45.48; H, 4.88; N, 8.22

Found (%): C, 45.40; H, 4.80; N, 8.19

EXAMPLE 151

Synthesis of Compound 203

Compound 203 (0.42 g; yield; 38%) was obtained from Compound 85 (0.88 g, 1.60 mmol) and hydrochloric acid (a 4 mol/l solution in ethyl acetate, 1.252 mL) in a manner similar to that in Example 3.

$^1$H-NMR (DMSO-d$_6$, 270 MHz) δ 8.81–8.75 (m, 3H), 8.38 (m, 1H), 7.90 (m, 1H), 7.59–7.40 (m, 2H), 7.18–7.13 (m, 4H), 6.88 (m, 1H), 5.37 (br s, 1H), 4.24–3.70 (m, 4H), 3.10–2.80 (m, 4H), 2.75–2.52 (m, 3H), 2.10 (m, 1H), 1.87 (m, 1H), 1.12 (t, J=7.6 Hz, 3H)

Elemental Analysis: C$_{26}$H$_{32}$Cl$_2$N$_4$O$_5$S·0.4H$_2$O·0.5C$_2$H$_5$OH

Calcd. (%): C, 52.83; H, 5.88; N, 9.13

Found (%): C, 52.82; H, 5.87; N, 9.13

EXAMPLE 152

Synthesis of Compound 204

Compound 204 (1.1 g; yield; 52%) was obtained from Compound 110 (1.6 g, 3.1 mmol) and hydrochloric acid (a 4 mol/l solution in ethyl acetate, 3.0 mL) in a manner similar to that in Example 3.

$^1$H-NMR (DMSO-d$_6$, 270 MHz) δ 10.11 (br s, 1H), 8.82 (d, J=5.4 Hz, 1H), 8.82–8.74 (m, 3H), 8.42 (m, 1H), 8.28 (d, J=8.2 Hz, 1H), 8.00 (m, 1H), 7.90–7.72 (m, 2H), 7.42 (m, 1H), 7.29 (m, 1H), 7.20–7.12 (m, 3H), 6.70 (d, J=7.7 Hz, 1H), 6.48 (br s, 1H), 5.60 (br s, 1H), 4.89–4.71 (m, 3H), 4.55–4.20 (m, 3H), 3.40–3.05 (m, 2H), 2.65–2.30 (m, 3H), 1.95 (m, 1H), 1.07 (t, J=7.5 Hz, 3H)

Elemental Analysis: C$_{31}$H$_{36}$Cl$_3$N$_5$O$_3$·2.2H$_2$O·0.2C$_2$H$_5$OH

Calcd. (%): C, 55.31; H, 6.14; N, 10.27

Found (%): C, 55.33; H, 6.11; N, 10.23

EXAMPLE 153

Synthesis of Compound 205 and Compound 206 (Optical Resolution of Compound 101)

Compound 101 (200 mg) was optically resolved by high performance liquid chromatography (Chiralcel OD column (diameter: 2 cm; length: 25 cm); eluent: isopropyl alcohol/n-hexane/diethylamine=20/80/0.1; flow rate: 5 mL/min.; detection: UV 254 nm) to obtain Compound 205 (41 mg; >99% e.e.; yield: 21%), which is the (−)-form of Compound 101, and Compound 206 (12.4 mg; >99% e.e.; yield: 25%), which is the (+)-form of Compound 101.

Compound 205 ((−)-Compound 101)

$[\alpha]^{26}_D$=−40.3° (c=0.15, methanol)

Compound 206 ((+)-Compound 101)

$[\alpha]^{26}_D$=+48.2° (c=0.30, methanol)

Elemental Analysis: $C_{22}H_{21}BrN_4O_2$

Calcd. (%): C, 58.29; H, 4.67; N, 12.36

Found (%): C, 58.33; H, 4.63; N, 12.02

EXAMPLE 154

Synthesis of Compound 207

Compound 207 (1.0 g; yield: 81%) was obtained from Compound 206 (1.0 g, 2.2 mmol) and hydrochloric acid (a 4 mol/solution in ethyl acetate, 2.0 mL) in a manner similar to that in Example 3.

Elemental Analysis: $C_{22}H_{21}BrCl_2N_4O_2 \cdot 1.6H_2O \cdot 0.4C_2H_5OH$

Calcd. (%): C, 47.75; H, 5.03; N, 9.77

Found (%): C, 47.70; H, 4.94; N, 9.75

EXAMPLE 155

Synthesis of Compound 208

Methyl 3-(2-bromophenyl)-4-nitrobutyrate (1.8 g, 6.0 mmol), 2-pyridinecarboxaldehyde (0.61 g, 6.0 mmol), and ammonium acetate (920 mg, 12 mmol) were heated under reflux in ethanol for 20 hours. The solvent was evaporated under reduced pressure, and the residue was purified by silica gel column chromatography (eluted with chloroform/methanol=98/2) to obtain a piperidone derivative. Compound 208 (690 mg; yield: 32%) was obtained from the resulting piperidone derivative and a borane dimethyl sulfide complex (2.7 mL, 30 mmol) in a manner similar to that in Example 1.

$^1$H-NMR (CDCl$_3$, 270 MHz) δ 8.62 (d, J=4.0 Hz, 1H), 7.64 (m, 1H), 7.54 (dd, J=7.5, 1.2 Hz, 1H), 7.40 (d, J=6.6 Hz, 1H), 7.32–7.19 (m, 3H), 7.09 (m, 1H), 5.19 (dd, J=11.3, 9.6 Hz, 1H), 4.37 (d, J=9.6 Hz, 1H), 4.19 (m, 1H), 3.36 (m, 1H), 3.08 (m, 1H), 2.10 (m, 1H), 1.88 (m, 1H), 1.63 (m, 1H)

Elemental Analysis: $C_{16}H_{16}BrN_3O_2$

Calcd. (%): C, 53.05; H, 4.45; N, 11.60

Found (%): C, 53.29; H, 4.42; N, 11.60

EXAMPLE 156

Synthesis of Compound 209

Methyl 3-(2-bromophenyl)-4-nitrobutyrate (1.8 g, 6.0 mmol), benzaldehyde (0.61 mL, 6.0 mmol), and ammonium acetate (920 mg, 12 mmol) were heated under reflux in ethanol for 20 hours. The solvent was evaporated under reduced pressure, and the residue was purified by silica gel column chromatography (eluted with chloroform/methanol=98/2) to obtain a piperidone derivative (1.4 g; yield: 57%). Compound 209 (890 mg; yield: 41%) was obtained from the resulting piperidone derivative and a borane dimethyl sulfide complex (2.7 mL, 30 mmol) in a manner similar to that in Example 1.

$^1$H-NMR (CDCl$_3$, 270 MHz) δ 8.62 (d, J=2.6 Hz, 1H), 7.56 (d, J=8.2 Hz, 1H), 7.37–7.21 (m, 5H), 7.22 (d, J=7.6 Hz, 1H), 7.13–7.08 (m, 2H), 6.27 (d, J=5.6 Hz, 1H), 5.56 (m, 1H), 4.40 (m, 1H), 4.20 (m, 1H), 3.83 (m, 1H), 2.45 (m, 1H), 1.92 (m, 1H)

EXAMPLE 157

Synthesis of Compound 210

Compound BZ (600 mg, 1.2 mmol) was dissolved in tetrahydrofuran (15 mL), and a borane dimethyl sulfide complex (0.019 mL, 12 mmol) was added thereto in an argon atmosphere, followed by heating under reflux for 11 hours. Methanol was added dropwise to the reaction mixture under cooling with ice to decompose an excessive amount of a borane dimethyl sulfide complex, and the solvent was evaporated under reduced pressure. Chloroform was added to the residue, and the mixture was washed with a saturated aqueous sodium hydrogen carbonate solution and dried over sodium sulfate. The solvent was evaporated under reduced pressure, and the residue was purified by silica gel column chromatography (eluted with chloroform) to obtain Compound 210 (171 mg; yield: 30%).

$^1$H-NMR (CDCl$_3$, 300 MHz) δ 7.56–7.52 (m, 1H), 7.41–7.22 (m, 3H), 7.12–6.98 (m, 3H), 5.24 (s, 2H), 5.21 (s, 2H), 4.88–4.81 (m, 1H), 4.14–4.03 (m, 2H), 3.52 (s, 3H), 3.50 (s, 3H), 3.28–3.22 (m, 1H), 3.11–3.02 (m, 1H), 2.10–2.05 (m, 1H), 1.79–1.62 (m, 1H)

EXAMPLE 158

Synthesis of Compound 211

To a solution (5 mL) of Compound 208 (72 mg, 0.20 mmol) in acetic acid were added 2-pyridinecarboxaldehyde (0.061 mg, 0.60 mmol) and sodium triacetoxyborohydride (212 mg, 1.0 mmol), and the mixture was stirred at room temperature for 12 hours. The reaction solution was poured into water, and the mixture was neutralized with a saturated aqueous sodium hydrogen carbonate solution, and extracted with chloroform. The extract was dried over sodium sulfate, and the solvent was evaporated under reduced pressure. The residue was purified by silica gel column chromatography (eluted with chloroform/methanol=9/1) to obtain Compound 211 (19 mg; yield: 21%).

$^1$H-NMR (CDCl$_3$, 270 MHz) δ 8.70 (d, J=3.6 Hz, 1H), 8.51 (d, J=3.8 Hz, 1H), 7.70–7.59 (m, 2H), 7.53 (dd, J=7.7, 1.2 Hz, 1H), 7.42–7.39 (m, 2H), 7.31–7.26 (m, 2H), 7.24–7.05 (m, 3H), 5.44 (dd, J=11.3, 9.8 Hz, 1H), 4.08 (d, J=9.8 Hz, 1H), 4.07 (m, 1H), 3.73 (d, J=14.0 Hz, 1H), 3.45 (d, J=14.0 Hz, 1H), 3.14 (m, 1H), 2.67 (m, 1H), 2.05 (m, 1H), 1.82 (m, 1H)

EXAMPLE 159

Synthesis of Compound 212

To a solution (5 mL) of Compound 209 (722 mg, 2.0 mmol) in acetic acid were added 4-imidazolecarboxaldehyde (192 mg, 2.0 mmol) and sodium triacetoxyborohydride (2.1 g, 1.0 mmol), and the mixture was stirred at room temperature for 12 hours. The reaction solution was poured into water, and the mixture was neutralized with a saturated aqueous sodium hydrogen carbonate solution, and extracted with chloroform. The extract was dried over sodium sulfate, and the solvent was evaporated under reduced pressure. The residue was purified by silica gel column chromatography (eluted with chloroform/methanol=9/1) to obtain Compound 212 (362 mg; yield: 41%).

$^1$H-NMR (CDCl$_3$, 270 MHz) δ 7.71 (br s, 1H), 7.52 (d, J=7.9 Hz, 1H), 7.45–7.26 (m, 7H), 7.07 (m, 1H), 6.82 (br s, 1H), 6.01 (br s, 1H), 4.98 (dd, J=11.2, 9.9 Hz, 1H), 3.97 (m, 1H), 3.78 (d, J=9.3 Hz, 1H), 3.65 (d, J=14.5 Hz, 1H), 3.28 (d, J=14.5 Hz, 1H), 3.17 (m, 1), 2.53 (m, 1H), 2.05 (m, 1H), 1.75 (m, 1H)

EXAMPLE 160

Synthesis of Compound 213

To a solution (5 mL) of Compound 212 (35 mg, 0.079 mmol) in DMF were added methyl iodide (1.0 ml, 7.1 mmol) and potassium carbonate (50 mg, 0.36 mmol), and the mixture was stirred at room temperature for 12 hours. The reaction solution was poured into water and the mixture was extracted with chloroform. The extract was dried over sodium sulfate, and the solvent was evaporated under reduced pressure. The residue was purified by preparative thin layer chromatography (developed with chloroform/methanol=9/1) to obtain Compound 213 (19 mg; yield: 40%).

$^1$H-NMR (CDCl$_3$, 270 MHz) δ 9.89 (br s, 1H), 7.53 (d, J=7.9 Hz, 1H), 7.45–7.19 (m, 7H), 7.10 (dd, J=8.6, 6.9 Hz, 1H), 7.00 (br s, 1H), 5.10 (dd, J=9.6, 9.2 Hz, 1H), 4.06 (m, 1H), 3.96 (s, 3H), 3.88 (s, 3H), 3.81 (d, J=9.6 Hz, 1H), 3.58 (d, J=14.8 Hz, 1H), 3.25 (d, J=14.8 Hz, 1H), 3.17 (m, 1H), 2.50 (m, 1H), 2.10 (m, 1H), 1.75 (m, 1H)

EXAMPLE 161

Synthesis of Compound 214

Compound 214 (63 mg; yield: 78%) was obtained from Compound 208 (60 mg, 0.11 mmol), 4-cyanobenzaldehyde (26 mg, 0.2 mmol), and sodium triacetoxyborohydride (52 mg, 0.25 mmol) in a manner similar to that in Example 158.

$^1$H-NMR (CDCl$_3$, 270 MHz) δ 8.69 (d, J=4.0 Hz, 1H), 7.70 (m, 1H), 7.56 (d, J=8.4 Hz, 2H), 7.53 (dd, J=8.0, 1.1 Hz, 1H), 7.43–7.36 (m, 3H), 7.29–7.24 (m, 3H), 7.12 (m, 1H), 5.39 (dd, J=10.6, 10.2 Hz, 1H), 4.14–4.05 (m, 2H), 3.62 (d, J=14.0 Hz, 1H), 3.21 (d, J=14.0 Hz, 1H), 3.00 (m, 1H), 2.50 (m, 1E), 2.04 (m, 1H), 1.74 (m, 1H)

EXAMPLE 162

Synthesis of Compound 215

Compound 215 (10 mg; yield: 11%) was obtained from Compound 209 (60 mg, 0.17 mmol), 2,3-dichloro-5-pyridinecarboxaldehyde (26 mg, 0.2 mmol), and sodium triacetoxyborohydride (52 mg, 0.25 mmol) in a manner similar to that in Example 159.

$^1$H-NMR (CDCl$_3$, 270 MHz) δ 8.14 (d, J=2.0 Hz, 1H), 7.65 (d, J=2.0 Hz, 1H), 7.55 (dd, J=8.0, 1.3 Hz, 1H), 7.45–7.25 (m, 7H), 7.09 (m, 1H), 5.02 (dd, J=11.2, 9.4 Hz, 1H), 4.07 (m, 1H), 3.86 (d, J=9.4 Hz, 1H), 3.71 (d, J=14.2 Hz, 1H), 3.08–2.88 (m, 2H), 2.48 (m, 1H), 2.08 (m, 1H), 1.72 (m, 1H)

EXAMPLE 163

Synthesis of Compound 216

Compound 216 (52 mg; yield: 64%) was obtained from Compound 208 (60 mg, 0.17 mmol), 3-cyanobenzaldehyde (26 mg, 0.2 mmol), and sodium triacetoxyborohydride (52 mg, 0.25 mmol) in a manner similar to that in Example 158.

$^1$H-NMR (CDCl$_3$, 270 MHz) δ 8.70 (d, J=3.8 Hz, 1H), 7.71 (td, J=7.8, 1.8 Hz, 1H), 7.57–7.35 (m, 7H), 7.30–7.21 (m, 2H), 7.09 (m, 1H), 5.40 (dd, J=11.2, 9.7 Hz, 1H), 4.08–4.05 (m, 2H), 3.61 (d, J=13.7 Hz, 1H), 3.19 (d, J=13.7 Hz, 1H), 3.03 (m, 1H), 2.54 (m, 1H), 2.08 (m, 1H), 1.77 (m, 1H)

EXAMPLE 164

Synthesis of Compound 217 and Compound 218

To a solution (5 mL) of Compound 212 (160 mg, 0.37 mmol) in DMF were added methyl iodide (0.023 mL, 0.37 mmol) and potassium carbonate (50 mg, 0.36 mmol), and the mixture was stirred for 1 hour under cooling with ice. The reaction solution was poured into water and the mixture was extracted with chloroform. The extract was dried over sodium sulfate, and the solvent was evaporated under reduced pressure. The residue was purified by preparative thin layer chromatography (developed with chloroform/methanol=9/1) to obtain Compound 217 (6.7 mg; yield: 4%), Compound 218 (19 mg; yield: 2%), and a mixture thereof (110 mg; yield: 2%).

Compound 217:
$^1$H-NMR (CDCl$_3$, 270 MHz) δ 8.00 (br s, 1H), 7.53 (d, J=8.3 Hz, 1H), 7.43–7.24 (m, 7H), 7.08 (m, 1H), 6.88 (br s, 1H), 5.03 (dd, J=10.9, 9.6 Hz, 1H), 4.05 (m, 1H), 3.73 (d, J=9.6 Hz, 1H), 3.55 (d, J=14.0 Hz, 1H), 3.14–3.02 (m, 2H), 2.27 (m, 1H), 2.05 (m, 1H), 1.61 (m, 1H)

Compound 218:
$^1$H-NMR (CDCl$_3$, 270 MHz) δ 8.02 (br s, 1H), 7.52 (dd, J=7.9, 1.0 Hz, 1H), 7.43–7.24 (m, 7H), 7.06 (m, 1H), 6.58 (br s, 1H), 4.97 (dd, J=11.2, 9.6 Hz, 1H), 3.99 (m, 1H), 3.79 (d, J=9.6 Hz, 1H), 3.65 (s, 3H), 3.62 (d, J=14.0 Hz, 1H), 3.36–3.24 (m, 2H), 2.61 (m, 1H), 2.04 (m, 1H), 1.78 (m, 1H)

EXAMPLE 165

Synthesis of Compound 219

Compound 210 (17 mg, 0.035 mmol) was dissolved in methylene chloride (2.0 mL), and triethylamine (0.048 mL, 0.36 mmol) and nicotinoyl chloride (26 mg, 0.14 mmol) were added to the solution, followed by stirring at room temperature for 2 hours. The reaction mixture was worked up in a usual manner and purified by preparative thin layer chromatography (developed with chloroform/methanol=98/5) to obtain Compound 219 (13 mg; yield: 61%).

$^1$H-NMR (CDCl$_3$, 300 MHz) δ 8.68–8.66 (m, 2H), 7.81–7.77 (m, 1H) 7.58–7.55 (m, 1H), 7.38–7.33 (m, 1H), 7.26–7.01 (m, 5H), 6.92–6.88 (m, 1H), 5.71 (d, J=5.0 Hz, 1H), 5.48–5.43 (m, 1H), 5.25–5.18 (m, 4H), 4.26–4.12 (m, 2H), 3.77–3.68 (m, 1H), 3.53 (s, 3H), 3.51 (s, 3H), 2.33–2.21 (m, 1H), 1.98–1.85 (m, 1H)

EXAMPLE 166

Synthesis of Compound 220

Compound 219 (8.3 mg, 0.014 mmol) was dissolved in ethyl acetate (2 mL), and a 4 mol/l solution (0.20 mL) of hydrochloric acid in ethyl acetate was added thereto under cooling with ice, followed by stirring for 4 hours for the removal of the protective group. After completion of the reaction, the solvent was evaporated under reduced pressure. A chloroform/methanol (90/10) mixed solvent was added to the residue, and the mixture was washed with a saturated aqueous solution of sodium hydrogen carbonate and dried over sodium sulfate. The solvent was evaporated under reduced pressure, and the residue was purified by preparative thin layer chromatography (developed with chloroform/methanol=90/10) to obtain Compound 220 (4.1 mg; yield: 58%).

$^1$H-NMR (CD$_3$OD, 300 MHz) δ 8.63–8.57 (m, 2H), 7.88–7.83 (m, 1H) 7.58–7.47 (m, 2H), 7.30–7.28 (m, 2H), 7.17–7.11 (m, 1H), 6.85–6.68 (m, 3H), 5.66–5.58 (m, 2H), 4.18–3.96 (m, 2H), 3.88–3.78 (m, 1H), 2.36–2.24 (m, 1H), 1.99–1.86 (m, 1H)

EXAMPLE 167

Synthesis of Compound 221

Compound 210 (17 mg, 0.035 mmol) was dissolved in DMF (2.0 mL), and 3-pyridylacetic acid monohydrochloride (38 mg, 0.22 mmol) and N,N-dicyclohexylcarbodiimide (45 mg, 0.22 mmol) were added thereto, followed by stirring at room temperature for 2 hours. The reaction mixture was filtered, and the filtrate was washed with a saturated aqueous solution of sodium hydrogen carbonate and dried over sodium sulfate. The solvent was evaporated under reduced pressure, and the residue was purified by preparative thin layer chromatography (developed with chloroform/methanol=95/5) to obtain Compound 221 (15 mg; yield: 30%).

$^1$H-NMR (CDCl$_3$, 300 MHz) δ 8.52–8.46 (m, 2H), 7.64–7.53 (m, 2H), 7.29–7.06 (m, 4H), 7.01–6.96 (m, 2H), 6.80 (d, J=8.4 Hz, 1H), 5.93–5.92 (m, 1H), 5.44–5.41 (m, 1H), 5.39–5.14 (m, 4H), 4.26–4.22 (m, 1H), 4.05–4.02 (m, 1H), 3.84–3.70 (m, 2H), 3.63–3.57 (m, 1H), 3.52 (s, 3H), 3.49 (s, 3H), 2.22–2.15 (m, 1H), 1.95–1.69 (m, 1H)

EXAMPLE 168

Synthesis of Compound 222

Compound 221 (14 mg, 0.24 mmol) was dissolved in ethyl acetate (4 mL), and a 4 mol/l solution (0.60 mL) of hydrochloric acid in ethyl acetate was added thereto under cooling with ice, followed by stirring for 3 hours to remove the protective group. After the reaction, the solvent was evaporated under reduced pressure, and to the residue was added a chloroform/methanol (90/10) mixed solvent. The mixture was washed with a saturated aqueous sodium hydrogen carbonate solution and dried over sodium sulfate. The solvent was evaporated under reduced pressure, and the residue was purified by preparative thin layer chromatography (developed with chloroform/methanol=90/10) to obtain Compound 222 (6.3 mg; yield: 5.0%).

$^1$H-NMR (CD$_3$OD, 300 MHz) δ 8.43–8.41 (m, 2H), 7.73–7.70 (m, 1H), 7.56–7.54 (m, 1H), 7.42–7.38 (m, 1H), 7.32–7.10 (m, 3H), 6.82–6.75 (m, 2H), 6.67–6.63 (m, 1H), 5.82 (d, J=6.1 Hz, 1H), 5.61–5.56 (m, 1H), 4.28–4.19 (m, 1H), 4.06–3.95 (m, 1H), 3.89 (d, J=8.1 Hz, 2H), 3.78–3.68 (m, 1H), 2.29–2.17 (m, 1H), 1.96–1.84 (m, 1H)

EXAMPLE 169

Synthesis of Compound 223

Step 1:
To a DMF solution (20 mL) of 4-hydroxymethylimidazole hydrochloride (880 mg, 6.5 mmol) was added triethylamine (2.3 mL, 16 mmol). After 10 minutes of stirring at room temperature, a solution (15 mL) of trityl chloride (2.0 g, 7.3 mmol) in DMF was dropwise added thereto. The reaction mixture was stirred overnight under a nitrogen atmosphere. Thereafter, the reaction solution was poured into ice water and the mixture was filtered. The resulting solid was washed with cold dioxane and dried under reduced pressure to obtain an N-trityl compound of 4-hydroxymethylimidazole (2.2 g; yield: 100%) as a white powder.

$^1$H-NMR (CD$_3$COOD, 250 MHz) δ 8.56 (d, 1H), 7.57–7.40 (m, 7H) 7.38–7.18 (m, 9H), 4.78 (s, 2H)
EI-MS m/z 363 (M+Na)$^+$

Step 2:
To the N-trityl compound obtained in Step 1 (2.2 g, 6.5 mmol) suspended in pyridine (15 mL) was added acetic anhydride (2.0 mL, 20 mmol) in 5 portions over 30 minutes. The reaction mixture was then stirred under a nitrogen atmosphere overnight. After the reaction mixture had become homogeneous, the reaction mixture was extracted with ethyl acetate. The extract was washed with water three times, with 5% hydrochloric acid twice, and with a saturated aqueous sodium bicarbonate solution twice. The resulting organic layer was then dried over magnesium sulfate and the solvent was evaporated under reduced pressure to obtain an O-acetyl compound (2.3 g; yield: 92%) as a white solid.

$^1$H-NMR (CDCl$_3$, 250 MHz) δ 8.61 (d, 1H), 7.38–7.26 (m, 9H), 7.18–7.07 (m, 7H), 5.05 (s, 2H), 2.07 (s, 3H)
EI-MS m/z 405 (M+Na)$^+$

Step 3:
To the N-trityl-O-acetyl compound obtained in Step 2 (2.3 g, 6.1 mmol) in ethyl acetate (20 mL) was added 4-cyanobenzyl bromide (1.3 g, 6.7 mmol). The reaction mixture was heated to 60° C. and stirred at the same temperature overnight. Thereafter, the resulting white precipitate was collected by filtration and the resulting solid material was dissolved in methanol (20 mL). The mixture was heated to 60° C. and stirred at the same temperature for 2 hours. The reaction solution was cooled and the solvent was evaporated under reduced pressure. The resulting residue was triturated with hexane to obtain an N-(4-cyanobenzyl) compound (1.4 g; yield: 68%) as a white powder.

$^1$H-NMR (CD$_3$OD, 250 MHz) δ 7.80–7.75 (m, 2H), 7.75–7.62 (m, 1H), 7.56–7.47 (m, 2H), 7.30–7.23 (m, 1H), 5.72 (s, 2H), 5.20 (s, 2H), 1.90 (s, 3H)
EI-MS m/z 256 (M+H)$^+$

Step 4:
To the N-(4-cyanobenzyl)-O-acetyl compound obtained in Step 3 (1.4 g, 4.1 mmol) in a tetrahydrofuran/water (3/1) mixed solvent (20 mL) was added lithium hydroxide (0.52 g, 12.3 mmol). The reaction mixture was stirred at room temperature for 1 hour. After the reaction, the reaction mixture was extracted with ethyl acetate. The extract was washed with water twice, with a saturated aqueous sodium bicarbonate solution twice, and with a saturated brine once, and then dried over magnesium sulfate. The solvent was evaporated under reduced pressure to obtain a deacetylated compound (0.53 g; yield: 60%) as a yellow brown solid.

$^1$H-NMR (CD$_3$OD, 250 MHz): δ 7.68–7.55 (m, 3H), 7.22 (d, 2H), 6.89 (s, 1H), 5.30 (s, 2H), 4.76 (s, 2H), 4.34 (s, 1H)
EI-MS m/z 213 (M+H)$^+$; EI-MS m/z 211 (M-H)$^-$

Step 5:
To the deacetylated compound obtained in Step 4 (0.13 g, 0.61 mmol) in DMF (5.0 mL) was added triethylamine (0.34 mL, 2.4 mmol) and a sulfur trioxide pyridine complex (0.24 g, 1.5 mmol). The mixture was stirred at room temperature for 40 minutes under a nitrogen atmosphere. After the reaction, the reaction mixture was extracted with ethyl acetate. The extract was washed with water twice and with a saturated aqueous solution of sodium bicarbonate twice, and then dried over magnesium sulfate. Then, the solvent was evaporated under reduced pressure to obtain a crude aldehyde compound. The crude aldehyde compound was then dissolved in methylene chloride (2 mL) under a nitrogen atmosphere. To this solution was added Compound 209 (220 mg, 0.61 mmol) along with sodium triacetoxyborohydride (190 mg, 0.92 mmol) under cooling with ice and the reaction mixture was stirred overnight while being left to warm to room temperature. Thereafter, water was poured into the reaction solution and the mixture was extracted with ethyl acetate. The extract was washed with a saturated aqueous sodium bicarbonate solution and dried over sodium sulfate. The solvent was evaporated under reduced pressure and the resulting residue was purified by silica gel chromatography to obtain Compound 223 (6.4 mg; yield: 1.9%).

$^1$H-NMR (CD$_3$OD, 250 MHz) δ 7.58 (t, 3H), 7.45 (d, 1H), 7.38–7.10 (m, 7H), 7.04 (dt, 1H), 6.95 (d, 2H), 6.81 (s, 1H), 4.78 (s, 4H), 3.91 (td, 1H), 3.56 (d, 1H), 2.92 (dt, 1H), 2.21 (td, 2H), 1.55–1.32 (m, 2H)
EI-MS m/z 556 and 558 (M+H)$^+$; EI-MS m/z 554 and 556 (M-H)$^-$ Structures and physical properties of the compounds in Reference Examples are shown in Tables 10 to 12.

TABLE 10

(I)-1

| Compound No. | $R^{1a}, R^{1b}, R^{1c}$ | $R^{2a}, R^{2b}, R^{2c}$ | MS m/z $(M + H)^+$ |
|---|---|---|---|
| A | 2-Br | 4-OH | 484, 482 |
| B | 2-CH=CHCH$_3$ | 4-OH | 444 |
| C | 2-SCH$_3$ | 4-OH | 450 |
| D | 2-Br, 4-CH$_3$ | 4-OH | 498, 496 |
| E | 2,4-(CH$_3$)$_2$ | 4-OH | 432 |
| F | 2-Cl | 4-OH | 438 |
| G | 2-Br | 3,4-(OH)$_2$ | 500, 498 |
| H | 2-I | 3,4-(OH)$_2$ | 546 |
| I | 2-CH$_2$CH$_3$ | 3,4-(OH)$_2$ | 448 |
| J | 2-CH(—OCH$_2$CH$_2$O—) | 3,4-(OH)$_2$ | 492 |
| K | 2-CH(—SCH$_2$CH$_2$S—) | 3,4-(OH)$_2$ | 524 |
| L | 2-CH=CHCH$_3$ | 3,4-(OH)$_2$ | 460 |
| M | 2,6-Cl$_2$ | 3,4-(OH)$_2$ | 490, 488 |
| N | 2,5-Cl$_2$ | 3,4-(OH)$_2$ | 490, 488 |
| O | 2,3,5-Cl$_3$ | 3,4-(OH)$_2$ | 524, 522 |
| P | 3,5-Br$_2$ | 3,4-(OH)$_2$ | 580, 578, 576 |
| Q | 2-Br | H | 468, 466 |
| R | 2-Br | 3-OCH$_3$, 4-OH | 514, 512 |
| S | 2-Br | 3,4-(OCH$_3$)$_2$ | 528, 526 |
| T | 2-Br | 4-OCH$_3$ | 498, 496 |
| U | 2-Br | 3,4-[(NHCOOC(CH$_3$)$_3$]$_2$ | 698, 696 |
| V | 2-Br | 3,5-(CH$_3$)$_2$, 4-OH | 512, 510 |
| W | 2-Br | 3-I, 4-OCH$_2$OCH$_3$ | 653, 651 |
| X | 2-Br | 3-I, 4-OH | 609, 607 |
| Y | 2-Br | 2-NO$_2$ | 513, 511 |
| Z | 2-Br | 3-NO$_2$ | 513, 511 |
| AA | 2-CH$_2$CH$_2$ | 4-OH | 432 |
| AB | 2-CH$_2$CH$_3$ | 3,5-(OCH$_3$)$_2$, 4-OH | 492 |
| AC | 2-CH$_2$CH$_3$ | 3-I, 4-OCH$_2$OCH$_3$ | 602 |
| AD | 3-Br | 4-OH | 484, 482 |

TABLE 11
(I)-2
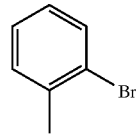
| Compound No. | R¹ | R² | MS m/z (M + H)⁺ |
|---|---|---|---|
| AE | 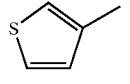 | 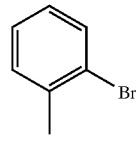 | 474, 472 |
| AF | 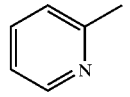 | 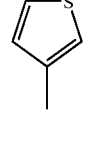 | 469, 467 |
| AG | 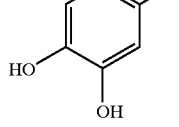 | 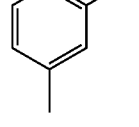 | 426 |
| AH | 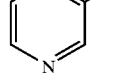 | 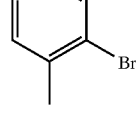 | 423 |
| AI | 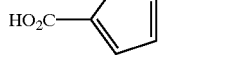 | 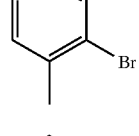 | 516 |
| AJ | 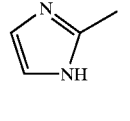 | 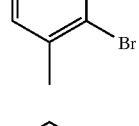 | 458, 456 |
| AK | 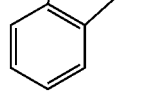 | 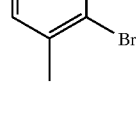 | 507, 505 |
| AL | 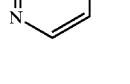 | | 469, 467 |

TABLE 11-continued
(I)-2
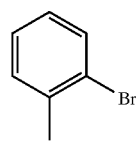
| Compound No. | R¹ | R² | MS m/z (M + H)⁺ |
| --- | --- | --- | --- |
| AM | 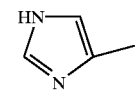 | 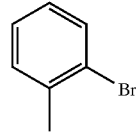 | 458, 456 |
| AN | 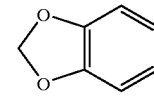 | 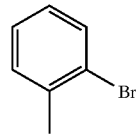 | 458, 456 |
| AO | 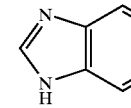 | 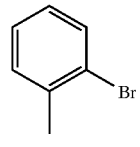 | 508, 506 |
| AP | 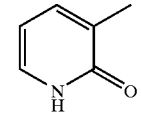 | 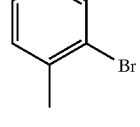 | 485, 483 |
| AQ | 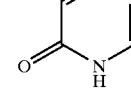 | 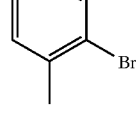 | 485, 483 |
| AR | 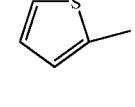 | 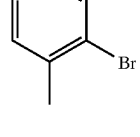 | 473, 471*¹ |
| AS | 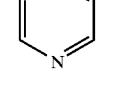 | 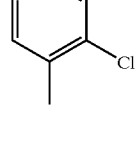 | 469, 467 |
| AT | 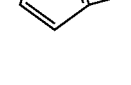 | | 428 |

TABLE 11-continued
(I)-2
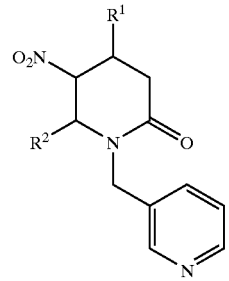
| Compound No. | R¹ | R² | MS m/z (M + H)⁺ |
|---|---|---|---|
| AU | 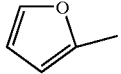 | 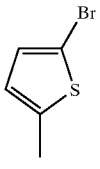 | 458, 456 |
| AV | 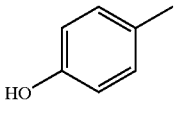 | 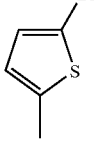 | 490, 488 |
| AW | 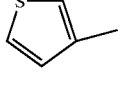 | 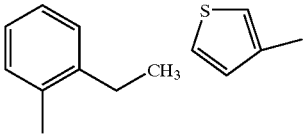 | 480, 478 |
| AX | 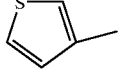 | 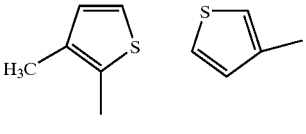 | 422 |
| AY | 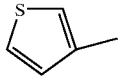 | 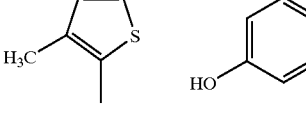 | 428 |
| AZ | 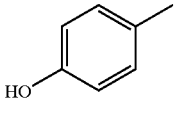 | 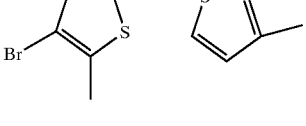 | 424 |
| BA | 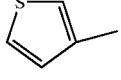 | 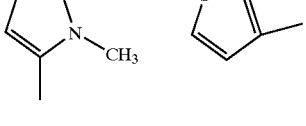 | 480, 478 |
| BB | 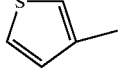 | | 397 |

TABLE 11-continued (I)-2

| Compound No. | R¹ | R² | MS m/z (M + H)⁺ |
|---|---|---|---|
| BC | benzyl | 3-pyridylmethyl | Not tested |
| BD | benzyl | 2-methylbenzyl | 418 |
| BE | 2-bromobenzyl | 3-methylfuran-... | 458, 456 |
| BF | 2-methylbenzyl | 2-methylpyridyl | 417 |
| BG | 1-phenylethyl (CH₃) | 4-hydroxyphenylmethyl | 432 |
| BH | 2-methylbenzyl | 4-methyl-1H-pyrazolyl | 406 |
| BI | 2-methylbenzyl | 4,5-dimethyl-1H-imidazolyl | 420 |
| BJ | 2-methylbenzyl | 4-methyl-1,2,3-thiadiazolyl | 424 |

TABLE 11-continued (I)-2

| Compound No. | R¹ | R² | MS m/z (M + H)⁺ |
|---|---|---|---|
| BK | 2-methylphenyl-CH₂CH₂- | 1,2-dimethylimidazol-5-yl- | 420 |
| BL | 2-methylphenyl-CH₂CH₂- | 4-methyl-2-nitrothiophen-5-yl- | 467 |
| BM | 2-bromo-methylphenyl- | 4-methyl-2-nitrothiophen-5-yl- | 519, 517 |
| BN | 2-bromo-methylphenyl- | 3-methylthiophen-2-yl- | 488, 486 |
| BO | 2-(methylthio)-methylphenyl- | 4-methylphenyl- | 434 |
| BP | 2-(methylthio)-methylphenyl- | 6-methylpyridin-2-yl- | 435 (ESI) |
| BQ | 2-(methylthio)-methylphenyl- | 4-methylthiophen-3-yl- | 440 (ESI) |
| BR | 2-methylphenyl-CH=CH-CH₃ | 4-methylthiophen-3-yl- | 424 (ESI) |

TABLE 11-continued
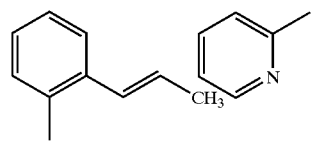
(I)-2
| Compound No. | R¹ | R² | MS m/z (M + H)⁺ |
|---|---|---|---|
| BS |  | 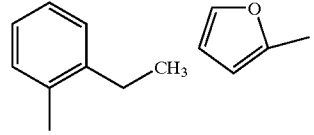 | 429 (ESI) |
| BT |  | 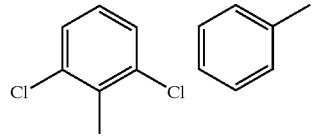 | 406 (ESI) |
| BU |  | 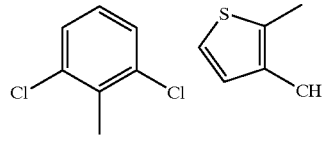 | 456 (ESI) |
| BV |  | 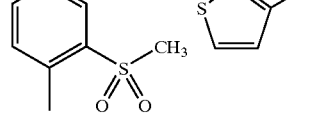 | 476 (FAB) |
| BW |  | 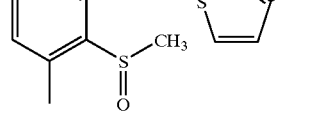 | 472 (FAB) |
| BX |  | 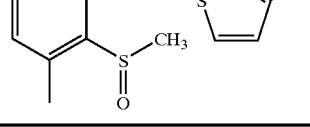 | 456 (FAB) |
| BY*² |  |  | 456 (FAB) |
*¹: (M⁺)
*²: an isomer of Compound BX based upon a sulfur atom

TABLE 12

| Compound No. | | MS m/z (M + H)+ |
|---|---|---|
| BZ | 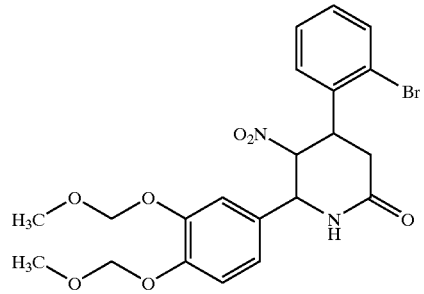 | 497, 495 (FAB) |

REFERENCE EXAMPLE 1

Synthesis of Compound A

Methyl 3-(2-bromophenyl)-4-nitrobutyrate (300 mg, 1.0 mmol), 4-hydroxybenzaldehyde (100 mg, 0.80 mmol), and 3-aminomethylpyridine (0.20 mL, 2.0 mmol) were heated under reflux in ethanol for 48 hours. Ethanol was evaporated under reduced pressure, and the residue was purified by silica gel column chromatography (eluted with chloroform/methanol=95/5) to obtain Compound A (87 mg; yield: 18%).

$^1$H-NMR (DMSO-$d_6$, 300 MHz) δ 9.62 (s, 1H), 8.38 (d, J=4.8 Hz, 1H), 8.11 (s, 1H), 7.78 (d, J=7.9 Hz, 1H), 7.61 (d, J=7.9 Hz, 1H), 7.46–7.39 (m, 2H), 7.27–7.22 (m, 2H), 7.14 (d, J=8.0 Hz, 2H), 6.64 (d, J=8.0 Hz, 2H), 5.89 (dd, J=11.0, 9.5 Hz, 1H), 4.94 (d, J=9.5 Hz, 1H), 4.47 (d, J=15.8 Hz, 1H), 4.38 (m, 1H), 4.18 (d, J=15.8 Hz, 1H), 3.05 (dd, J=16.8, 11.0 Hz, 1H), 2.74 (dd, J=16.8, 4.7 Hz, 1H)

REFERENCE EXAMPLE 2

Synthesis of Compound B

Compound B (1.3 g; yield: 34%) was obtained from methyl 3-[2-((E)-1-propenyl)phenyl]-4-nitrobutyrate (2.3 g, 8.7 mmol), 4-hydroxybenzaldehyde (1.1 g, 8.7 mmol), and 3-aminomethylpyridine (1.77 mL, 17.4 mmol) in a manner similar to that in Reference Example 1.

$^1$H-NMR (DMSO-$d_6$, 270 MHz) δ 9.50 (br s, 1H), 8.41 (d, J=4.2 Hz, 1H), 8.19 (br s, 1H), 7.65 (d, J=7.5 Hz, 1H), 7.47 (d, J=8.9 Hz, 1H), 7.34–7.12 (m, 6H), 6.88–6.62 (m, 3H), 6.10 (dq, J=15.0, 6.2 Hz, 1H), 5.73 (dd, J=11.0, 10.0 Hz, 1H), 4.78 (d, J=10.0 Hz, 1H), 4.67 (d, J=15.4 Hz, 1H), 4.32 (ddd, J=12.9, 11.0, 4.4 Hz, 1H), 3.99 (d, J=15.4 Hz, 1H), 3.01 (dd, J=17.2, 12.9 Hz, 1H), 2.65 (dd, J=17.2, 4.4 Hz, 1H), 1.89 (d, J=6.2 Hz, 3H)

REFERENCE EXAMPLE 3

Synthesis of Compound C

Compound C (3.2 g; yield: 73%) was obtained from methyl 3-(2-methylthiophenyl)-4-nitrobutyrate (2.7 g, 10 mmol), 4-hydroxybenzaldehyde (1.2 g, 10 mol), and 3-aminomethylpyridine (1.77 mL, 17.4 mmol) in a manner similar to that in Reference Example 1.

$^1$H-NMR (DMSO-$d_6$, 270 MHz) δ 9.61 (br s, 1H), 8.37 (d, J=4.3 Hz, 1H), 8.10 (br s, 1H), 7.62 (d, J=7.3 Hz, 1H), 7.40–7.11 (m, 7H), 6.62 (d, J=8.3 Hz, 2H), 5.87 (dd, J=10.9, 9.9 Hz, 1H), 4.89 (d, J=9.9 Hz, 1H), 4.38 (d, J=15.5 Hz, 1H), 4.26 (m, 1H), 4.15 (d, J=15.5 Hz, 1H), 2.98 (dd, J=16.8, 12.9 Hz, 1H), 2.68 (dd, J=16.8, 5.0 Hz, 1H), 2.44 (s, 3H)

REFERENCE EXAMPLE 4

Synthesis of Compound D

Compound D (165 mg; yield: 67%) was obtained from methyl 3-(2-bromo-4-methylphenyl)-4-nitrobutyrate (157 mg, 0.5 mmol), 4-hydroxybenzaldehyde (61 mg, 0.5 mmol), and 3-aminomethylpyridine (0.1 mL, 1.0 mmol) in a manner similar to that in Reference Example 1.

$^1$H-NMR (DMSO-$d_6$, 300 MHz) δ 9.63 (s, 1H), 8.38 (d, J=3.6 Hz, 1E), 8.10 (br s, 1H), 7.65 (d, J=8.2 Hz, 1H), 7.44 (br s, 1H), 7.40 (dd, J=6.0, 1.8 Hz, 1H), 7.26–7.22 (m, 2H), 7.13 (d, J=8.6 Hz, 2H), 6.63 (d, J=8.6 Hz, 2H), 5.85 (dd, J=11.2, 9.8 Hz, 1H), 4.91 (d, J=9.8 Hz, 1H), 4.47 (d, J=15.5 Hz, 1H), 4.31 (m, 1H), 4.17 (d, J=15.5 Hz, 1H), 2.99 (dd, J=17.0, 13.2 Hz, 1H), 2.70 (dd, J=17.0, 5.3 Hz, 1H), 2.26 (s, 3H)

REFERENCE EXAMPLE 5

Synthesis of Compound E

Compound E (130 mg; yield: 60%) was obtained from methyl 3-(2,4-dimethylphenyl)-4-nitrobutyrate (125 mg, 0.5 mmol), 4-hydroxybenzaldehyde (61 mg, 0.5 mmol), and 3-aminomethylpyridine (0.10 mL, 1.0 mmol) in a manner similar to that in Reference Example 1.

$^1$H-NMR (DMSO-$d_6$, 270 MHz) δ 8.39 (d, J=4.6 Hz, 1H), 8.31 (br s, 1H), 7.50 (d, J=7.9 Hz, 1H), 7.43 (d, J=7.3 Hz, 1H), 7.25 (dd, J=7.3, 5.0 Hz, 1H), 7.10 (d, J=8.0 Hz, 2H), 7.02 (d, J=7.9 Hz, 1H), 6.94 (s, 1H), 6.64 (d, J=8.0 Hz, 2H), 5.71 (dd, J=10.9, 9.9 Hz, 1H), 4.85 (d, J=9.9 Hz, 1H), 4.57 (d, J=15.5 Hz, 1H), 4.18–4.05 (m, 2H) 3.00 (dd, J=17.5, 13.2 Hz, 1H), 2.68 (dd, J=17.5, 4.9 Hz, 1H), 2.28 (s, 3H), 2.21 (s, 3H)

REFERENCE EXAMPLE 6

Synthesis of Compound F

Compound F (1.3 g; yield: 55%) was obtained from methyl 3-(2-chlorophenyl)-4-nitrobutyrate (1.4 g, 5.4 mmol), 4-hydroxybenzaldehyde (660 mg, 5.4 mmol) and 3-aminomethylpyridine (1.1 mL, 11 mmol) in a manner similar to that in Reference Example 1.

$^1$H-NMR (DMSO-$d_6$, 300 MHz) δ 9.77 (s, 1H), 8.52 (dd, J=4.6, 1.7 Hz, 1H), 8.25 (d, J=1.7 Hz, 1H), 7.92 (d, J=6.6 Hz,

1H), 7.59–7.36 (m, 5H), 7.26 (d, J=8.6 Hz, 2H), 6.77 (d, J=8.6 Hz, 2H), 5.99 (dd, J=11.4, 9.9 Hz, 1H), 5.06 (d, J=9.9 Hz, 1H), 4.64 (d, J=15.5 Hz, 1H), 4.56 (m, 1H), 4.28 (d, J=15.5 Hz, 1H), 3.18 (dd, J=17.2, 12.9 Hz, 1H), 2.88 (dd, J=17.2, 5.0 Hz, 1H)

REFERENCE EXAMPLE 7

Synthesis of Compound G

Compound G (47 mg; yield: 19%) was obtained from methyl 3-(2-bromophenyl)-4-nitrobutyrate (150 mg, 0.5 mmol), 3,4-dihydroxybenzaldehyde (69 mg, 0.5 mmol) and 3-aminomethylpyridine (0.10 mL, 1.0 mmol) in a manner similar to that in Reference Example 1.

$^1$H-NMR (DMSO-$d_6$, 300 MHz) δ 9.23 (s, 1H), 8.95 (s, 1H), 8.43 (dd, J=4.6, 1.5 Hz, 1H), 8.18 (d, J=2.0 Hz, 1H), 7.79 (d, J=7.2 Hz, 1H), 7.61 (dd, J=7.8, 1.1 Hz, 1H), 7.47–7.41 (m, 2H), 7.29 (dd, J=7.8, 4.7 Hz, 1H), 7.22 (dt, J=7.8, 1.5 Hz, 1H), 6.75 (d, J=2.0 Hz, 1H), 6.64 (d, J=8.1 Hz, 1H), 6.56 (dd, J=8.1, 2.0 Hz, 1H), 5.84 (dd, J=11.3, 9.8 Hz, 1H), 4.80 (d, J=9.8 Hz, 1H), 4.65 (d, J=15.6 Hz, 1H), 4.35 (m, 1H), 3.99 (d, J=15.6 Hz, 1H), 3.02 (dd, J=16.9, 12.5 Hz, 1H), 2.72 (dd, J=16.9, 4.6 Hz, 1H)

REFERENCE EXAMPLE 8

Synthesis of Compound H

Compound H (5.3 g; yield: 47%) was obtained from methyl 3-(2-iodophenyl)-4-nitrobutyrate (7.1 g, 20 mmol), 3,4-dihydroxybenzaldehyde (2.8 g, 20 mmol) and 3-aminomethylpyridine (4.1 ml, 40 mmol) in a manner similar to that in Reference Example 1.

$^1$H-NMR (DMSO-$d_6$, 300 MHz) δ 8.93 (br s, 2H), 8.42 (dd, J=4.8, 1.6 Hz, 1H), 8.18 (d, J=1.6 Hz, 1H), 7.84 (dd, J=8.0, 1.3 Hz, 1H), 7.74 (d, J=7.2 Hz, 1H), 7.46–7.40 (m, 2H), 7.27 (dd, J=4.7, 0.7 Hz, 1H), 7.03 (td, J=8.0, 1.2 Hz, 1H), 6.77 (d, J=1.9 Hz, 1H), 6.64 (d, J=8.1 Hz, 1H), 6.59 (dd, J=8.1, 1.9 Hz, 1H), 5.76 (dd, J=10.4, 9.8 Hz, 1H), 4.79 (d, J=9.8 Hz, 1H), 4.65 (d, J=15.4 Hz, 1H), 4.16 (m, 1H), 4.03 (d, J=15.4 Hz, 1H), 2.98 (dd, J=16.9, 13.0 Hz, 1H), 2.69 (dd, J=16.9, 5.1 Hz, 1H)

REFERENCE EXAMPLE 9

Synthesis of Compound I

Compound I (57 mg; yield: 13%) was obtained from methyl 3-(2-ethylphenyl)-4-nitrobutyrate (251 mg, 1.0 mmol), 3,4-dihydroxybenzaldehyde (138 mg, 1.0 mmol) and 3-aminomethylpyridine (0.20 mL, 2.0 mmol) in a manner similar to that in Reference Example 1.

$^1$H-NMR (DMSO-$d_6$, 300 MHz) δ 9.20 (br s, 1H), 8.92 (br s, 1H), 8.41 (d, J=4.8 Hz, 1H), 8.18 (br s, 1H), 7.66 (d, J=7.0 Hz, 1H), 7.46 (d, J=8.1 Hz, 1H), 7.28 (m, 1H), 7.19–7.15 (m, 3H), 6.73 (s, 1H), 6.62 (d, J=8.1 Hz, 1H), 6.53 (d, J=8.1 Hz, 1H), 5.75 (dd, J=10.8, 10.1 Hz, 1H), 4.78 (d, J=10.1 Hz, 1H), 4.65 (d, J=15.4 Hz, 1H), 4.17 (m, 1H), 4.00 (d, J=15.4 Hz, 1H), 3.17 (dd, J=17.2, 12.6 Hz, 1H), 2.70–2.44 (m, 3H), 1.13 (d, J=7.4 Hz, 3H)

REFERENCE EXAMPLE 10

Synthesis of Compound J

Compound J (162 mg; yield: 34%) was obtained from methyl 3-[2-(1,3-dioxolan-2-yl)phenyl]-4-nitrobutyrate (280 mg, 0.96 mmol), 3,4-dihydroxybenzaldehyde (132 mg, 0.96 mmol) and 3-aminomethylpyridine (0.20 mL, 1.9 mmol) in a manner similar to that in Reference Example 1.

$^1$H-NMR (DMSO-$d_6$, 300 MHz) δ 9.00 (br s, 2H), 8.42 (dd, J=4.7, 1.5 Hz, 1H), 8.19 (d, J=1.9 Hz, 1H), 7.76 (d, J=7.5 Hz, 1H), 7.49–7.38 (m, 3H), 7.32–7.26 (m, 2H), 6.76 (d, J=2.0 Hz, 1H), 6.64 (d, J=8.1 Hz, 1H), 6.55 (dd, J=8.1, 2.0 Hz, 1H), 5.98 (s, 1H), 5.83 (dd, J=11.6, 9.7 Hz, 1H), 4.77 (d, J=9.7 Hz, 1H), 4.70 (d, J=15.4 Hz, 1H), 4.08–3.94 (m, 6H), 3.01 (dd, J=17.1, 12.9 Hz, 1H), 2.69 (dd, J=17.1, 4.7 Hz, 1H)

REFERENCE EXAMPLE 11

Synthesis of Compound K

Ethanedithiol (0.063 mL, 0.75 mmol) and a boron trifluoride diethyl ether complex (0.095 mL, 0.75 mmol) were added to a methylene chloride solution (10 mL) of Compound J (74 mg, 0.15 mmol) under cooling with ice, and the mixture was stirred at that temperature for 1 hour. The precipitated powder was collected by filtration and dissolved in chloroform/methanol (1/9), and the solution was neutralized with a saturated aqueous solution of sodium hydrogencarbonate and extracted with chloroform/methanol (1/9). The solvent was evaporated under reduced pressure, and the resulting residue was purified by preparative thin layer chromatography (developed with chloroform/methanol=95/5) to obtain Compound K (41 mg; yield: 52%).

$^1$H-NMR (DMSO-$d_6$, 300 MHz) δ 9.19 (s, 1H), 8.92 (s, 1H), 8.42 (d, J=4.0 Hz, 1H), 8.22 (br s, 1H), 7.77 (d, J=7.4 Hz, 1H), 7.67 (d, J=7.4 Hz, 1H), 7.48 (d, J=7.4 Hz, 1H), 7.31–7.26 (m, 3H), 6.73 (d, J=2.0 Hz, 1H), 6.64 (d, J=8.1 Hz, 1H), 6.52 (dd, J=8.1, 2.0 Hz, 1H), 6.18 (s, 1H), 5.80 (dd, J=10.8, 10.1 Hz, 1H), 4.77 (d, J=10.1 Hz, 1H), 4.70 (d, J=15.4 Hz, 1H), 4.49 (m, 1H), 3.95 (d, J=15.4 Hz, 1H), 3.58–3.38 (m, 4H), 2.99 (dd, J=17.0, 12.7 Hz, 1H), 2.69 (dd, J=17.0, 5.1 Hz, 1H)

REFERENCE EXAMPLE 12

Synthesis of Compound L

Compound L (6.2 mg; yield: 6.8%) was obtained from methyl 3-[2-((E)-1-propenyl)phenyl]-4-nitrobutyrate (52 mg, 0.20 mmol), 3,4-dihydroxybenzaldehyde (28 mg, 0.20 mmol) and 3-aminomethylpyridine (0.041 mL, 0.40 mmol) in a manner similar to that in Reference Example 1.

$^1$H-NMR (DMSO-$d_6$, 300 MHz) δ 9.20 (br s, 1H), 8.90 (br s, 1H), 8.41 (d, J=4.2 Hz, 1H), 8.19 (br s, 1H), 7.65 (d, J=7.5 Hz, 1H), 7.47 (d, J=8.9 Hz, 1H), 7.40 (d, J=8.9 Hz, 1H), 7.30–7.19 (m, 3H), 6.86 (d, J=15.0 Hz, 1H), 6.73 (s, 1H), 6.62 (d, J=8.3 Hz, 1H), 6.58 (d, J=8.3 Hz, 1H), 6.10 (dq, J=15.0, 6.2 Hz, 1H), 5.73 (dd, J=11.0, 10.0 Hz, 1H), 4.78 (d, J=10.0 Hz, 1H), 4.67 (d, J=15.6 Hz, 1H), 4.32 (ddd, J=12.9, 11.0, 4.4 Hz, 1H), 3.99 (d, J=15.6 Hz, 1H), 3.01 (dd, J=17.2, 12.9 Hz, 1H), 2.65 (dd, J=17.2, 4.4 Hz, 1H), 1.90 (d, J=6.2 Hz, 3H)

REFERENCE EXAMPLE 13

Synthesis of Compound M

Compound M (86 mg; yield: 8.8%) was obtained from methyl 3-(2,6-dichlorophenyl)-4-nitrobutyrate (590 mg, 2.0 mmol), 3,4-dihydroxybenzaldehyde (262 mg, 1.9 mmol) and 3-aminomethylpyridine (0.40 mL, 4.0 mmol) in a manner similar to that in Reference Example 1.

$^1$H-NMR (DMSO-$d_6$, 300 MHz) δ 9.21 (s, 1H), 9.03 (s, 1H), 8.42 (d, J=5.9 Hz, 1H), 8.21 (br s, 1H), 7.53–7.47 (m,

3H), 7.39–7.27 (m, 2H), 6.67–6.65 (m, 2H), 6.53 (d, J=7.3 Hz, 1H), 5.97 (dd, J=11.7, 9.7 Hz, 1H), 4.93 (d, J=9.7 Hz, 1H), 4.86–4.70 (m, 2H), 3.99 (d, J=15.1 Hz, 1H), 3.47 (dd, J=16.5, 13.8 Hz, 1H), 2.84 (dd, J=16.5, 4.6 Hz, 1H)

REFERENCE EXAMPLE 14

Synthesis of Compound N

Compound N (92 mg; yield: 26%) was obtained from methyl 3-(2,5-dichlorophenyl)-4-nitrobutyrate (210 mg, 0.72 mmol), 3,4-dihydroxybenzaldehyde (99 mg, 0.72 mmol) and 3-aminomethylpyridine (0.14 mL, 1.4 mmol) in a manner similar to that in Reference Example 1.

$^1$H-NMR (DMSO-$d_6$, 400 MHz) δ 9.22 (s, 1H), 8.93 (s, 1H), 8.41 (dd, J=4.8, 1.6 Hz, 1H), 8.18 (d, J=1.6 Hz, 1H), 8.00 (d, J=1.6 Hz, 1H), 7.48 (d, J=8.6 Hz, 1H), 7.45 (dt, J=7.8, 1.9 Hz, 1H), 7.38 (dd, J=9.8, 2.5 Hz, 1H), 7.28 (ddd, J=0.7, 4.9, 7.8 Hz, 1H), 6.73 (d, J=2.0 Hz, 1H), 6.64 (d, J=8.1 Hz, 1H), 6.53 (dd, J=8.1, 2.0 Hz, 1H), 5.86 (dd, J=11.5, 9.8 Hz, 1H), 4.81 (d, J=9.8 Hz, 1H), 4.65 (d, J=15.6 Hz, 1H), 4.39 (dt, J=12.7, 4.9 Hz, 1H), 4.00 (d, J 15.6 Hz, 1H), 3.02 (dd, J=17.3, 12.7 Hz, 1H), 2.75 (dd, J=17.3, 4.9 Hz, 1H)

REFERENCE EXAMPLE 15

Synthesis of Compound O

Compound O (72 mg; yield: 14%) was obtained from methyl 3-(2,3,5-trichlorophenyl)-4-nitrobutyrate (325 mg, 1.0 mmol), 3,4-dihydroxybenzaldehyde (140 mg, 1.0 mmol) and 3-aminomethylpyridine (0.20 mL, 2.0 mmol) in a manner similar to that in Reference Example 1.

$^1$H-NMR (DMSO-$d_6$, 300 MHz) δ 9.26 (br s, 1H), 8.96 (br s, 1H), 8.41 (dd, J=4.8, 1.7 Hz, 1H), 8.18 (d, J=1.7 Hz, 1H), 8.04 (d, J=2.4 Hz, 1H), 7.81 (d, J=2.4 Hz, 1H), 7.45 (d, J=7.8 Hz, 1H), 7.28 (dd, J=7.8, 4.8 Hz, 1H), 6.73 (d, J=2.4 Hz, 1H), 6.64 (d, J=8.0 Hz, 1H), 6.53 (d, J=8.0 Hz, 1H), 5.88 (dd, J=11.6, 10.0 Hz, 1H), 4.82 (d, J=10.0 Hz, 1H), 4.63 (d, J=15.5 Hz, 1H), 4.50 (m, 1H), 4.01 (d, J=15.5 Hz, 1H), 2.99 (dd, J=16.7, 13.6 Hz, 1H), 2.78 (dd, J=16.7, 5.3 Hz, 1H)

REFERENCE EXAMPLE 16

Synthesis of Compound P

Compound P (67 mg; yield: 12%) was obtained from methyl 3-(3,5-dibromophenyl)-4-nitrobutyrate (892 mg, 2.3 mmol), 3,4-dihydroxybenzaldehyde (317 mg, 2.3 mmol) and 3-aminomethylpyridine (0.47 mL, 2.0 mmol) in a manner similar to that in Reference Example 1.

$^1$H-NMR (DMSO-$d_6$, 300 MHz) δ 9.24 (br s, 1H), 8.99 (br s, 1H), 8.45 (d, J=3.5 Hz, 1H), 8.22 (br s, 1H), 7.74 (s, 2H), 7.73 (s, 1H), 7.47 (d, J=7.9 Hz, 1H), 7.31 (dd, J=7.9, 4.8 Hz, 1H), 6.71 (s, 1H), 6.68 (d, J=8.2 Hz, 1H), 6.55 (d, J=8.2 Hz, 1H ), 5.74 (dd, J=11.4, 9.8 Hz, 1H), 4.88 (d, J=15.4 Hz, 1H), 4.64 (d, J=9.8 Hz, 1H), 3.93 (m, 1H), 3.78 (d, J=15.4 Hz, 1H), 3.11 (dd, J=17.2, 12.7 Hz, 1H), 2.74 (dd, J=17.2, 4.8 Hz, 1H)

REFERENCE EXAMPLE 17

Synthesis of Compound Q

Compound Q (110 mg; yield: 24%) was obtained from methyl 3-(2-bromophenyl)-4-nitrobutyrate (105 mg, 0.50 mmol), benzaldehyde (53 mg, 1.0 mmol) and 3-aminomethylpyridine (0.11 mL, 1.0 mmol) in a manner similar to that in Reference Example 1.

$^1$H-NMR (CDCl$_3$, 300 MHz) δ 8.55 (dd, J=4.7, 1.7 Hz, 1H), 8.21 (d, J=1.8 Hz, 1H), 7.58 (dd, J=7.9, 1.2 Hz, 1H), 7.51 (dt, J=7.9, 1.8 Hz, 1H), 7.45–7.37 (m, 3H), 7.33–7.11 (m, 6H), 5.32–5.21 (m, 2H), 4.88 (d, J=9.0 Hz, 1H), 4.38 (m, 1H), 3.80 (d, J=14.9 Hz, 1H), 3.07 (dd, J=17.6, 5.2 Hz, 1H), 2.83 (m, 1H)

REFERENCE EXAMPLE 18

Synthesis of Compound R

Compound R (320 mg; yield: 63%) was obtained from methyl 3-(2-bromophenyl)-4-nitrobutyrate (301 mg, 1.0 mmol), vanillin (152 mg, 1.0 mmol) and 3-aminomethylpyridine (0.20 mL, 2.0 mmol) in a manner similar to that in Reference Example 1.

$^1$H-NMR (DMSO-$d_6$, 300 MHz) δ 9.16 (br s, 1H), 8.36 (dd, J=4.4 Hz, 1H), 8.13 (br s, 1H), 7.78 (d, J=7.5 Hz, 1H), 7.62 (d, J=8.1 Hz, 1H), 7.46 (t, J=7.5 Hz, 1H), 7.37 (d, J=8.1 Hz, 1H), 7.26–7.20 (m, 2H), 6.93 (br s, 1H), 6.68–6.61 (m, 2H), 5.93 (dd, J=10.6, 9.8 Hz, 1H), 4.98 (d, J=9.8 Hz, 1H), 4.44–4.28 (m, 3H), 3.59 (s, 3H), 2.98 (dd, J=16.9, 12.8 Hz, 1H), 2.76 (dd, J=16.9, 5.0 Hz, 1H)

REFERENCE EXAMPLE 19

Synthesis of Compound S

Compound S (1.35 g; yield: 64%) was obtained from methyl 3-(2-bromophenyl)-4-nitrobutyrate (1.2 g, 4.0 mmol), 3,4-dimethoxybenzaldehyde (664 mg, 4.0 mmol) and 3-aminomethylpyridine (0.80 mL, 8.0 mmol) in a manner similar to that in Reference Example 1.

$^1$H-NMR (CDCl$_3$, 300 MHz) δ 8.36 (d, J=4.4 Hz, 1H), 8.14 (br s, 1H), 7.77 (d, J=6.9 Hz, 1H), 7.62 (d, J=8.0 Hz, 1H), 7.46 (dd, J=7.7, 7.3 Hz, 1H), 7.36 (d, J=7.7 Hz, 1H), 7.21 (m, 2H), 6.97 (br s, 1H), 6.84–6.77 (m, 2H), 5.95 (t, J=10.8 Hz, 1H), 5.04 (d, J=10.8 Hz, 1H), 4.48–4.26 (m, 3H), 3.71 (s, 3H), 3.58 (s, 3H), 3.03 (dd, J=16.8, 12.8 Hz, 1H), 2.78 (dd, J=16.8, 5.3 Hz, 1H)

REFERENCE EXAMPLE 20

Synthesis of Compound T

Compound T (220 mg; yield: 45%) was obtained from methyl 3-(2-bromophenyl)-4-nitrobutyrate (300 mg, 1.0 mmol), 4-methoxybenzaldehyde (0.10 mL, 0.9 mmol) and 3-aminomethylpyridine (0.20 mL, 2.0 mmol) in a manner similar to that in Reference Example 1.

$^1$H-NMR (DMSO-$d_6$, 300 MHz) δ 8.38 (dd, J=4.8, 1.5 Hz, 1H) 8.11 (d, J=1.5 Hz, 1H), 7.78 (d, J=7.0 Hz, 1H), 7.61 (dd, J=8.1, 1.1 Hz, 1H), 7.44 (t, J=7.0 Hz, 1H), 7.37 (d, J=8.1 Hz, 1H), 7.29–7.20 (m, 4H), 6.83 (d, J=8.8 Hz, 2H), 5.92 (dd, J=11.5, 10.1 Hz, 1H), 5.02 (d, J=10.1 Hz, 1H), 4.48–4.35 (m, 2H), 4.21 (d, J=15.4 Hz, 1H), 3.70 (S, 3H), 3.04 (dd, J=16.8, 12.8 Hz, 1H), 2.75 (dd, J=16.8, 5.2 Hz, 1H)

REFERENCE EXAMPLE 21

Synthesis of Compound U

Compound U (192 mg; yield: 15%) was obtained from methyl 3-(2-bromophenyl)-4-nitrobutyrate (602 mg, 2.0 mmol), 3,4-bis(tert-butoxycarbonylamino)benzaldehyde (152 mg, 1.0 mmol) and 3-aminomethylpyridine (0.20 mL, 2.0 mmol) in a manner similar to that in Reference Example 1.

$^1$H-NMR (CDCl$_3$, 300 MHz) δ 8.52–8.46 (m, 2H), 7.64 (d, J=7.7 Hz, 1H), 7.58 (d, J=8.4 Hz, 1H), 7.52 (dd, J=7.9, 1.1 Hz, 1H), 7.35 (d, J=7.7 Hz, 1H), 7.30–7.20 (m, 3H), 7.08 (m, 1H), 6.67 (br s, 1H), 4.97 (dd, J=10.9, 9.5 Hz, 1H), 4.41 (d, J=14.6 Hz, 1H), 4.17 (m, 1H), 3.82 (d, J=9.5 Hz, 1H), 3.79 (d, J=14.6 Hz, 1H), 3.00 (m, 1H), 2.80 (m, 1H), 1.52 (s, 9H), 1.46 (s, 9H)

REFERENCE EXAMPLE 22

Synthesis of Compound V

Compound V (127 mg; yield: 25%) was obtained from methyl 3-(2-bromophenyl)-4-nitrobutyrate (301 mg, 1.0 mmol), 4-hydroxy-3,5-dimethylbenzaldehyde (150 mg, 1.0 mmol) and 3-aminomethylpyridine (0.20 mL, 2.0 mmol) in a manner similar to that in Reference Example 1.

$^1$H-NMR (DMSO-$d_6$, 300 MHz) δ 8.41 (s, 1H), 8.35 (d, J=4.9 Hz, 1H), 8.08 (s, 1H), 7.79 (d, J=6.9 Hz, 1H), 7.60 (d, J==8.3 Hz, 1H), 7.45–7.34 (m, 2H), 7.24–7.18 (m, 2H), 6.85 (s, 2H), 5.85 (dd, J=11.2, 9.9 Hz, 1H), 4.86 (d, J=9.9 Hz, 1H), 4.88–4.20 (m, 3H), 3.01 (dd, J=17.1, 13.2 Hz, 1H), 2.71 (dd, J=17.1, 5.3 Hz, 1H), 2.03 (s, 6H)

REFERENCE EXAMPLE 23

Synthesis of Compound W

Compound W (699 mg; yield: 36%) was obtained from methyl 3-(2-bromopenyl)-4-nitrobutyrate (0.93 g, 3 mmol), 3-iodo-4-methoxymethoxybenzaldehyde (873 mg, 3.0 mmol) and 3-aminomethylpyridine (0.611 mL, 6 mmol) in a manner similar to that in Reference Example 1.

$^1$H-NMR (CDCl$_3$, 270 MHz) δ 8.61 (br s, 1H), 8.34 (br s, 1H), 7.58 (br s, 1H), 7.42 (d, J=7.4 Hz, 1H), 7.30–7.14 (m, 7H), 5.25 (s, 2H), 5.23–5.06 (m, 2H), 4.76 (d, J=9.8 Hz, 1H), 4.15–4.04 (m, 2H), 3.52 (s, 3H), 2.97 (dd, J=17.6, 5.2 Hz, 1H), 2.82 (dd, J=17.6, 12.7 Hz, 1H)

REFERENCE EXAMPLE 24

Synthesis of Compound X

Compound X (1.7 g; yield: 60%) was obtained from methyl 3-(2-bromophenyl)-4-nitrobutyrate (1.4 g, 4.7 mmol), 3-iodo-4-hydroxybenzaldehyde (1.0 g, 4.7 mmol) and 3-aminomethylpyridine (1.01 g, 9.4 mmol) in a manner similar to that in Reference Example 1.

$^1$H-NMR (DMSO-$d_6$, 270 MHz) δ 10.44 (br s, 1H), 8.36 (dd, J=4.6, 1.6 Hz, 1H), 8.08 (d, J=1.7 Hz, 1H), 7.79–7.71 (m, 2H), 7.60 (d, J=7.9 Hz, 1H), 7.44 (m, 1H), 7.36 (m, 1H), 7.24–7.19 (m, 2H), 7.08 (dd, J=8.6, 2.0 Hz, 1H), 6.68 (d, J=8.2 Hz, 1H), 5.92 (dd, J=11.2, 10.2 Hz, 1H), 4.97 (d, J=10.2 Hz, 1H), 4.42–4.23 (m, 3H), 3.01 (dd, J=17.0, 13.2 Hz, 1H), 2.73 (dd, J=17.0, 5.3 Hz, 1H)

REFERENCE EXAMPLE 25

Synthesis of Compound Y

Methyl 3-(2-bromophenyl)-4-nitrobutyrate (903 mg, 3.0 mmol), 2-nitrobenzaldehyde (453 mg, 3.0 mmol) and 3-aminomethylpyridine (0.61 mL, 6.0 mmol) were heated under reflux in acetic acid/ethanol (1/1, 2 mL) for 5 hours. The solvent was evaporated under reduced pressure, and the residue was purified by silica gel column chromatography (eluted with chloroform/methanol=95/5) to obtain Compound Y (230 mg; yield: 15%).

$^1$H-NMR (CDCl$_3$, 270 MHz) δ 8.49 (dd, J=4.6, 1.3 Hz, 1H) 8.06 (br s, 1H), 7.94 (dd, J=5.9, 3.6 Hz, 1H), 7.58–7.55 (m, 4H), 7.33–7.12 (m, 5H), 5.75 (br s, 1H), 5.53 (m, 1H), 4.89 (d, J=14.9 Hz, 1H), 4.35 (m, 1H), 4.19 (d, J=14.9 Hz, 1H), 2.93–2.86 (m, 2H)

REFERENCE EXAMPLE 26

Synthesis of Compound Z

Compound Z (490 mg; yield: 32%) was obtained from methyl 3-(2-bromophenyl)-4-nitrobutyrate (900 mg, 3.0 mmol), 3-nitrobenzaldehyde (450 mg, 3.0 mmol) and 3-aminomethylpyridine (0.61 ml, 6.0 mmol) in a manner similar to that in Reference Example 1.

$^1$H-NMR (CDCl$_3$, 270 MHz) δ 8.49 (dd, J=4.7, 1.5 Hz, 1H), 8.22 (m, 1H), 8.14 (d, J=2.0 Hz, 1H), 8.06 (m, 1H), 7.59–7.48 (m, 3H), 7.46 (d, J=6.2 Hz, 1H), 7.32–7.21 (m, 4H), 5.39 (dd, J=10.6, 8.9 Hz, 1H), 5.11 (d, J=8.9 Hz, 1H), 4.99 (d, J=15.2 Hz, 1H), 4.46 (m, 1H), 4.10 (d, J=15.2 Hz, 1H), 3.11 (dd, J=17.8, 5.3 Hz, 1H), 2.89 (m, 1H)

REFERENCE EXAMPLE 27

Synthesis of Compound AA

Compound AA (1.4 g; yield: 82%) was obtained from methyl 3-(2-ethylphenyl)-4-nitrobutyrate (1.0 g, 4.0 mmol), 4-hydroxybenzaldehyde (488 mg, 4.0 mmol) and 3-aminomethylpyridine (0.82 mL, 8.0 mmol) in a manner similar to that in Reference Example 1.

$^1$H-NMR (DMSO-$d_6$, 270 MHz) δ 9.58 (s, 1H), 8.38 (br s, 1H), 8.11 (br s, 1H), 7.64 (d, J=7.2 Hz, 1H), 7.39 (d, J=7.9 Hz, 1H), 7.21–7.09 (m, 6H), 6.60 (d, J=6.9 Hz, 2H), 5.79 (dd, J=10.9, 9.9 Hz, 1H), 4.89 (d, J=9.9 Hz, 2H), 4.45 (d, J=14.8 Hz, 1H), 4.20–4.14 (m, 2H), 3.00 (dd, J=16.5, 12.9 Hz, 1H), 2.73–2.60 (m, 3H), 1.13 (t, J=7.2 Hz, 3H)

REFERENCE EXAMPLE 28

Synthesis of Compound AB

Compound AB (219 mg; yield: 40%) was obtained from methyl 3-(2-ethylphenyl)-4-nitrobutyrate (251 mg, 1.0 mmol), 3,5-dimethoxy-4-hydroxybenzaldehyde (182 mg, 1.0 mmol) and 3-aminomethylpyridine (0.208 mL, 2.0 mmol) in a manner similar to that in Reference Example 1.

$^1$H-NMR (DMSO-$d_6$, 270 MHz) δ 8.61 (s, 1H), 8.49 (dd, J=4.8, 1.4 Hz, 1H), 8.33 (d, J=1.7 Hz, 1H), 7.79 (d, J=6.9 Hz, 1H), 7.66 (d, J=7.9 Hz, 1H), 7.40–7.31 (m, 3H), 6.70 (s, 2H), 6.01 (dd, J=11.2, 9.9 Hz, 1H), 5.07 (d, J=9.9 Hz, 1H), 4.57 (d, J=15.5 Hz, 1H), 4.60–4.32 (m, 2H), 3.74 (s, 6H), 3.15 (dd, J=16.8, 12.6 Hz, 1H), 2.89–2.75 (m, 3H), 1.29 (t, J=7.6 Hz, 3H)

REFERENCE EXAMPLE 29

Synthesis of Compound AC

Compound AC (2.5 g; yield: 57%) was obtained from methyl 3-(2-ethylphenyl)-4-nitrobutyrate (1.8 g, 7.1 mmol), 3-iodo-4-methoxymethoxybenzaldehyde (2.1 g, 7.1 mmol) and 3-aminomethylpyridine (1.45 mL, 14.2 mmol) in a manner similar to that in Reference Example 1.

$^1$H-NMR (CDCl$_3$, 270 MHz) δ 8.55 (dd, J=4.6, 1.7 Hz, 1H) 8.25 (d, J=1.7 Hz, 1H), 7.58 (s, 1H), 7.47 (dt, J=7.9, 1.9 Hz, 1H), 7.25–7.07 (m, 6H), 7.01 (d, J=1.3 Hz, 1H), 5.25 (s, 2H), 5.19–5.06 (m, 2H), 4.79 (d, J=9.2 Hz, 1H), 4.04 (m, 1H), 3.94 (d, J=14.9 Hz, 1H), 3.52 (s, 3H), 2.97 (dd, J=17.8, 5.2 Hz, 1H), 2.82 (dd, J=17.8, 12.9 Hz, 1), 2.79–2.58 (m, 2H), 1.21 (t, J=7.6 Hz, 3H)

REFERENCE EXAMPLE 30

Synthesis of Compound AD

Methyl 3-(3-bromophenyl)-4-nitrobutyrate (302 mg, 1.0 mmol), 4-hydroxybenzaldehyde (122 mg, 1.0 mmol) and 3-aminomethylpyridine (0.20 mL, 2.0 mmol) were heated under reflux in ethanol for 20 hours. Ethanol was evaporated under reduced pressure, and the residue was purified by silica gel column chromatography (eluted with chloroform/methanol 95/5) to obtain Compound AD (293 mg; yield: 61%).

$^1$H-NMR (DMSO-$d_6$, 300 MHz) δ 9.65 (br s, 1H), 8.42 (br d, J=3.1 Hz, 1), 8.16 (br s, 1H), 7.73 (m, 1H), 7.50–7.20 (m, 5H), 7.09 (m, 2H), 6.69 (m, 2H), 5.73 (dd, J=11.1, 10.0 Hz, 1H), 4.79 (d, J=10.0 Hz, 1H), 4.70 (d, J=15.6 Hz, 1H), 3.94 (d, J=15.6 Hz, 1H), 3.94 (m, 1H), 3.14 (dd, J=17.0, 13.2 Hz, 1H), 2.75 (dd, J=17.0, 3.7 Hz, 1H)

REFERENCE EXAMPLE 31

Synthesis of Compound AE

Compound AE (75 mg; yield: 32%) was obtained from methyl 3-(2-bromophenyl)-4-nitrobutyrate (105 mg, 0.50 mmol), 3-thiophenecarboxaldehyde (0.044 mL, 0.5 mmol) and 3-aminomethylpyridine (0.102 mL, 1.0 mmol) in a manner similar to that in Reference Example 1.

$^1$H-NMR (CDCl$_3$, 300 MHz) δ 8.61 (dd, J=4.2, 1.1 Hz, 1H) 8.26 (d, J=1.1 Hz, 1H), 7.56–7.49 (m, 2H), 7.37 (m, 1H), 7.31–7.11 (m, 5H), 6.94 (d, J=4.0 Hz, 1H), 5.33 (dd, J=10.6, 9.0 Hz, 1H), 5.17–5.06 (m, 2H), 4.37 (m, 1H), 3.95 (d, J=14.8 Hz, 1H), 3.03 (dd, J=17.6, 5.2 Hz, 1H), 2.77 (m, 1H)

REFERENCE EXAMPLE 32

Synthesis of Compound AF

Compound AF (96 mg; yield: 10%) was obtained from methyl 3-(2-bromophenyl)-4-nitrobutyrate (602 mg, 2.0 mmol), 2-pyridinecarboxaldehyde (214 mg, 2.0 mmol) and 3-aminomethylpyridine (0.41 mL, 4.0 mmol) in a manner similar to that in Reference Example 1.

$^1$H-NMR (DMSO-$d_6$, 300 MHz) δ 8.63 (m, 1H), 8.50 (dd, J=4.7, 1.4 Hz, 1H), 8.23 (d, J=4.7 Hz, 1H), 7.72–7.53 (m, 3H), 7.31–7.04 (m, 6H), 5.73 (dd, J=10.7, 7.0 Hz, 1H), 5.14–5.08 (m, 2H), 4.47 (m, 1H), 3.97 (d, J=15.2 Hz, 1H), 3.02–2.60 (m, 2H)

REFERENCE EXAMPLE 33

Synthesis of Compound AG

Compound AG (167 mg; yield: 15%) was obtained from methyl 3-(3-thienyl)-4-nitrobutyrate (590 mg, 2.6 mmol), 3,4-dihydroxybenzaldehyde (360 mg, 2.6 mmol), and 3-aminomethylpyridine (5.1 ml, 5.2 mmol) in a manner similar to that in Reference Example 1.

$^1$H-NMR (DMSO-$d_6$, 300 MHz) δ 9.23 (br s, 1H), 9.00 (br s, 1H), 8.45 (dd, J=3.1, 1.5 Hz, 1H), 8.20 (d, J=1.5 Hz, 1H), 7.50–7.47 (m, 2H), 7.40 (m, 1H), 7.32 (dd, J=7.8, 5.0 Hz, 1H), 7.20 (d, J=7.8 Hz, 1H), 6.49 (s, 1H), 6.48 (d, J=7.4 Hz, 1H), 6.47 (dd, J=7.4, 2.0 Hz, 1H), 5.52 (dd, J=11.5, 9.9 Hz, 1H), 4.88 (d, J=15.4 Hz, 1H), 4.65 (d, J=9.9 Hz, 1H), 4.00 (m, 1H), 3.77 (d, J=15.4 Hz, 1H), 3.19 (dd, J=17.1, 12.1 Hz, 1H), 2.91 (dd, J=17.1, 4.5 Hz, 1H)

REFERENCE EXAMPLE 34

Synthesis of Compound AH

Compound AH (49 mg; yield: 12%) was obtained from methyl 3-(3-chlorophenyl)-4-nitrobutyrate (260 mg, 1.0 mmol), 3-pyridinecarboxaldehyde (0.10 mL, 1.0 mmol), and 3-aminomethylpyridine (0.20 mL, 2.0 mmol) in a manner similar to that in Reference Example 1.

$^1$H-NMR (DMSO-$d_6$, 300 MHz) δ 8.51–8.48 (m, 2H), 8.39 (dd, J=4.9, 1.3 Hz, 1H), 8.11 (d, J=1.9 Hz, 1H), 7.79 (td, J=8.1, 1.9 Hz, 1H), 7.38 (s, 1H), 7.38–7.22 (m, 6H), 5.88 (dd, J=11.2, 9.9 Hz, 1H), 5.09 (d, J=9.9 Hz, 1H), 4.48 (d, J=16.0 Hz, 1H), 4.27 (d, J=16.0 Hz, 1H), 4.04 (dt, J=12.3, 4.9 Hz, 1H), 3.22 (dd, J=17.0, 12.3 Hz, 1H), 2.80 (dd, J=17.0, 4.9 Hz, 1H)

REFERENCE EXAMPLE 35

Synthesis of Compound AI

Compound AI (120 mg; yield: 23%) was obtained from methyl 3-(2-bromophenyl)-4-nitrobutyrate (301 mg, 1.0 mmol), 5-formyl-2-thiophenecarboxylic acid (155 mg, 1.0 mmol) and 3-aminomethylpyridine (0.20 mL, 2.0 mmol) in a manner similar to that in Reference Example 1.

$^1$H-NMR (DMSO-$d_6$, 270 MHz) δ 8.41 (d, J=3.3 Hz, 1H), 8.27 (br s, 1H), 7.81 (d, J=7.2 Hz, 1H), 7.62 (d, J=6.9 Hz, 1H), 7.51 (d, J=7.6 Hz, 1H), 7.45 (m, 1H), 7.31–7.20 (m, 2H), 7.07 (m, 1H), 6.98 (m, 1H), 5.94 (dd, J=10.5, 9.6 Hz, 1H), 5.35 (d, J=9.6 Hz, 1H), 4.64 (d, J=15.6 Hz, 1H), 4.39 (m, 1H), 4.27 (d, J=15.6 Hz, 1H), 3.03 (dd, J=16.5, 13.0 Hz, 1H), 2.72 (dd, J=16.5, 6.3 Hz, 1H)

REFERENCE EXAMPLE 36

Synthesis of Compound AJ

Compound AJ (23 mg; yield: 2.5%) was obtained from methyl 3-(2-bromophenyl)-4-nitrobutyrate (602 mg, 2.0 mmol), 2-imidazolecarboxaldehyde (192 mg, 2.0 mmol) and 3-aminomethylpyridine (0.41 mL, 4.0 mmol) in a manner similar to that in Reference Example 1.

$^1$H-NMR (DMSO-$d_6$, 300 MHz) δ 11.43 (m, 1H), 8.49 (d, J=3.7 Hz, 1H), 8.34 (s, 1H), 7.62–7.54 (m, 2H), 7.33–7.14 (m, 6H), 5.78 (dd, J=10.4, 6.8 Hz, 1H), 5.26 (d, J=6.8 Hz, 1H), 5.09 (d, J=15.1 Hz, 1H), 4.42 (m, 1H), 4.15 (d, J=15.1 Hz, 1H), 2.94–2.84 (m, 2H)

REFERENCE EXAMPLE 37

Synthesis of Compound AK

Compound AK (62 mg; yield: 6.1%) was obtained from methyl 3-(2-bromophenyl)-4-nitrobutyrate (602 mg, 2.0 mmol), indole-3-carboxaldehyde (290 mg, 2.0 mmol) and 3-aminomethylpyridine (0.41 mL, 4.0 mmol) in a manner similar to that in Reference Example 1.

$^1$H-NMR (DMSO-$d_6$, 300 MHz) δ 9.49 (br s, 1H), 8.47 (d, J=3.7 Hz, 1H), 8.10 (br s, 1H), 7.65–7.45 (m, 3H), 7.38–7.09 (m, 7H), 6.97 (br s, 1H), 5.63 (m, 1H), 5.23 (d, J=14.9 Hz, 1H), 5.16 (d, J=9.6 Hz, 1H), 4.41 (m, 1H), 3.99 (d, J==14.9 Hz, 1H), 3.14 (dd, J=15.6, 5.1 Hz, 1H), 2.81 (m, 1H)

REFERENCE EXAMPLE 38

Synthesis of Compound AL

Compound AL (73 mg; yield: 7.8%) was obtained from methyl 3-(2-bromophenyl)-4-nitrobutyrate (602 mg, 2.0 mmol), 4-pyridinecarboxaldehyde (210 mg, 2.0 mmol) and 3-aminomethylpyridine (0.41 mL, 4.0 mmol) in a manner similar to that in Reference Example 1.

$^1$H-NMR (DMSO-$d_6$, 300 MHz) δ 8.52 (d, J=2.0 Hz, 1H), 8.46 (dd, J=4.7, 1.5 Hz, 1H), 8.35 (dd, J=4.7, 1.1 Hz, 1H), 8.06 (d, J=2.0 Hz, 1H), 7.85–7.75 (m, 2H), 7.62 (d, J=8.0

Hz, 1H), 7.47–7.15 (m, 5H), 6.04 (dd, J=11.6, 9.9 Hz, 1H), 5.24 (d, J=9.9 Hz, 1H), 4.54–4.38 (m, 2H), 4.27 (d, J=15.7 Hz, 1H), 3.06 (d, J=17.1, 13.0 Hz, 1H), 2.79 (dd, J=17.1, 5.1 Hz, 1H)

REFERENCE EXAMPLE 39

Synthesis of Compound AM

Compound AM (31 mg; yield: 3.4%) was obtained from methyl 3-(2-bromophenyl)-4-nitrobutyrate (602 mg, 2.0 mmol), 4-imidazolecarboxaldehyde (192 mg, 2.0 mmol) and 3-aminomethylpyridine (0.41 mL, 4.0 mmol) in a manner similar to that in Reference Example 1.

$^1$H-NMR (DMSO-$d_6$, 300 MHz) δ 12.10 (br s, 1H), 8.39 (dd, J=4.7, 1.5 Hz, 1H), 8.25 (d, J=1.5 Hz, 1H), 7.74 (d, J=7.4 Hz, 1H), 7.63–7.60 (m, 2H), 7.52 (d, J=7.8 Hz, 1H), 7.42 (t, J=7.4 Hz, 1H), 7.29–7.17 (m, 3H), 5.93 (dd, J=11.6, 8.6 Hz, 1H), 5.14 (d, J=8.6 Hz, 1H), 4.64 (d, J=15.4 Hz, 1H), 4.36 (m, 1H), 4.22 (d, J=15.4 Hz, 1H), 3.01 (dd, J=16.9, 13.1 Hz, 1H), 2.67 (dd, J=16.9, 5.1 Hz, 1H)

REFERENCE EXAMPLE 40

Synthesis of Compound AN

Compound AN (258 mg; yield: 51%) was obtained from methyl 3-(2-bromophenyl)-4-nitrobutyrate (301 mg, 1.0 mmol), piperonal (150 mg, 1.0 mmol) and 3-aminomethylpyridine (0.21 mg, 2.0 mmol) in a manner similar to that in Reference Example 1.

$^1$H-NMR (CDCl$_3$, 300 MHz) δ 8.56 (dd, J=5.0, 1.6 Hz, 1H) 8.26 (d, J=1.8 Hz, 1H), 7.59–7.52 (m, 2H), 7.34–7.12 (m, 6H), 6.77 (d, J=7.9 Hz, 1H), 6.65 (d, J=1.7 Hz, 1H), 6.57 (dd, J=7.9, 1.9 Hz, 1H), 6.03 (d, J=1.3 Hz, 1H), 5.24–5.19 (m, 2H), 4.79 (d, J=9.2 Hz, 1H), 4.33 (m, 1H) 3.85 (d, J=14.9 Hz, 1H), 3.06 (dd, J=17.6, 5.0 Hz, 1H), 2.80 (m, 1H), 1.91 (d, J=1.2 Hz, 3H), 1.56 (d, J=1.2 Hz, 3H)

REFERENCE EXAMPLE 41

Synthesis of Compound AO

An N-trityl derivative of Compound AO was obtained from methyl 3-(2-bromophenyl)-4-nitrobutyrate (124 mg, 0.4 mmol), N-trityl-5-benzimidazolecarboxaldehyde (192 mg, 2.0 mmol) and 3-aminomethylpyridine (0.082 mL, 0.8 mmol) in a manner similar to that in Reference Example 1. To a methanol solution (10 mL) of the resulting N-trityl derivative was added trifluoroacetic acid (0.5 mL), and the mixture was stirred at room temperature for 3 hours. The solvent was evaporated under reduced pressure, and the residue was purified by silica gel thin layer chromatography (developed with chloroform/methanol=9/1) to obtain Compound AO (32 mg; yield: 16%).

$^1$H-NMR (CDCl$_3$, 300 MHz) δ 8.48 (dd, J=4.8, 1.4 Hz, 1H) 8.09 (br s, 2H), 7.59–7.50 (m, 4H), 7.27–7.25 (m, 4H), 7.15–7.08 (m, 2H), 5.44 (m, 1H), 5.13 (d, J=14.9 Hz, 1H), 5.03 (d, J=5.1 Hz, 1H), 4.23 (m, 1H), 3.75 (d, J=14.9 Hz, 1H), 3.09 (dd, J=17.6, 5.1 Hz, 1H), 2.86 (m, 1H)

REFERENCE EXAMPLE 42

Synthesis of Compound AP and Compound AQ
Step 1
Sodium methylate (4.05 g, 21 mmol) was added to a methanol solution (20 mL) of 2,5-dibromopyridine (1 g, 4.2 mmol), followed by refluxing for 13 hours. The reaction solution was poured into dilute hydrochloric acid for neutralization and the mixture was extracted with a chloroform/methanol mixed solvent (chloroform/methanol=9/1). The extract was washed with a saturated aqueous solution of sodium chloride and dried over sodium sulfate. The solvent was evaporated under reduced pressure, and the resulting residue was purified by silica gel column chromatography (eluted with chloroform/methanol=99/1) to obtain 2-methoxy-5-bromopyridine (660 mg; yield: 87%).

$^1$H-NMR (CDCl$_3$, 300 MHz) δ 8.20 (d, J=2.6 Hz, 1H), 7.61 (ddd, J=8.7, 2.6, 0.5 Hz, 1H), 6.64 (d, J=8.7 Hz, 1H), 3.91 (s, 3H)
Step 2
To a DMF solution (10 mL) of the 2-methoxy-5-bromopyridine obtained in step 1 was added n-butyl lithium (1.4 mol/l in hexane, 7 mL). The temperature was slowly elevated to room temperature, and the mixture was stirred at that temperature for 3 hours. The reaction solution was poured into dilute hydrochloric acid for neutralization and the mixture was extracted with a chloroform-methanol mixed solvent (chloroform/methanol=9/1). The extract was washed with a saturated aqueous sodium chloride solution and dried over sodium sulfate. The solvent was evaporated under reduced pressure. The resulting residue was purified by silica gel column chromatography (eluted with chloroform) to obtain a mixture of 3-(6-methoxypyridyl) carboxaldehyde and 3-(2-methoxypyridyl)carboxaldehyde [3-(6-methoxypyridyl)carboxaldehyde:3-(2-methoxypyridyl)carboxaldehyde=4:1, 720 mg; yield: >95%].

FAB-MS (m/z): 138 (M+1)
Step 3
A crude piperidone product having a methoxypyridyl group (370 mg; yield: 37%) was obtained from the mixture of 3-(6-methoxypyridyl)carboxaldehyde and 3-(2-methoxypyridyl)carboxaldehyde (4/1, 274 mg, 2.0 mmol), methyl 3-(2-bromophenyl)-4-nitrobutyrate (602 mg, 2.0 mmol) and 3-aminomethylpyridine (0.407 mL, 4.0 mmol) in a manner similar to that in Reference Example 1.

FAB-MS (m/z): 499, 497 (M+1)
Step 4
The above crude piperidone product (120 mg, 0.24 mmol) was dissolved in a 60% acetic acid solution of hydrogen bromide, and the solution was stirred at 90° C. for 3 hours. The solvent was evaporated under reduced pressure, and the residue was diluted with chloroform/methanol (9/1), the mixture was neutralized with an aqueous sodium hydroxide solution (1 mol/l) and extracted with chloroform. The extract was washed with a saturated aqueous sodium chloride solution, and dried over sodium sulfate. The solvent was evaporated under reduced pressure, and the residue was purified by silica gel thin layer chromatography (developed with chloroform/methanol, 9/1) to obtain desired demethylated compounds, i.e., Compound AP (7.6 mg; yield: 6.2%) and Compound AQ (28 mg; yield: 23%).
Compound AP:

$^1$H-NMR (CDCl$_3$, 300 MHz) δ 12.4 (br s, 1H), 8.46 (d, J=4.8 Hz, 1H), 8.30 (br s, 1H), 7.64–7.56 (m, 2H), 7.36–7.13 (m, 6H), 6.26 (t, J=6.6 Hz, 1H), 5.85 (m, 1H), 4.89 (d, J=7.5 Hz, 1H), 4.80 (d, J=15.3 Hz, 1H), 4.44–4.39 (m, 2H), 2.95–2.90 (m, 2H)
Compound AQ:

$^1$H-NMR (CDCl$_3$, 300 MHz) δ 12.8 (br s, 1H), 8.51 (d, J=3.5 Hz, 1H), 8.34 (br s, 1H), 7.58–7.51 (m, 2H), 7.31–7.12 (m, 6H), 6.53 (d, J=9.5 Hz, 1H), 5.32 (m, 1H), 5.01 (d, J=15.2 Hz, 1H), 4.73 (d, J=9.3 Hz, 1H), 4.37 (m, 1H), 4.17 (d, J=15.2 Hz, 1H), 3.06 (dd, J=17.6, 15.1 Hz, 1H), 2.82 (m, 1H)

REFERENCE EXAMPLE 43

Synthesis of Compound AR

Compound AR (7.9 mg; yield: 35%) was obtained from methyl 3-(2-bromophenyl)-4-nitrobutyrate (15 mg, 0.05 mmol), 2-thiophenecarboxaldehyde (4.6 mg, 0.05 mmol) and 3-aminomethylpyridine (0.010 mL, 0.1 mmol) in a manner similar to that in Reference Example 1.

$^1$H-NMR (CDCl$_3$, 300 MHz) δ 8.55 (dd, J=4.8, 1.3 Hz, 1H) 8.32 (d, J=1.9 Hz, 1H), 7.56 (dd, J=7.9, 1.0 Hz, 2H), 7.41 (dd, J=5.2, 0.8 Hz, 1H), 7.33–7.12 (m, 3H), 6.98 (d, J=8.5 Hz, 1H), 6.96 (d, J=3.6 Hz, 1H), 6.91 (dd, J=3.0, 1.0 Hz, 1H), 5.36 (dd, J=10.6, 9.3 Hz, 1H), 5.27–5.22 (m, 2H), 4.36 (m, 1H), 3.98 (d, J=15.2 Hz, 1H), 3.04 (dd, J=17.5, 5.3 Hz, 1H), 2.82 (m, 1H)

REFERENCE EXAMPLE 44

Synthesis of Compound AS

Compound AS (190 mg; yield: 41%) was obtained from methyl 3-(2-bromophenyl)-4-nitrobutyrate (301 mg, 1.0 mmol), 3-pyridinecarboxaldehyde (100 mg, 1.0 mmol) and 3-aminomethylpyridine (0.2 mL, 2.0 mmol) in a manner similar to that in Reference Example 1.

$^1$H-NMR (CDCl$_3$, 300 MHz) δ 8.67 (dd, J=4.8, 1.4 Hz, 1H) 8.55 (dd, J=4.6, 1.6 Hz, 1H), 8.45 (d, J=2.3 Hz, 1H), 8.21 (d, J=2.0 Hz, 1H), 7.58 (dd, J=7.9, 1.3 Hz, 1H), 7.48–7.44 (m, 2H), 7.32–7.13 (m, 5H), 5.29 (dd, J=10.2, 9.4 Hz, 1H), 5.17 (d, J=15.0 Hz, 1H), 4.97 (d, J=9.4 Hz, 1H), 4.38 (m, 1H), 3.90 (d, J=15.0 Hz, 1H), 3.10 (dd, J=17.6, 5.0 Hz, 1H), 2.85 (m, 1H)

REFERENCE EXAMPLE 45

Synthesis of Compound AT

Compound AT (1.4 g; yield: 61%) was obtained from methyl 3-(2-chlorophenyl)-4-nitrobutyrate (1.4 g, 5.4 mmol), 3-thiophenecarboxaldehyde (560 mg, 5.4 mmol) and 3-aminomethylpyridine (1.1 mL, 11 mmol) in a manner similar to that in Reference Example 1.

$^1$H-NMR (CDCl$_3$, 300 MHz) δ 8.55 (dd, J=5.0, 1.7 Hz, 1H), 8.27 (d, J=2.0 Hz, 1H), 7.55 (d, J=1.7 Hz, 1H), 7.53–7.35 (m, 2H), 7.29–7.19 (m, 4H), 7.13 (dd, J=2.7, 1.3 Hz, 1H), 6.95 (dd, J=4.6, 1.3 Hz, 1H), 5.33 (dd, J=11.2, 8.8 Hz, 1H), 5.19 (d, J=14.9 Hz, 1H), 5.06 (d, J=8.8 Hz, 1H), 4.33 (m, 1H), 3.92 (d, J=14.9 Hz, 1H), 3.03 (dd, J=17.5, 5.5 Hz, 1H), 2.87 (dd, J=17.5, 12.9 Hz, 1H)

REFERENCE EXAMPLE 46

Synthesis of Compound AU

Compound AU (98 mg; yield: 43%) was obtained from methyl 3-(2-bromophenyl)-4-nitrobutyrate (105 mg, 0.50 mmol), furfural (0.041 mL, 0.5 mmol) and 3-aminomethylpyridine (0.102 mL, 1.0 mmol) in a manner similar to that in Reference Example 1.

$^1$H-NMR (CDCl$_3$, 300 MHz) δ 8.53 (d, J=3.7 Hz, 1H), 8.32 (br s, 1H), 7.59–7.56 (m, 2H), 7.38–7.16 (m, 5H), 7.16 (m, 1H), 6.34–6.30 (m, 2H), 5.52 (dd, J=10.6, 8.6 Hz, 1H), 5.08–4.98 (m, 2H), 4.41 (m, 1H), 4.10 (d, J=15.2 Hz, 1H), 3.01 (dd, J=17.6, 5.1 Hz, 1H), 2.80 (m, 1H)

REFERENCE EXAMPLE 47

Synthesis Example AV

Compound AV (30 mg; yield: 6.2%) was obtained from methyl 3-[2-(5-bromothienyl)]-4-nitrobutyrate (307 mg, 1.0 mmol), 4-hydroxybenzaldehyde (122 mg, 1.0 mmol) and 3-aminomethylpyridine (0.20 mL, 2.0 mmol) in a manner similar to that in Reference Example 1.

$^1$H-NMR (DMSO-d$_6$, 300 MHz) δ 9.66 (br s, 1H), 8.41 (dd, J=5.0, 1.5 Hz, 1H), 8.14 (d, J=1.9, 1H), 7.43 (d, J=7.9 Hz, 1H), 7.27 (dd, J=7.6, 4.8 Hz, 1H), 7.11–7.05 (m, 3H), 6.90 (d, J=4.0 Hz, 1H), 6.67 (d, J=8.6 Hz, 2H), 5.58 (dd, J=11.2, 9.9 Hz, 1H), 4.77 (d, J=9.9 Hz, 1H), 4.69 (d, J=15.6 Hz, 1H), 4.27 (m, 1H), 3.89 (d, J=15.6 Hz, 1H), 3.17 (dd, J=16.8, 12.9 Hz, 1H), 2.85 (dd, J=16.8, 4.9 Hz, 1H)

REFERENCE EXAMPLE 48

Synthesis of Compound AW

Compound AW (403 mg; yield: 84%) was obtained from methyl 3-[2-(5-bromothienyl)]-4-nitrobutyrate (307 mg, 1.0 mmol), 3-thiophenecarboxaldehyde (113 mg, 1.0 mmol) and 3-aminomethylpyridine (0.20 mL, 2.0 mmol) in a manner similar to that in Reference Example 1.

$^1$H-NMR (CDCl$_3$, 300 MHz) δ 8.55 (dd, J=4.8, 1.3 Hz, 1H) 8.26 (s, 1H), 7.50 (d, J=7.9 Hz, 1H), 7.42 (dd, J=4.9, 2.9 Hz, 1H), 7.27 (m, 1H), 7.13–6.88 (m, 2H), 6.64 (d, J=4.0 Hz, 2H), 5.23 (d, J=14.8 Hz, 1H), 5.00–4.86 (m, 2H), 3.97 (m, 1H), 3.81 (d, J=14.8 Hz, 1H), 3.11 (dd, J=17.5, 4.9 Hz, 1H), 2.85 (dd, J=17.5, 13.2 Hz, 1H)

REFERENCE EXAMPLE 49

Synthesis of Compound AX

Compound AX (950 mg; yield: 56%) was obtained from methyl 3-(2-ethylphenyl)-4-nitrobutyrate (1.0 g, 4.0 mmol), 3-thiophenecarboxaldehyde (0.704 mL, 4.0 mmol) and 3-aminomethylpyridine (0.815 mL, 8.0 mmol) in a manner similar to that in Reference Example 1.

$^1$H-NMR (CDCl$_3$, 300 MHz) δ 8.54 (dd, J=4.8, 1.6 Hz, 1H), 8.28 (d, J=1.6 Hz, 1H), 7.50 (dt, J=8.2, 2.0 Hz, 1H), 7.41 (dd, J=5.0, 2.8 Hz, 1H), 7.28–7.12 (m, 7H), 5.22–5.12 (m, 2H), 5.03 (d, J=9.1 Hz, 1H), 4.08 (m, 1H), 3.96 (d, J=14.8 Hz, 1H), 2.95 (dd, J=17.6, 5.4 Hz, 1H), 2.85–2.61 (m, 3H), 1.21 (t, J=7.8 Hz, 3H)

REFERENCE EXAMPLE 50

Synthesis of Compound AY

Compound AY (1.3 g; yield: 63%) was obtained from methyl 3-[2-(3-methylthienyl)]-4-nitrobutyrate (1.2 g, 5.0 mmol), 3-thiophenecarboxaldehyde (438 mg, 5.0 mmol) and 3-aminomethylpyridine (1.02 mL, 10 mmol) in a manner similar to that in Reference Example 1.

$^1$H-NMR (DMSO-d$_6$, 300 MHz) δ 8.36 (dd, J=4.7, 1.6 Hz, 1H) 8.17 (d, J=2.1 Hz, 1H), 7.50 (m, 1H), 7.44–7.37 (m, 2H), 7.24–7.19 (m, 3H), 6.77 (d, J=5.1 Hz, 1H), 5.55 (dd, J=11.4, 10.0 Hz, 1H), 5.16 (d, J=10.0 Hz, 1H), 4.49 (d, J=15.7 Hz, 1H), 4.43 (m, 1H), 4.19 (d, J=15.7 Hz, 1H), 3.07 (dd, J=16.8, 12.7 Hz, 1H), 2.78 (dd, J=16.8, 5.0 Hz, 1H), 2.10 (s, 3H)

REFERENCE EXAMPLE 51

Synthesis of Compound AZ

Compound AZ (560 mg; yield: 66%) was obtained from methyl 3-[2-(3-methylthienyl)]-4-nitrobutyrate (500 mg, 1.0 mmol), 4-hydroxybenzaldehyde (122 mg, 1.0 mmol) and 3-aminomethylpyridine (0.20 mL, 2.0 mmol) in a manner similar to that in Reference Example 1.

$^1$H-NMR (DMSO-d$_6$, 300 MHz) δ 9.62 (br s, 1H), 8.38 (dd, J=4.8, 1.3 Hz, 1H), 8.14 (d, J=2.0 Hz, 1H), 7.43 (d, J=7.7 Hz, 1H), 7.37 (d, J=5.1 Hz, 1H), 7.24 (dd, J=7.7, 4.8 Hz, 1H), 7.10 (d, J=8.6 Hz, 2H), 6.62 (d, J=8.6 Hz, 2H), 5.45 (dd, J=11.2, 10.2 Hz, 1H), 4.84 (d, J=10.2 Hz, 1H), 4.59 (d, J=15.7 Hz, 1H), 4.39 (m, 1H), 4.00 (d, J=15.7 Hz, 1H), 3.11 (dd, J=16.5, 12.9 Hz, 1H), 2.78 (dd, J=16.5, 5.2 Hz, 1H), 2.11 (s, 3H)

REFERENCE EXAMPLE 52

Synthesis of Compound BA

Compound BA (500 mg; yield: 52%) was obtained from methyl 3-[2-(3-bromothienyl)]-4-nitrobutyrate (614 mg, 2.0 mmol), 3-thiophenecarboxaldehyde (226 mg, 2.0 mmol), and 3-aminomethylpyridine (0.40 mL, 4.0 mmol) in a manner similar to that in Reference Example 1.

$^1$H-NMR (DMSO-d$_6$, 300 MHz) δ 8.35 (dd, J=4.8, 1.6 Hz, 1H) 8.15 (d, J=1.8 Hz, 1H), 7.67 (d, J=5.3 Hz, 1H), 7.52 (m, 1H), 7.42–7.36 (m, 2H), 7.23–7.17 (m, 2H), 7.01 (d, J=5.3 Hz, 1H), 5.71 (dd, J=11.2, 9.7 Hz, 1H), 5.23 (d, J=9.7 Hz, 1H), 4.45–4.26 (m, 3H), 3.11 (dd, J=16.7, 12.7 Hz, 1H), 2.81 (dd, J=16.7, 5.7 Hz, 1H)

REFERENCE EXAMPLE 53

Synthesis of Compound BB

Compound BB (48 mg; yield: 32%) was obtained from methyl 3-[2-(N-methylpyrrolyl)]-4-nitrobutyrate (90 mg, 1.0 mmol), 3-thiophenecarboxaldehyde (42 mg, 0.375 mol), and 3-aminomethylpyridine (0.076 mL, 0.75 mmol) in a manner similar to that in Reference Example 1.

$^1$H-NMR (CDCl$_3$, 300 MHz) δ 8.53 (dd, J=4.8, 1.4 Hz, 1H) 8.30 (d, J=2.0 Hz, 1H), 7.51 (d, J=7.9 Hz, 1H), 7.25 (dd, J=6.5, 4.1 Hz, 1H), 7.09 (dd, J=2.9, 1.3 Hz, 1H), 6.92 (dd, J=5.0, 1.3 Hz, 1H), 6.49 (m, 1H), 6.07–6.01 (m, 3H), 5.19 (d, J=14.8 Hz, 1H), 5.01–4.85 (m, 2H), 3.89–3.77 (m, 2H), 3.52 (s, 3H), 2.98 (dd, J=17.6, 4.9 Hz, 1H), 2.78 (dd, J=17.6, 12.5 Hz, 1H)

REFERENCE EXAMPLE 54

Synthesis of Compound BC and Compound BD

Compound BD (191 mg; yield: 28%) and a Compound BC/Compound BD mixture (100 mg) were obtained from methyl 3-benzyl-4-nitrobutyrate (400 mg, 1.69 mmol), 4-hydroxybenzaldehyde (206 mg, 1.69 mmol) and 3-aminomethylpyridine (0.34 mL, 3.38 mmol) in a manner similar to that in Reference Example 1.
Compound BD:

$^1$H-NMR (DMSO-d$_6$, 300 MHz) δ 8.38 (dd, J=4.6, 1.3 Hz, 1H) 8.07 (d, J=2.0 Hz, 1H), 7.40–7.15 (m, 8H), 7.00 (d, J=8.6 Hz, 2H), 6.68 (d, J=8.6 Hz, 2H), 5.25 (dd, J=10.6, 9.8 Hz, 1H) 4.74 (d, J=9.2 Hz, 1H), 4.66 (d, J=15.5 Hz, 1H), 3.83 (d, J=15.5 Hz, 1H), 2.88 (m, 1H), 2.63–2.44 (m, 3H), 2.24 (dd, J=17.1, 4.9 Hz, 1H)

REFERENCE EXAMPLE 55

Synthesis of Compound BE

Compound BE (66 mg; yield: 29%) was obtained from methyl 3-(2-bromophenyl)-4-nitrobutyrate (105 mg, 0.50 mmol), 3-furylaldehyde (0.043 mL, 0.5 mmol) and 3-aminomethylpyridine (0.102 mL, 1.0 mmol) in a manner similar to that in Reference Example 1.

$^1$H-NMR (CDCl$_3$, 300 MHz) δ 8.56 (d, J=3.8 Hz, 1H), 8.35 (br s, 1H), 7.59–7.56 (m, 2H), 7.47 (s, 1H), 7.35–7.27 (m, 4H), 7.17 (m, 1H), 6.32 (s, 1H), 5.52–5.11 (m, 2H), 4.95 (d, J=8.8 Hz, 1H), 4.36 (m, 1H), 4.04 (d, J=15.1 Hz, 1H), 3.05 (dd, J=17.6, 5.3 Hz, 1H), 2.78 (m, 1H)

REFERENCE EXAMPLE 56

Synthesis of Compound BF

Compound BF (100 mg; yield: 30%) was obtained from methyl 3-(2-ethylphenyl)-4-nitrobutyrate (200 mg, 0.8 mmol), 2-pyridinecarboxaldehyde (107 mg, 1.0 mmol) and 3-aminomethylpyridine (0.152 mL, 1.5 mmol) in a manner similar to that in Reference Example 1.

REFERENCE EXAMPLE 57

Synthesis of Compound BG

Compound BG (80 mg; yield: 15%) was obtained from methyl 3-(a-methylbenzyl)-4-nitrobutyrate (300 mg, 1.2 mmol), 4-hydroxybenzaldehyde (0.146 mL, 1.2 mmol) and 3-aminomethylpyridine (0.21 mL, 2.4 mmol) in a manner similar to that in Reference Example 1.

$^1$H-NMR (DMSO-d$_6$, 300 MHz) δ 9.61 (s, 1H), 8.35 (dd, J=4.7, 1.7 Hz, 1H), 8.07 (d, J=1.7 Hz, 1H), 7.36–7.14 (m, 7H), 7.04 (d, J=8.5 Hz, 2H), 6.66 (d, J=8.5 Hz, 1H), 5.23 (dd, J=9.7, 8.9 Hz, 1H), 4.78 (d, J=8.9 Hz, 1H), 4.59 (d, J=15.4 Hz, 1H), 3.89 (d, J=15.4 Hz, 1H), 2.85–2.61 (m, 3H), 2.15 (dd, J=16.4, 4.5 Hz, 1H), 1.22 (d, J=7.1 Hz, 3H)

REFERENCE EXAMPLE 58

Synthesis of Compound BH

Compound BH (350 mg; yield: 42%) was obtained from methyl 3-(2-ethylphenyl)-4-nitrobutyrate (500 mg, 2.0 mmol), 4-pyrazolecarboxaldehyde (192 mg, 2.0 mmol), and 3-aminomethylpyridine (0.21 mL, 2.4 mmol) in a manner similar to that in Reference Example 1.

$^1$H-NMR (DMSO-d$_6$, 300 MHz) δ 12.86 (br s, 1H), 8.37 (dd, J=4.8, 1.6 Hz, 1H), 8.21 (d, J=1.6 Hz, 1H), 7.63–7.61 (m, 2H), 7.48 (d, J=7.6 Hz, 1H), 7.27–7.16 (m, 4H), 6.40 (s, 1H), 5.90 (dd, J=11.4, 9.9 Hz, 1H), 5.20 (d, J=9.2 Hz, 1H), 4.51 (d, J=14.5 Hz, 1H), 4.30–4.19 (m, 2H), 2.94 (dd, J=16.8, 12.9 Hz, 1H), 2.75–2.57 (m, 3H), 1.13 (t, J=7.6 Hz, 3H)

REFERENCE EXAMPLE 59

Synthesis of Compound BI

Compound BI (120 mg; yield: 15%) was obtained from methyl 3-(2-ethylphenyl)-4-nitrobutyrate (500 mg, 2.0 mmol), 4-methyl-5-imidazolecarboxaldehyde (220 mg, 2.0 mmol) and 3-aminomethylpyridine (0.41 mL, 4.0 mmol) in a manner similar to that in Reference Example 1.

$^1$H-NMR (CDCl$_3$, 300 MHz) δ 10.6 (br s, 1H), 8.48 (dd, J=4.8, 1.5 Hz, 1H), 7.95 (d, J=1.3 Hz, 1H), 7.72 (d, J=7.9 Hz, 1H), 7.48 (s, 1H), 7.35–7.31 (m, 2H), 7.25–7.16 (m, 3H), 5.61 (dd, J=11.5, 9.6 Hz, 1H), 5.06 (d, J=15.2 Hz, 1H), 4.90 (d, J=9.6 Hz, 1H), 4.17–4.07 (m, 2H), 3.00–2.81 (m, 2H), 2.79–2.57 (m, 2H), 1.82 (s, 3H), 1.23 (t, J=7.6 Hz, 3H)

REFERENCE EXAMPLE 60

Synthesis of Compound BJ

Compound BJ (34 mg; yield: 32%) was obtained from methyl 3-(2-ethylphenyl)-4-nitrobutyrate (250 mg, 1.0 mmol), 4-(1,2,3-thiadiazole)carboxaldehyde (0.114 mg, 1.0 mmol), and 3-aminomethylpyridine (0.05 mL, 0.5 mmol) in a manner similar to that in Reference Example 1.

$^1$H-NMR (CDCl$_3$, 300 MHz) δ 8.62 (d, J=4.3 Hz, 1H), 8.36–8.32 (m, 2H), 7.62 (d, J=7.3 Hz, 1H), 7.36–7.31 (m, 5H), 5.71 (dd, J=10.2, 7.2 Hz, 1H), 5.65 (d, J=7.2 Hz, 1H), 5.13 (d, J=15.5 Hz, 1H), 4.32–4.26 (m, 2H), 3.10–3.02 (m, 2H), 2.84–2.75 (m, 2H), 1.33 (t, J=7.4 Hz, 3H)

REFERENCE EXAMPLE 61

Synthesis of Compound BK

Compound BK (410 mg; yield: 48%) was obtained from methyl 3-(2-ethylphenyl)-4-nitrobutyrate (500 mg, 2.0 mmol), 1-methyl-2-imidazolecarboxaldehyde (0.1 mL, 2.0 mmol) and 3-aminomethylpyridine (0.4 mL, 4.0 mmol) in a manner similar to that in Reference Example 1.

$^1$H-NMR (CDCl$_3$, 300 MHz) δ 8.64 (dd, J=4.8, 1.4 Hz, 1H) 8.16 (d, J=2.0 Hz, 1H), 7.46 (d, J=7.6 Hz, 1H), 7.31–7.10 (m, 7H), 5.59 (dd, J=11.3, 8.7 Hz, 1H), 5.28 (d, J=15.4 Hz, 1H), 5.10 (d, J=8.9 Hz, 1H), 4.08 (m, 1H), 3.85 (d, J=15.4 Hz, 1H), 3.11–2.91 (m, 5H), 2.84–2.59 (m, 2H), 1.19 (t, J=7.4 Hz, 3H)

REFERENCE EXAMPLE 62

Synthesis of Compound BL

Compound BL (420 mg; yield: 45%) was obtained from methyl 3-(2-ethylphenyl)-4-nitrobutyrate (500 mg, 2.0 mmol), 2-nitro-4-thiophenecarboxaldehyde (0.1 mL, 2.0 mmol) and 3-aminomethylpyridine (0.2 mL, 2.0 mmol) in a manner similar to that in Reference Example 1.

$^1$H-NMR (CDCl$_3$, 300 MHz) δ 8.41 (dd, J=4.9, 1.7 Hz, 1H) 8.17 (d, J=1.7 Hz, 1H), 7.69 (d, J=2.0 Hz, 1H), 7.43 (dt, J=7.9, 2.0 Hz, 1H), 7.27 (d, J=2.0 Hz, 1H), 7.19–7.06 (m, 5H), 5.19 (dd, J=11.2, 9.1 Hz, 1H), 4.93 (d, J=9.1 Hz, 1H), 4.81 (d, J=15.2 Hz, 1H), 4.16 (d, J=15.2 Hz, 1H), 3.99 (m, 1H), 2.92–2.83 (m, 2H), 2.67–2.48 (m, 2H), 1.10 (t, J=7.4 Hz, 3H)

REFERENCE EXAMPLE 63

Synthesis of Compound BM

Compound BM (1.0 g; yield: 48%) was obtained from methyl 3-(2-bromophenyl)-4-nitrobutyrate (1.2 g, 4.0 mmol), 2-nitro-4-thiophenecarboxaldehyde (630 mg, 4.0 mmol) and 3-aminomethylpyridine (0.4 mL, 4.0 mmol) in a manner similar to that in Reference Example 1.

$^1$H-NMR (CDCl$_3$, 300 MHz) δ 8.55 (dd, J=4.8, 1.5 Hz, 1H) 8.25 (d, J=1.5 Hz,1H), 7.68 (d, J=1.9 Hz, 1H), 7.57 (dd, J=7.9, 1.3 Hz, 1H), 7.53 (dt, J=8.2, 2.0 Hz, 1H), 7.37–7.14 (m, 5H), 5.27 (dd, J=10.7, 8.5 Hz, 1H), 5.09 (d, J=15.1 Hz, 1H), 5.01 (d, J=8.5 Hz, 1H), 4.38 (m, 1H), 4.10 (d, J=15.1 Hz, 1H), 3.09 (dd, J=17.8, 5.3 Hz, 1H), 2.85 (dd, J=17.8, 12.4 Hz, 1H)

REFERENCE EXAMPLE 64

Synthesis of Compound BN

Compound BN (418 mg; yield: 30%) was obtained from methyl 3-(2-bromophenyl)-4-nitrobutyrate (600 mg, 2.0 mmol), 3-methyl-2-thiophenecarboxaldehyde (250 mg, 2.0 mmol) and 3-aminomethylpyridine (0.4 mL, 4.0 mmol) in a manner similar to that in Reference Example 1.

$^1$H-NMR (CDCl$_3$, 300 MHz) δ 8.56 (dd, J=4.6, 1.7 Hz, 1H) 8.35 (d, J=1.7 Hz, 1H), 7.62–7.55 (m, 2H), 7.36–7.12 (m, 4H), 6.69 (d, J=3.3 Hz, 1H), 6.60 (m, 1H), 5.36–5.22 (m, 2H), 5.12 (d, J=8.9 Hz, 1H), 4.33 (m, 1H), 4.02 (d, J=15.2 Hz, 1H), 3.03 (dd, J=17.5, 5.3 Hz, 1H), 2.78 (m, 1H), 2.48 (d, J=1.0 Hz, 3H)

REFERENCE EXAMPLE 65

Synthesis of Compound BO

Compound BO (220 mg; yield: 51%) was obtained from methyl 3-(2-methylthiophenyl)-4-nitrobutyrate (269 mg, 1.0 mmol), benzaldehyde (122 mg, 1.0 mmol) and 3-aminomethylpyridine (0.20 mL, 2.0 mmol) in a manner similar to that in Reference Example 1.

$^1$H-NMR (CDCl$_3$, 300 MHz) δ 8.52 (dd, J=4.6, 1.3 Hz, 1H) 8.20 (d, J=2.0 Hz, 1H), 7.53 (dt, J=7.9, 2.0 Hz, 1H), 7.37–7.14 (m, 10H), 5.40 (m, 1H), 4.91 (d, J=8.9 Hz, 1H), 4.51 (m, 1H), 3.88 (d, J=14.9 Hz, 1H), 3.04 (dd, J=17.5, 5.3 Hz, 1H), 2.85 (m, 1H), 2.44 (s, 3H)

REFERENCE EXAMPLE 66

Synthesis of Compound BP

Compound BP (260 mg; yield: 60%) was obtained from methyl 3-(2-methylthiophenyl)-4-nitrobutyrate (269 mg, 1.0 mmol), 2-pyridinecarboxaldehyde (0.095 mL, 1.0 mmol), and 3-aminomethylpyridine (0.20 mL, 2.0 mmol) in a manner similar to that in Reference Example 1.

$^1$H-NMR (CDCl$_3$, 270 MHz) δ 8.61 (d, J=4.9 Hz, 1H), 8.50 (dd, J=4.6, 1.6 Hz, 1H), 8.19 (d, J=2.0 Hz, 1H), 7.69–6.60 (m, 2H), 7.27–7.12 (m, 6H), 7.05 (d, J=8.2 Hz, 1H), 5.75 (dd, J=10.8, 7.3 Hz, 1H), 5.11–5.00 (m, 2H), 4.53 (m, 1H), 3.94 (d, J=15.2 Hz, 1H), 2.96–2.86 (m, 2H), 2.44 (s, 3H)

REFERENCE EXAMPLE 67

Synthesis of Compound BQ

Compound BQ (0.31 g; yield: 71%) was obtained from methyl 3-(2-methylthiophenyl)-4-nitrobutyrate (0.27 mg, 0.1 mmol), 3-thiophenecarboxaldehyde (0.088 g, 0.1 mmol), and 3-aminomethylpyridine (0.20 mL, 0.2 mmol) in a manner similar to that in Reference Example 1.

$^1$H-NMR (CDCl$_3$, 270 MHz) δ 8.54 (dd, J=4.8, 1.5 Hz, 1H), 8.26 (br s, 1H), 7.53 (br d, J=7.9 Hz, 1H), 7.40 (m, 1H), 7.33–7.11 (m, 6H), 6.95 (dd, J=4.9, 1.4 Hz, 1H), 5.30 (m, 1H), 5.18 (d, J=15.1 Hz, 1H), 5.05 (d, J=8.9 Hz, 1H), 4.50 (br s, 1H), 3.93 (d, J=15.8 Hz, 1H), 3.06 (dd, J=17.6, 5.4 Hz, 1H), 2.80 (m, 1H), 2.46 (s, 3H)

REFERENCE EXAMPLE 68

Synthesis of Compound BR

Compound BR (1.3 g; yield: 34%) was obtained from methyl 3-[2-((E)-1-propenyl)phenyl]-4-nitrobutyrate (2.3 g, 8.7 mmol), 3-thiophenecarboxaldehyde (1.1 g, 8.7 mmol), and 3-aminomethylpyridine (1.77 mL, 17.4 mmol) in a manner similar to that in Reference Example 1.

$^1$H-NMR (CDCl$_3$, 270 MHz) δ 8.54 (dd, J=4.8, 1.7 Hz, 1H), 8.28 (d, J=4.2 Hz, 1H), 7.51 (d, J=7.9 Hz, 1H), 7.40 (dd, J=5.1, 2.9 Hz, 1H), 7.30 (m, 1H), 7.28–7.10 (m, 6H), 6.94 (dd, J=5.1, 1.3 Hz, 1H), 6.60 (d, J=15.3 Hz, 1H), 6.01 (dq, J=15.4, 6.6 Hz, 1H), 5.22–5.03 (m, 3H), 4.14 (m, 1H), 3.97 (d, J=14.9 Hz, 1H), 2.94 (dd, J=17.6, 5.4 Hz, 1H), 2.77 (dd, J=17.6, 12.7 Hz, 1H), 1.91 (dd, J=6.6, 1.6 Hz, 1H)

REFERENCE EXAMPLE 69

Synthesis of Compound BS

Compound BS (1.3 g; yield: 37%) was obtained from methyl 3-[2-((E)-1-propenyl)phenyl]-4-nitrobutyrate (0.52 g, 2.0 mmol), 2-pyridinecarboxaldehyde (0.24 mL, 2.5 mmol), and 3-aminomethylpyridine (0.41 mL, 4.0 mmol) in a manner similar to that in Reference Example 1.

$^1$H-NMR (CDCl$_3$, 270 MHz) δ 8.62 (d, J=4.6 Hz, 1H), 8.51 (dd, J=4.6, 1.4 Hz, 1H), 8.24 (d, J=1.9 Hz, 1H), 7.67 (m, 1H), 7.58 (d, J=7.3 Hz, 1H), 7.32–7.13 (m, 6H), 7.01 (d, J=7.6 Hz, 1H), 6.63 (d, J=15.4 Hz, 1H), 5.99 (qd, J=15.4, 6.8 Hz, 1H), 5.63 (dd, J=10.5, 6.8 Hz, 1H), 5.10 (d, J=15.1 Hz, 1H), 5.04 (d, J=5.4 Hz, 1H), 4.23 (m, 1H), 3.99 (d, J=15.1 Hz, 1H), 2.98–2.83 (m, 2H), 1.92 (dd, J=6.8, 1.4 Hz, 3H)

REFERENCE EXAMPLE 70

Synthesis of Compound BT

Compound BT (405 mg; yield: 50%) was obtained from methyl 3-(2-ethylphenyl)-4-nitrobutyrate (500 mg, 2.0 mmol), 2-furfural (0.16 mL, 2.0 mmol), and 3-aminomethylpyridine (0.20 mL, 2.0 mmol) in a manner similar to that in Reference Example 1.

$^1$H-NMR (CDCl$_3$, 270 MHz) δ 8.52 (dd, J=4.8, 1.5 Hz, 1H) 8.33 (d, J=1.5 Hz, 1H), 7.55 (d, J=7.8 Hz, 1H), 7.39 (br s, 1H), 7.28–7.00 (m, 5H), 6.34–6.31 (m, 2H), 5.44 (dd, J=11.2, 8.4 Hz, 1H), 5.02 (d, J=8.6 Hz, 1H), 4.96 (d, J=15.2 Hz, 1H), 4.15–4.03 (m, 2H), 2.96–2.55 (m, 4H), 1.21 (t, J=7.6 Hz, 3H)

REFERENCE EXAMPLE 71

Synthesis of Compound BU

Compound BU (47 mg; yield: 19%) was obtained from methyl 3-(2,6-dichlorophenyl)-4-nitrobutyrate (150 mg, 0.5 mmol), benzaldehyde (69 mg, 0.5 mmol) and 3-aminomethylpyridine (0.10 mL, 1.0 mmol) in a manner similar to that in Reference Example 1.

$^1$H-NMR (CDCl$_3$, 270 MHz) δ 8.53 (d, J=4.9 Hz, 1H), 8.21 (br s, 1H), 7.50 (br d, J=7.9 Hz, 1H), 7.41–7.16 (m, 9H), 6.01 (dd, J=11.5, 8.9 Hz, 1H), 5.21 (d, J=14.9 Hz, 1H), 4.92 (d, J=8.9 Hz, 1H), 4.86 (m, 1H), 3.84 (d, J=14.9 Hz, 1H), 3.63 (dd, J=17.5, 13.5 Hz, 1H), 2.88 (dd, J=17.5, 5.2 Hz, 1H)

REFERENCE EXAMPLE 72

Synthesis of Compound BV

Compound BV (1.3 g; yield: 73%) was obtained from methyl 3-(2,6-dichlorophenyl)-4-nitrobutyrate (2.7 g, 10 mmol), 3-methyl-2-thiophenecarboxaldehyde (1.2 g, 10 mmol) and 3-aminomethylpyridine (1.77 mL, 17.4 mmol) in a manner similar to that in Reference Example 1.

$^1$H-NMR (CDCl$_3$, 270 MHz) δ 8.54 (d, J=4.6 Hz, 1H), 8.25 (br s, 1H), 7.54 (br d, J=7.9 Hz, 1H), 7.36–7.26 (m, 4H), 7.18 (dd, J=7.9, 7.1 Hz, 1H), 6.75 (d, J=5.1 Hz, 1H), 6.12 (dd, J=11.5, 9.0 Hz, 1H), 5.25 (d, J=15.0 Hz, 1H), 5.19 (d, J=9.0 Hz, 1H), 4.84 (m, 1H), 3.98 (d, J=15.0 Hz, 1H), 3.65 (dd, J=15.6, 13.4 Hz, 1H), 2.91 (dd, J=17.8, 15.6 Hz, 1H), 1.87 (s, 3H)

REFERENCE EXAMPLE 73

Synthesis of Compounds BW, BX and BY

Step 1:
m-Chloroperbenzoic acid (0.69 g, 4.0 mmol) was added to a solution (20 mL) of methyl 3-(2-methylthiophenyl)-4-nitrobutyrate (0.54 g, 2.0 mmol) in methylene chloride under cooling with ice, followed by stirring for 1 hour. The reaction solution was poured into a saturated aqueous sodium hydrogen carbonate solution and the mixture was extracted with a chloroform/methanol mixed solvent to obtain a crude oxidation product (670 mg).

Step 2:
Compound BW (68 mg; yield: 15%), Compound BX (42 mg; yield: 11%) and Compound BY (56 mg; yield: 13%) were obtained from the resulting crude 4-nitrobutyrate (300 mg, 1.0 mmol), 3-thiophenecarboxaldehyde (0.13 μl, 1.5 mmol), and 3-aminomethylpyridine (0.2 μl, 1, 2 mmol) in a manner similar to that in Reference Example 1.

Compound BW:
$^1$H-NMR (CDCl$_3$, 270 MHz) δ 8.52 (br s, 1H), 8.15–8.07 (m, 2H), 7.63–7.41 (m, 4H), 7.33–7.19 (m, 2H), 7.13 (br s, 1H), 6.93 (d, J=4.4 Hz, 1H), 5.38 (m, 1H), 5.10–4.91 (m, 2H), 4.03 (m, 1H), 3.32 (m, 1H), 3.15 (s, 3H), 2.65 (m, 1H)

Compound BX:
$^1$H-NMR (CDCl$_3$, 270 MHz) δ 8.55 (d, J=3.8 Hz, 1H), 8.23 (m, 1H), 8.06 (d, J=6.9 Hz, 1H), 7.55–7.44 (m, 3H), 7.44 (br s, 1H), 7.29–7.22 (m, 2H), 7.15 (br s, 1H), 6.98 (d, J=4.4 Hz, 1H), 5.27–5.11 (m, 2H), 4.99 (d, J=7.9 Hz, 1H), 4.19 (m, 1H), 3.95 (d, J=14.8 Hz, 1H), 3.13 (dd, J=7.5, 4.8 Hz, 1H), 2.78 (m, 1H), 2.74 (s, 3H)

Compound BY:
$^1$H-NMR (CDCl$_3$, 270 MHz) δ 8.53 (d, J=3.8 Hz, 1H), 8.25 (m, 1H), 7.90 (m, 1H), 7.60–7.45 (m, 3H), 7.40 (m, 1H), 7.38–7.23 (m, 2H), 7.14 (br s, 1H), 6.93 (d, J=4.9 Hz, 1H), 5.22 (dd, J=10.9, 8.9 Hz, 1H), 5.19–5.04 (m, 2H), 4.43 (m, 1H), 4.04 (d, J=14.8 Hz, 1H), 3.00–2.89 (m, 2H), 2.74 (s, 3H)

REFERENCE EXAMPLE 74

Synthesis of Compound BZ

Step 1:
3,4-Dihydroxybenzaldehyde (10 g, 67 mmol) was dissolved in DMF (50 mL), and potassium carbonate (20 g, 134 mmol) was added thereto, followed by stirring at room temperature for 30 minutes. Chloromethyl methyl ether (0.96 mL, 13 mmol) was added thereto, and the mixture was further stirred at room temperature for 20 hours. The reaction solution was poured into water and the mixture was extracted with chloroform. The organic layer was washed with a saturated aqueous solution of sodium chloride and dried over sodium sulfate. The solvent was evaporated under reduced pressure, and the residue was purified by silica gel column chromatography (eluted with chloroform) to obtain 3,4-bis(methoxymethoxy)benzaldehyde (6.4 g; yield: 42%).

$^1$H-NMR (CDCl$_3$, 300 MHz) δ 9.87 (s, 1H), 7.68 (d, J=1.7 Hz, 1H), 7.53–7.50 (m, 1H), 7.30 (s, 1H), 5.36 (s, 2H), 5.30 (s, 2H), 3.53 (s, 6H)

Step 2:
3,4-Bis(methoxymethoxy)benzaldehyde obtained above (1.1 g, 5.0 mmol), methyl 3-(2-bromophenyl)-4-nitrobutyrate (1.5 g, 5.0 mmol) and ammonium acetate (0.77 g, 10 mmol) were heated under reflux in ethanol for 20 hours. After the reaction, the solvent was evaporated under reduced pressure. The residue was purified by silica gel column chromatography (eluted with chloroform/methanol= 98/2) to obtain Compound BZ (1.4 g; yield: 57%).

$^1$H-NMR (CDCl$_3$, 300 MHz) δ 7.58 (d, J=8.1 Hz, 1H), 7.34–7.33 (m, 2H), 7.21–7.12 (m, 3H), 6.94–6.90 (m, 1H), 6.01 (br s, 1), 5.30–5.21 (m, 5H), 5.05–5.01 (m, 1H), 4.60–4.45 (m, 1H), 3.50 (s, 3H), 3.44 (s, 3H), 3.01 (dd, J=18, 6.1 Hz, 1H), 2.68–2.52 (m, 1H)

The present invention provides novel piperidine derivatives and pharmaceutically acceptable salts thereof which are useful as pharmaceuticals such as an antitumor agent.

While the invention has been described in detail and with reference to specific embodiments thereof, it will be apparent to one skilled in the art that various changes and modifications can be made therein without departing from the spirit and scope thereof.

This application is based on a U.S. Provisional Patent Application No. 60/216,666 filed on Jul. 7, 2000, the entire contents thereof being hereby incorporated by reference.

What is claimed is:

1. A piperidine derivative represented by formula (I):

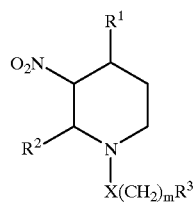

(I)

wherein
m represents an integer of 0 to 5;
$R^1$ and $R^2$ independently represent a substituted or unsubstituted lower alkyl group, a substituted or unsubstituted lower alkenyl group, a substituted or unsubstituted lower alkynyl group, a substituted or unsubstituted aryl group, a substituted or unsubstituted aralkyl group, or a substituted or unsubstituted heterocyclic group;
$R^3$ represents a hydrogen atom, a substituted or unsubstituted alkyl group, a substituted or unsubstituted aryl group, or a substituted or unsubstituted heterocyclic group; and
X represents a bond or CO;
or a pharmaceutically acceptable salt thereof,
wherein the heterocyclic groups in $R^1$, $R^2$ and $R^3$ independently represent benzopyranyl, 1,4-benzodioxanyl, 1,3-benzodioxolyl, furyl, imidazolyl, imidazothiazolyl, indolyl, piperidyl, piperazinyl, pyridyl, pyridyl N-oxide, pyrazolinyl, pyrazolyl, thiadiazolyl or thienyl.

2. The piperidine derivative or the pharmaceutically acceptable salt thereof according to claim 1, wherein $R^1$ is a substituted or unsubstituted aryl group, a substituted or unsubstituted aralkyl group, or a substituted or unsubstituted heterocyclic group, and $R^2$ is a substituted or unsubstituted aryl group, or a substituted or unsubstituted heterocyclic group.

3. The piperidine derivative or the pharmaceutically acceptable salt thereof according to claim 1, wherein m is 1 and X is a bond.

4. The piperidine derivative or the pharmaceutically acceptable salt thereof according to claim 2, wherein m is 1 and X is a bond.

5. A pharmaceutical composition which comprises as an active ingredient the piperidine derivative or the pharmaceutically acceptable salt thereof according to any one of claims 1 to 4, and a pharmaceutically acceptable diluent or carrier.

6. A method of treating a patient with colon or pancreatic cancer, which comprises administrating to said patient a pharmacologically effective amount of the piperidine derivative or the pharmaceutically acceptable salt thereof according to any one of claims 1 to 4.

7. The method of treating a patient according to claim 6, wherein the colon or pancreatic cancer is a tumor.

8. The method of treating a patient according to claim 7, wherein the tumor is pancreatic cancer.

9. The method of treating a patient according to claim 7, wherein the tumor is colon cancer.

10. The piperidine derivative or the pharmaceutically acceptable salt thereof according to claim 1, wherein m is 0.

11. The piperidine derivative or the pharmaceutically acceptable salt thereof according to claim 1, wherein m is 1.

12. The piperidine derivative or the pharmaceutically acceptable salt thereof according to claim 1, wherein m is 2.

13. The piperidine derivative or the pharmaceutically acceptable salt thereof according to claim 1, wherein m is 3.

14. The piperidine derivative or the pharmaceutically acceptable salt thereof according to claim 1, wherein m is 4.

15. The piperidine derivative or the pharmaceutically acceptable salt thereof according to claim 1, wherein m is 5.

16. The piperidine derivative or the pharmaceutically acceptable salt thereof according to claim 10, wherein X is a bond.

17. The piperidine derivative or the pharmaceutically acceptable salt thereof according to claim 12, wherein X is a bond.

18. The piperidine derivative or the pharmaceutically acceptable salt thereof according to claim 13, wherein X is a bond.

19. The piperidine derivative or the pharmaceutically acceptable salt thereof according to claim 14, wherein X is a bond.

20. The piperidine derivative or the pharmaceutically acceptable salt thereof according to claim 15, wherein X is a bond.

21. The piperidine derivative or the pharmaceutically acceptable salt thereof according to claim 10, wherein X is CO.

22. The piperidine derivative or the pharmaceutically acceptable salt thereof according to claim 11, wherein X is CO.

23. The piperidine derivative or the pharmaceutically acceptable salt thereof according to claim 12, wherein X is CO.

24. The piperidine derivative or the pharmaceutically acceptable salt thereof according to claim 13, wherein X is CO.

25. The piperidine derivative or the pharmaceutically acceptable salt thereof according to claim 14, wherein X is CO.

26. The piperidine derivative or the pharmaceutically acceptable salt thereof according to claim 15 wherein X is CO.

* * * * *